US006855726B1

(12) United States Patent
Dudley et al.

(10) Patent No.: US 6,855,726 B1
(45) Date of Patent: Feb. 15, 2005

(54) QUINOLONES AS SERINE PROTEASE INHIBITORS

(75) Inventors: Danette Andrea Dudley, Ann Arbor, MI (US); Jeremy John Edmunds, Ypsilanti, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 09/601,479

(22) PCT Filed: Dec. 15, 1998

(86) PCT No.: PCT/US98/26709

§ 371 (c)(1),
(2), (4) Date: Aug. 3, 2000

(87) PCT Pub. No.: WO99/50263

PCT Pub. Date: Oct. 7, 1999

Related U.S. Application Data
(60) Provisional application No. 60/080,090, filed on Mar. 31, 1998.

(51) Int. Cl.$^7$ .................... C07D 401/14; C07D 407/14; C07D 409/14; A61K 31/4709; A61P 7/02
(52) U.S. Cl. .................... 514/312; 514/252.1; 514/241; 514/256; 546/157; 546/158; 544/180; 544/238; 544/242; 544/336
(58) Field of Search ................................. 546/157, 158, 546/148; 544/180, 238, 242, 336; 514/252.01, 252.1, 312, 256

(56) References Cited

U.S. PATENT DOCUMENTS

| | | | |
|---|---|---|---|
| 3,330,823 A | 7/1967 | Bernstein et al. | 260/239.3 |
| 3,551,413 A | 12/1970 | Krapcho et al. | 260/239.3 |
| 4,329,347 A | 5/1982 | Muller et al. | 424/251 |
| 4,927,824 A | 5/1990 | Adler et al. | 514/241 |

FOREIGN PATENT DOCUMENTS

| | | | |
|---|---|---|---|
| DE | 25 59 509 A | 12/1976 | ......... C07D/209/34 |
| DE | 197 18 181 A | 11/1998 | |
| EP | 0 024 638 A1 | 8/1980 | |
| EP | EP 0 797 376 A2 | 9/1997 | |
| FR | 2 439 196 A | 5/1980 | |
| GB | 1305278 | 3/1970 | |
| JP | 50 142576 A | 11/1975 | |
| JP | 56-49359 | of 1981 | |
| JP | 56-125388 | of 1981 | |
| WO | WO 97/07116 | 7/1996 | |
| WO | WO 97 12869 A | 4/1997 | |

OTHER PUBLICATIONS

"Chemical Abstracts Acession No. 56:12890 HCA".
"Chemical Abstracts Acession No. 62:74780 HCA".
"Chemical Abstracts Acession No. 51:25546 HCA".
"Chemical Abstracts Acession No. 62:74780 HCA".
"Chemical Abstracts Acession No. 51:81474 HCA".
"Chemical Abstracts Acession No. 52:92876 HCA".
"Chemical Abstracts Acession No. 123:198641 HCA".
"Chemical Abstracts Acession No. 65:38425 HCA".
"Chemical Abstracts Acession No. 65:38425 HCA".
"Chemical Abstracts Acession No. 66:70538 HCA".
"Chemical Abstracts Acession No. 74:140019 HCA".
"Chemical Abstracts Acession No. 52:28698 HCA".
"Chemical Abstracts Acession No. 82:81689 HCA".
"Chemical Abstracts Acession NO. 82:81689 HCA".
"Chemical Abstracts Acession No. 51:81474 HCA".
"Chemical Abstracts Acession No. 84:17099 HCA".
Lynch, J. Jr., et al., "Primary Prevention of Coronary Arterial Thrombosis with the Factor Xa Inhibitor rTAP in a Canine Electrolytic Injury Model", *Thromb. Haemostasis*, 1995, vol. 74, No. 2, pp 640–645.
Schaffer, L., et al., "Antithrombotic Efficacy of Recombinant Tick Anticoagulant Peptide", Circulation, vol. 84, No. 4, 1991, pp 1741–1748.
Fioravanti, C., et al., "Antithrombotic Activity of Recombinant Tick Anticoagulant Peptide and Heparin in a Rabbit Model of Venous Thrombosis", *Thromb. Res.*, 1993, vol. 71, pp 317–324.
Wong, P., et al., "Antithrombotic Actions of Selective Inhibitors of Blood Coagulation Factor Xa in Rat Models of Thrombosis", Thromb. Res., 1996, vol. 83, No. 2, pp 117–126.
Edmunds, J., et al., "Chapter 6. Thrombin and Factor Xa Inhibition", Annual Reports of Medicinal Chemistry, 1996, pp 51–60.
Kunitada, S., et al., "Factor Xa Inhibitors", Curr. Pharm. Des., 1996, vol. 2, pp 531–542.
Van den Bogaert, J., et al., "Eletrophotographic Process Utilizing a Fluorescent Recording Material", Res. Discl., 1992, vol. 340, pp 607–608.
Qar, J., et al., "A Novel High Affinity Class of Ca2+ Channel Blockers", Mol. Pharmacol., 1988, vol. 33, pp 363–369.
Petyuin, P., "Substitution of the Saturated Carbon Atom During the Acidochrome Condensation of Arylides of Diarylglycoloc Acids", Ukr. Khim. Zh., 1971, vol. 37, No. 1, pp 44–46.
Timari, G. et al., "A Convenient Synthesis of Two New Indoloquinoline Alkaloids", Synlett, 1997, vol. 9, pp 1067–1067.
Lopez–Alvarado, P. et al., "1,2–Dihydroquinolin–2–one(carbostyril) Anions as Bidentate Nucleophiles in their Reactions with Aryllead Triacetates: synthesis of 1–aryl–and 3–aryl–tetrahydroquinoline–2,5,8–triones" J. Chem Soc. Perkin Trans. 1, 1997, vol.3, pp 229–233.
Chemical Abstract No. XP–002102648.
Chemical Abstract No. XP–002102649.

*Primary Examiner*—Venkataraman Balasubramanian
(74) *Attorney, Agent, or Firm*—Cynthia M. Bott; Andrew J. Leon; Charles W. Ashbrook

(57) ABSTRACT

The invention discloses quinolinones which display inhibitory effects on serine proteases such as factor Xa, thrombin and/or factor VIIa. The invention also discloses pharmaceutically acceptable salts and prodrugs of the compounds, pharmaceutically acceptable compositions comprising the compounds, their salts or prodrugs, and methods of using them a therapeutic agents for treating or preventing disease states in mammals characterized by abnormal thrombosis.

30 Claims, No Drawings

QUINOLONES AS SERINE PROTEASE INHIBITORS

This application is a 371 of PCT/US98/26709, filed Dec. 15, 1998, which claims benefit of U.S. provisional Application 60/080,090 filed Mar. 31, 1998.

FIELD OF THE INVENTION

In one aspect, this invention discloses quinolinones which display inhibitory effects on serine proteases such as factor Xa, thrombin, and/or factor VIIa. The invention also discloses pharmaceutically acceptable salts and prodrugs of the compounds, pharmaceutically acceptable compositions comprising the compounds, their salts or prodrugs, and methods of using them as therapeutic agents for treating or preventing disease states in mammals characterized by abnormal thrombosis.

BACKGROUND OF THE INVENTION

In economically developed countries, cardiovascular disease still represents a major cause of mortality. In particular, abnormal coagulation and inappropriate thrombus formation within blood vessels precipitates many acute cardiovascular disease states. While it has long been recognized that a variety of plasma proteins such as fibrinogen, serine proteases, and cellular receptors are involved in hemostasis, it is the abnormal regulation that has emerged as important contributing factors to cardiovascular disease. Thrombin can be considered the key or principal regulatory enzyme in the coagulation cascade; it serves a pluralistic role as both a positive and negative feedback regulator in normal hemostasis. However, in some pathologic conditions, the former is amplified through catalytic activation of cofactors required for thrombin generation such as factor Xa. Factor Xa, as part of the prothrombinase complex composed of non-enzymatic cofactor Va, calcium ions and a phospholipid membrane surface regulates the generation of thrombin from its zymogen prothrombin. Furthermore, the location of the prothrombinase complex at the convergence of both the intrinsic and extrinsic coagulation pathways suggests that inhibition of factor Xa, and hence thrombin generation, may be a viable approach to limiting the procoagulant activity of thrombin.

Indeed, ample evidence exists for the role of factor Xa inhibitors as anticoagulants. Antistasin, a potent inhibitor of blood coagulation factor Xa, from the Mexican leech: *Haementeria officinalis*, displays antithrombotic activity in various models of arterial and venous thrombosis (Lapatto et al., *Embo J.*, 1997:5151–61). Other protein or polypeptide factor Xa inhibitors include recombinant tick anticoagulant peptide (rTAP), which is known to accelerate the recombinant tissue plasminogen activator mediated clot lysis and prevent acute reocclusion in the dog, hence indicating factor Xa inhibitors may be useful as an adjunct to thrombolytic therapy (Mellott et al., *Fibrinolysis*, 1993:195–202). Furthermore, in a canine coronary artery, electrolytic lesion model rTAP was demonstrated to reduce thrombus mass and time to occlusion in the absence of dramatic hemodynamic or hemostatic changes indicating the primary role for factor Xa in the process of arterial thrombosis (Lynch et al., *Thromb. Haemostasis*, 1995:640–645, Schaffer et al., *Circulation*, 1991:1741–1748). On the venous side, rTAP was also demonstrated to reduce fibrin deposition in a rabbit model of venous thrombosis while having little affect on systemic hemostatic parameters (Fioravanti et al., *Thromb. Res.*, 1993:317–324). In addition to these relatively high molecular weight proteins that are not suitable as oral antithrombotic agents, there also exist examples of low molecular weight factor Xa inhibitors. In particular DX9065a, a low molecular weight synthetic factor Xa inhibitor, has also shown antithrombotic potential in various experimental thrombosis, rat models. In both arteriovenous shunt and venous stasis models inhibition of thrombus formation was achieved at doses that had little effect on APTT indicating that DX9065a is effective in preventing thrombosis and hence has therapeutic antithrombotic potential (Wong et al., *Thromb. Res.*, 1996:117–126).

The majority of factor Xa inhibitors known to date have been previously summarized in two reviews (Edmunds et al., *Annual Reports in Medicinal Chemistry*, 1996:51, Kunitada and Nagahara Curr, *Pharm. Des.*, 1996:531–542). However, it is readily apparent that there still exists a need for more effective agents that regulate factor Xa proteolytic activity.

Some quinolinones have been reported, and these compounds have displayed marked pharmacological activity:

Van den Bogaert, *Res. Discl.*, 1992;340:607–608; Qar et al., Lazdunski, Michel, *Mol. Pharmacol.*, 1988;33(4):363–369; Japanese Patent 56125388; Japanese Patent 56049359; Great Britain Patent 1305278; German Patent 2007468; Petyunin P. A., *Ukr. Khim. Zh.* 1971;37(1):44–46; U.S. Pat. No. 3,330,823; European Patent 797376; Timari et al, Hajos, Gyorgy, *Synlett* (1997); Issue 9:1067–1068; World Publication 9707116; Lopez-Alvarado Pilar, *J. Chem. Soc., Perkin Trans.* 1, 1997;Issue 3:229–233; European Patent 334135; and European Patent 24638.

None of the above articles set forth above disclose or suggest compounds of Formula I that are inhibitors of serine proteases involved in the blood coagulation cascade.

SUMMARY OF THE INVENTION

One object of the present invention is to provide serine protease inhibitors that display inhibitory activity towards enzymes involved in the coagulation cascade and principally the target enzymes, factor Xa, thrombin, and factor VIIa.

A further object of the present invention is to provide serine protease inhibitors that display inhibitory activity towards the target enzyme factor Xa and are provided for in a pharmacologically acceptable state.

Still, a further object of the present invention is to provide for the use of these factor Xa inhibitors and formulations thereof as anticoagulant and factor Xa inhibitory agents.

Yet, a further object of the present invention is to provide for the use of these factor Xa inhibitors and formulations thereof for therapeutic treatment of various thrombotic maladies.

A further object of the present invention is a process for the synthesis of these low molecular weight thrombin inhibitors. The enzyme inhibitors of the present invention are encompassed by the structure of general Formula I set forth below.

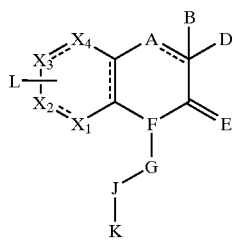

The present invention meets these objectives and provides for novel compounds that display antithrombotic activity. More specifically, the present invention provides for novel compounds that display antithrombotic activity via the inhibition of factor Xa as reflected in Formula I, or pharmaceutically acceptable salts or prodrug forms thereof. The present invention also provides pharmaceutically acceptable compositions comprising the novel compounds or their salts or prodrug forms and methods of using them as therapeutic agents for treating or preventing disease states in mammals characterized by abnormal thrombosis.

Thus, in a first embodiment, the present invention provides novel compounds of Formula I:

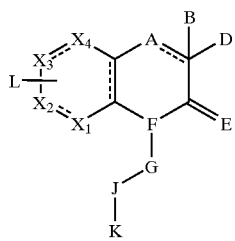

or stereoisomers or pharmaceutically acceptable salts, esters, amides, or prodrugs thereof, wherein:

A is selected from $CH_2$, CH, C(alkyl);
B is selected from H, alkyl, cycloalkyl, heteroalkyl, cycloalkylalkyl, heteroalkylalkyl, aryl, arylalkyl, heterocycle, heterocycloalkyl, each optionally substituted with $R_1$ and $R_2$;
D is selected from H, alkyl, cycloalkyl, heteroalkyl, cycloalkylalkyl, heteroalkylalkyl, aryl, arylalkyl, heterocycle, heterocycloalkyl, each optionally substituted with $R_1$ and $R_2$;
E is absent or selected from O, S, NH;
F is selected from N, $NCH_2$, $CH_2N$;
G is absent or selected from alkyl, alkyl interrupted by one or more heteroatoms, cycloalkyl, cycloalkyl interrupted by one or more heteroatoms;
J is absent or selected from aryl or heterocycle each optionally substituted with $R_1$ and $R_2$;
K is absent or selected from an alkyl, alkyl interrupted by one or more heteroatoms, cycloalkyl interrupted by one or more heteroatoms, cycloalkylalkyl interrupted by one or more heteroatoms, each optionally substituted with $R_1$ and $R_2$;
L is selected from H, chlorine, fluorine, bromine, iodine, OH, O(alkyl), amine, alkyl, fluoroalkyl, amide, $NO_2$, SH, $S(O)_n$(alkyl), $SO_3H$, $SO_3$alkyl, aldehyde, ketone, acid, ester, urea, Oalkylamide, Oalkylester, Oalkylacid, Nalkylacid, alkylamine, alkylamide, alkylketone, alkylacid, alkylester, alkylurea, Nalkylamide, Nalkylester, NC(=O)alkyl, NC(=O)aryl, nitrile, NC(=O)cycloalkyl, NC(=O)cycloalkylalkyl, NC(=O)alkylaryl, $R_1$, $R_2$;
$R_1$ is selected from H, amine, alkylamine, amide, C(=NH)NHNH$_2$, alkylC(=NH)NHNH$_2$, C(=NH)NHOH, alkylC(=NH)NHOH, NHC(=NH)NH$_2$, alkylNHC(=NH)NH$_2$, C(=S)NH$_2$, alkylC(=S)NH$_2$, C(=NH)alkyl, alkylC(=NH)alkyl, C(=NR$_3$)N(R$_4$)(R$_5$), alkylC(=NR$_3$)N(R$_4$)(R$_5$);
$R_2$ is selected from H, chlorine, fluorine, bromine, iodine, OH, Oalkyl, amine, alkylaldehyde, alkylamide, alkylester, alkylketone, alkylacid, Oalkylamide, Oalkylacid, Oalkylester, aninealkylacid, aminealkylamide, aminealkylester, NC(=O)alkyl, NC(=O)aryl, NC(=O)cycloalkyl, NC(=O)alkylaryl, alkylamine, amide, aldehyde, ester, ketone, $NO_2$, SH, $S(O)_n(C_{1-10}alkyl)$, $SO_3H$, $SO_3$alkyl, CHO, acid, alkyl, C(=NH)alkyl, C(=NH)NHNH$_2$, alkylC(=NH)NHNH$_2$, C(=NH)NHOH, alkylC(=NH)NHOH, NHC(=NH)NH$_2$, alkylNHC(=NH)NH$_2$, C(=S)NH$_2$, alkylC(=S)NH$_2$, alkylC(=NH)alkyl, C(=NR$_3$)N(R$_4$)(R$_5$), alkylC(=NR$_3$)N(R$_4$)(R$_5$);
$R_3$, $R_4$, and $R_5$ are a hydrogen atom, alkyl group having 1 to 4 carbon atoms optionally interrupted by a heteroatom, or $R_4$ and $R_5$ are bonded to form —(CH$_2$)$_p$—W—(CH$_2$)$_q$-, wherein p and q are an integer of 2 or 3, a certain position on the methylene chain is unsubstituted or substituted by a n alkyl group having 1 to 4 carbon atoms, W is a direct bond, —CH$_2$—, —O—, —N(R$_6$)—, or —S(O)$_r$ wherein R$_6$ is H or alkyl, and r is 0 or 1 or 2;
n is selected from 0, 1, 2;
$X_1$ is C or N;
$X_2$ is C or N;
$X_3$ is C or N;
$X_4$ is C or N; and
represents an optional additional bond.

Preferred group of compounds have the Formula II:

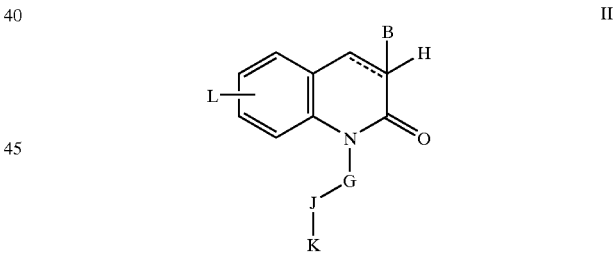

or stereoisomers or pharmaceutically acceptable salts, esters, amides, or prodrugs thereof, wherein B, G, H, K, L, and—are as defined above.

More preferred compounds provided by this invention are compounds of Formula III

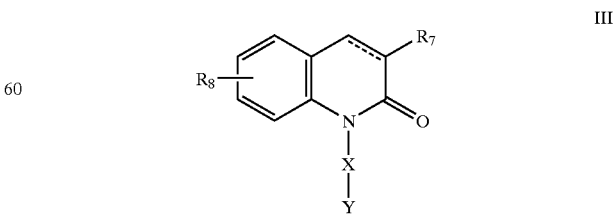

wherein X, Y, $R_7$, $R_8$, and—are as follows:

X is selected from $(CH_2)_5$,
$(CH_2)_4$,
$(CH_2)_6$,
$CH_2C(=O)NHCH_2CH_2$,
$CH_2CH_2NHC(=O)CH$,
$(CH_2)_2NH(CH_2)_2$,
$(CH_2)_2O(CH_2)_2$,
$C_6H_4$,
$CH_2C_6H_4$,
$C_6R_4CH_2$,
$C_6H_{10}$,
$CH_2C_6H_{10}$
$C_6H_{10}CH_2$,
$C_5H_8$,
$CH_2C_5H_8$,
$CH_5CH_2$, and
$CH_2CH=CHCH_2CH_2$;
Y is selected from 2,6-dimethylpiperidinyl,
piperidinyl,
2,6,6-tetramethyl-piperidinyl-4-one,
(2-carboxy)piperidinyl,
(3-carboxy)piperidinyl,
(4-carboxy)piperidinyl,
3,5-dimethylpiperidinyl,
(4-hydroxy)piperidinyl,
(2-imino)piperidinyl,
piperidin-4-one-yl,
(2-dimethylaminomethyl)-piperidinyl,
(4-dimethylamino)-piperidinyl,
(4-sulphonyloxy)-piperidinyl,
(2-phenyl)piperidinyl, 2,5-dimethylpyrrolidinyl,
pyrrolidinyl,
(2-carboxy)pyrrolidinyl,
(3-N-acetyl-N-methyl)pyrrolidinyl,
(3-amino)pyrrolidinyl, (2,5-bis-methoxymethyl)-pyrrolidinyl,
2-hydroxymethyl-pyrrolidinyl,
2-hydroxymethyl-5-methyl-pyrrolidinyl,
diisopropylamino,
diethylamino,
methylamino,
1-methyl-4,5-dihydro-1H-imidazol-2-yl,
2,5-dimethyl-1H-1-imidazolyl, morpholinyl,
2,6-dimethylmorpholinyl,
piperazinyl,
2,6-dimethylpiperazinyl,
1H-pyrazolyl,
tetrahydro-1H-pyrazolyl,
2,5-dimethyltetrahydro-1H-1-pyrazolyl, and
1,2,3,4-tetrahydro-2-oxo-3-phenyl-1-quinolinyl;
$R_7$ is selected from (3-amidino)phenyl,
phenyl,
4-methoxyphenyl,
4-(amidino)phenyl,
3-(aminocarbonyl)phenyl,
3-(methoxycarbonyl)phenyl,
(3-hydroxy)phenyl,
[3-hydroxylamino(imino)methyl]-phenyl,
[3-hydrazino(imino)methyl]-phenyl,
(3-aminomethyl)phenyl,
(3-amino)phenyl,
(3-methylamino)phenyl,
(3-dimethylamino)phenyl,
(5-amidino-2-hydroxy)phenyl,
(1-amidino)piperid-3-yl,
(1-amidino)pyrrolid-3-yl,
(5-amidino)thien-2-yl,
(5-amidino)furan-2-yl,
(5-amidino)-1,3-oxazol-2-yl,
(2-amidino)-1,3-oxazol-5-yl,
1H-pyrazol-5-yl, tetrahydro-1H-pyrazol-3-yl,
(1-amidino)tetrahydro-1H-pyrazol-3-yl,
(2-amidino)-1H-imidazol-4-yl,
(2-amino)-1H-imidazol-4-yl,
(5-amidino)-1H-imidazol-2-yl,
(5-amino)-1H-imidazol-2-yl,
pyridin-3-yl,
(4-amino)pyridin-3-yl,
(4-dimethylamino)pyridin-3-yl,
(6-amino)pyridin-2-yl,
(6-amidino)pyridin-2-yl,
(2-amino)pyridin-4-yl,
(2-amidino)pyridin-4-yl,
(2-amidino)pyrimid-4-yl,
(2-amino)pyrimidin-4-yl,
(4-amidino)pyrimid-2-yl,
(4-amino)pyrimidin-2-yl,
(6-amidino)pyrazin-2-yl,
(6-amino)pyrazin-2-yl,
(4-amidino)-1,3,5-triazin-2-yl,
(4-amino)-1,3,5-triazin-2-yl,
(3-amidino)-1,2,4-triazin-5-yl,
(3-amino)-1,2,4-triazin-5-yl,
(3-amidino)benzyl,
(3-amino)benzyl-$_7$
(3-aminomethyl)benzyl,
(1-amidino)piperid-3-ylmethyl,
(1-amidino)pyrrolid-3-ylmethyl,
(1-amidino)thien-2-ylmethyl,
(5-amidino)furan-2-ylmethyl, (5-amidino)oxazol-2-ylmethyl,
(2-amidino)imidazol-5-ylmethyl,
(5-amidino)imidazol-2-ylmethyl,
(6-amidino)pyridin-2-ylmethyl,
(6-amino)pyridin-2-ylmethyl,
(2-amidino)pyrimidin-4-ylmethyl,
(2-amino)pyrimidin-4-ylmethyl,
(4-amidino)pyrimidin-2-ylmethyl,
(4-amino)pyrimidin-2-ylmethyl,
(6-amidino)pyrazin-2-ylmethyl,
(6-amino)pyrazin-2-ylmethyl,
3-aminocyclohexyl,
3-amidinocyclohexyl,
3-aminocyclohexylmethyl, 3-amidinocyclohexylmethyl,
3-aminocyclopentyl,
3-amidinocyclopentyl,
3-aminocyclopentylmethyl, and
3-amidinocyclopentylmethyl; and
$R_8$ is selected from H,
Cl,
F,
SH,
SMe,
$CF_3$,
$CH_3$,
$CO_2H$,
$CO_2Me$,
CN,
$C(=NH)NH_2$,
$C(=NH)NHOH$,
$C(=NH)NHNH_2$,
$C(=O)NH_2$,
$CH_2OH$,
$CH_2NH_2$,
$NO_2$,
OH,
OMe,
$OCH_2Ph$,
$OCH_2CO_2H$,
$O(CH_2)_2CO_2H$,
$O(CH_2)_3CO_2H$,
$NHCH_2CO_2H$,
$NH(CH_2)_2CO_2H$,
$NH(CH_2)_3CO_2H$,
$OCH_2CH_2OH$,
$OCH_2(1H\text{-tetrazol-5-yl})$,
$NH_2$,
NHButyl,
$NMe_2$,
NHPh,
$NHCH_2Ph$,
$NHC(=O)Me$,
$NHC(=O)c\text{-Hexyl}$,
$NHC(=O)CH_2c\text{-Hexyl}$,
$NHC(=O)Ph$,
$NHC(=O)CH_2Ph$,
$NHS(=O)_2Me$,
$NHS(=O)_2c\text{-Hexyl}$,
$NHS(=O)_2CH_2c\text{-Hexyl}$,
$NHS(=O)_2Ph$, and
$NHS(=O)_2CH_2Ph$;

or stereoisomers or pharmaceutically acceptable salts, esters, amides, or prodrugs thereof.

The most preferred compounds provided by this invention are compounds of Formula IV

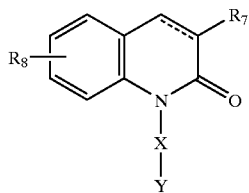

IV wherein X, Y, $R_7$, $R_9$, and—are as follows:
X is selected from $(CH_2)_5$,
$(CH_2)_4$
$(CH_2)_6$,
$CH_2C(=O)NHCH_2CH_2$,
$CH_2CH_2NHC(=O)CH_2$,
$(CH_2)_2NH(CH_2)_2$,
$(CH_2)_2O(CH_2)_2$,
$C_6H_4$,
$CH_2C_6H_4$,
$C_6H_4CH_2$,
$C_6H_{10}$,
$CH_2C_6H_{10}$,
$C_6H_{10}CH_2$,
$C_5H_8$,
$CH_2C_5H_8$,
$C_5H_8CH_2$, and
$CH_2CH=CHCH_2CH_2$;
Y is selected from 2,6-dimethylpiperidinyl,
piperidinyl,
2,2,6,6-tetramethyl-piperidinyl-4-one,
(2-carboxy)piperidinyl,
(3-carboxy)piperidinyl,
(4-carboxy)piperidinyl,
3,5-dimethylpiperidinyl,
(4-hydroxy)piperidinyl,
(2-imino)piperidinyl,
piperidin-4-one-yl,
(2-dimethylaminomethyl)-piperidinyl,
(4-dimethylamino)-piperidinyl,
(4-sulphonyloxy)-piperidinyl,
(2-phenyl)piperidinyl,
2,5-dimethylpyrrolidinyl,
pyrrolidinyl,
(2-carboxy)pyrrolidinyl,
(3-N-acetyl-N-methyl)pyrrolidinyl,
(3-amino)pyrrolidinyl,
(2,5-bis-methoxymethyl)-pyrrolidinyl,
2-hydroxymethyl-pyrrolidinyl,
2-hydroxymethyl-5-methyl-pyrrolidinyl,
diisopropylamino,
diethylamino,
methylamino,
1-methyl-4,5-dihydro-1H-imidazol-2-yl,
2,5-dimethyl-1H-1-imidazolyl,
morpholinyl, 2,6-dimethylmorpholinyl,
piperazinyl,
2,6-dimethylpiperazinyl,
1H-pyrazolyl,
tetrahydro-1H-pyrazolyl, and
2,5-dimethyltetrahydro-1H-1-pyrazolyl;
$R_7$ is selected from (3-amidino)phenyl,
(3-hydroxy)phenyl,
[3-hydroxylamino(imino)methyl]-phenyl,
[3-hydrazino(imino)methyl]-phenyl,
(3-aminomethyl)phenyl,
(3-amino)phenyl,
(3-methylamino)phenyl,
(3-dimethylamino)phenyl,
(5-amidino-2-hydroxy)phenyl,
(1-amidino)piperid-3-yl,
(1-amidino)pyrrolid-3-yl,
(5-amidino)thien-2-yl,
(5-amidino)furan-2-yl,
(5-amidino)-1,3-oxazol-2-yl,
(2-amidino)-1,3-oxazol-5-yl,
1H-pyrazol-5-yl,
tetrahydro-1H-pyrazol-3-yl,
(1-amidino)tetrahydro-1H-pyrazol-3-yl,
(2-amidino)-1H-imidazol-4-yl,
(2-amino)-1H-imidazol-4-yl,
(5-amidino)-1H-imidazol-2-yl,
(5-amino)-1H-imidazol-2-yl,
pyridin-3-yl,
(4-amino)pyridin-3-yl,
(4-dimethylamino)pyridin-3-yl,
(6-amino)pyridin-2-yl,
(6-amidino)pyridin-2-yl,
(2-amino)pyridin-4-yl,
(2-amidino)pyridin-4-yl,
(2-amidino)pyrimid-4-yl,
(2-amino)pyrimidin-4-yl,
(4-amidino)pyrimid-2-yl,
(4-amino)pyrimidin-2-yl,
(6-amidino)pyrazin-2-yl,
(6-amino)pyrazin-2-yl,
(4-amidino)-1,3,5-triazin-2-yl,
(4-amino)-1,3,5-triazin-2-yl,
(3-amidino)-1,2,4-triazin-5-yl,
(3-amino)-1,2,4-triazin-5-yl,
(3-amidino)benzyl,
(3-amino)benzyl,
(3-aminomethyl)benzyl,
(1-amidino)piperid-3-ylmethyl,
(1-amidino)pyrrolid-3-ylmethyl,
(5-amidino)thien-2-ylmethyl,
(5-amidino)furan-2-ylmethyl,
(5-amidino)oxazol-2-ylmethyl,
(2-amidino)imidazol-5-ylmethyl,
(5-amidino)imidazol-2-ylmethyl,
(6-amidino)pyridin-2-ylmethyl,
(6-amino)pyridin-2-ylmethyl,
(2-amidino)pyrimidin-4-ylmethyl,
(2-amino)pyrimidin-4-ylmethyl,
(4-amidino)pyrimidin-2-ylmethyl,
(4-amino)pyrimidin-2-ylmethyl,
(6-amidino)pyrazin-2-ylmethyl,
(6-amino)pyrazin-2-ylmethyl,
3-aminocyclohexyl,
3-amidinocyclohexyl,
3-aminocyclohexylmethyl,
3-amidinocyclohexylmethyl,
3-aminocyclopentyl,
3-amidinocyclopentyl,
3-aminocyclopentylmethyl, and
3-amidinocyclopentylmethyl; and
$R_8$ is selected from H,
Cl,
F,
SH,
SMe,
$CF_3$,
$CH_3$,
$CO_2H$,
$CO_2Me$,
CN,
$C(=NH)NH_2$,
$C(=NH)NHOH$,
$C(=NH)NHNH_2$,
$C(=O)NH_2$,
$CH_2OH$,
$CH_2NH_2$,
$NO_2$,
OH,
OMe,
$OCH_2Ph$,
$OCH_2CO_2H$,
$O(CH_2)_2CO_2H$,
$O(CH_2)_3CO_2H$,
$NHCH_2CO_2H$,
$NH(CH_2)_2CO_2H$,
$NH(CH_2)_3CO_2H$,
$OCH_2CH_2OH$,
$OCH_2$(1H-tetrazol-5-yl),
$NH_2$,
NHButyl,
$NMe_2$,
NHPh,
$NHCH_2Ph$,
$NHC(=O)Me$,
$NHC(=O)$c-Hexyl,
$NHC(=O)CH_2$c-Hexyl,
$NHC(=O)Ph$,
$NBC(=O)CH_2Ph$,
$NHS(=O)_2Me$,
$NHS(=O)_2$c-Hexyl,
$NHS(=O)_2CH2$c-Hexyl, NHS(=O)₂Ph, and
NHS(=O)₂CH₂Ph;
or stereoisomers or pharmaceutically acceptable salts, esters, amides, or prodrugs thereof.

In one embodiment of Formula IV, Y, $R_7$, and $R_8$ are as above, and X is $(CH_2)_5$.

In another embodiment of Formula IV, X, $R_7$, and $R_8$ are as above and Y is 2,6-dimethylpiperidinyl.

In another embodiment of Formula IV, X, Y, and $R_8$ are as above and $R_7$ is (2-hydroxy-5-amidino)phenyl.

In another embodiment of Formula IV, X, Y, and $R_7$ are as above and $R_8$ is H.

In another embodiment of Formula IV, $R_7$ is as above, and X is $(CH_2)_5$, Y is 2,6-dimethylpiperidinyl, and $R_8$ is H.

In another embodiment of Formula IV, $R_7$ is as above, and X is $(CH_2)_5$ and Y is 2,5-dimethylpyrrolidinyl.

Representative compounds of the present invention include:

3-(1-5-[(2R,6S)-2,6-Dimethyltetrahydro-1(2H)-pyridinyl]pentyl-2-oxo-1,2-dihydro-3-quinolinyl)benzenecarboximidamide;

1-5-[(2R,6S)-2,6-Dimethyltetrahydro-1(2H)-pyridinyl]pentyl-3-(3-hydroxyphenyl)-2(1H)-quinolinone;

3-(1-5-[(2R,6S)-2,6-Dimethyltetrahydro-1(2H)-pyridinyl]pentyl-2-oxo-1,2-dihydro-3-quinolinyl)-N-hydroxybenzenecarboximidamide;

3-(1-5-[(2R,6S)-2,6-Dimethyltetrahydro-1(2H)-pyridinyl]pentyl-2-oxo-1,2-dihydro-3-quinolinyl)benzenecarboximidohydrazide;

3-[3-(Aminomethyl)phenyl]-1-5-[(2R,6S)-2,6-dimethyltetrahydro-1(2H)-pyridinyl]pentyl-2(1H)-quinolinone;

3-(3-Aminophenyl)-1-5-[(2R,6S)-2,6-dimethyltetrahydro-1(2H)-pyridinyl]pentyl-2(1H)-quinolinone;

1-5-[(2R,6S)-2,6-Dimethyltetrahydro-1(2H)-pyridinyl]pentyl-3-[3-(methylamino)phenyl]-2(1H)-quinolinone;

3-[3-(Dimethylamino)phenyl]-1-5-[(2R,6S)-2,6-dimethyltetrahydro-1(2H)-pyridinyl]pentyl-2(1H)quinolinone;

3-(1-5-[(2R,6S)-2,6-Dimethyltetrahydro-1(2H)-pyridinyl]pentyl-2-oxo-1,2-dihydro-3-quinolinyl)-4-hydroxybenzenecarboximidamide;

3-(1-5-[(2R,6S)-2,6-Dimethyltetrahydro-1(2H)-pyridinyl]pentyl-2-oxo-1,2-dihydro-3-quinolinyl)tetrahydro-1(2H)-pyridinecarboximidamide;

3-(1-5-[(2R,6S)-2,6-Dimethyltetrahydro-1(2H)-pyridinyl]pentyl-2-oxo-1,2-dihydro-3-quinolinyl)-1-pyrrolidinecarboximidamide;

5-(1-5-[(2R,6S)-2,6-Dimethyltetrahydro-1(2H)-pyridinyl]pentyl-2-oxo-1,2-dihydro-3-quinolinyl)-2-thiophenecarboximidamide;

5-(1-5-[(2R,6S)-2,6-Dimethyltetrahydro-1(2H)-pyridinyl]pentyl-2-oxo-1,2-dihydro-3-quinolinyl)₂-furancarboximidamide;

2-(1-5-[(2R,6S)-2,6-Dimethyltetrahydro-1(2H)-pyridinyl]pentyl-2-oxo-1,2-dihydro-3-quinolinyl)-1,3-oxazole-5-carboximidamide;

5-(1-5-[(2R,6S)-2,6-Dimethyltetrahydro-1(2H)-pyridinyl]pentyl-2-oxo-1,2-dihydro-3-quinolinyl)-1,3-oxazole-2-carboximidamide;

1-5-[(2R,6S)-2,6-Dimethyltetrahydro-1(2H)-pyridinyl]pentyl-3-(1H-pyrazol-3-yl)-2(1H)-quinolinone;

1-5-[(2R,6S)-2,6-Dimethyltetrahydro-1(2H)-pyridinyl]pentyl-3-tetrahydro-1H-pyrazol-3-yl-2(1H)-quinolinone;

3-(1-5-[(2R,6S)-2,6-Dimethyltetrahydro-1(2H)-pyridinyl]pentyl-2-oxo-1,2-dihydro-3-quinolinyl)-1-pyrazolidinecarboximidamide;

5-(1-5-[(2R,6S)-2,6-Dimethyltetrahydro-1(2H)-pyridinyl]pentyl-2-oxo-1,2-dihydro-3-quinolinyl)-1H-imidazole-2-carboximidamide;

3-(2-Amino-1H-imidazol-5-yl)-1-5-[(2R,6S)-2,6-dimethyltetrahydro-1(2H)-pyridinyl]pentyl-2(1H)-quinolinone;

2-(1-5-[(2R,6S)-2,6-Dimethyltetrahydro-1(2H)-pyridinyl]pentyl-2-oxo-1,2-dihydro-3-quinolinyl)-1H-imidazole-5-carboximidamide;

3-(5-Amino-1H-imidazol-2-yl)-1-5-[(2R,6S)-2,6-dimethyltetrahydro-1 (2H)-pyridinyl]pentyl-2(1H)-quinolinone;

1-5-[(2R,6S)-2,6-Dimethyltetrahydro-1(2H)pyridinyl]pentyl-3-(3-pyridinyl)-2(1H)-quinolinone;

3-(6-Amino-3-pyridinyl)-1-5-[(2R,6S)-2,6-dimethyltetrahydro-1(2H)-pyridinyl]pentyl-2(1H)-quinolinone;

3-[6-(Dimethylamino)-3-pyridinyl]-1-5-[(2R,6S)-2,6-dimethyltetrahydro-1(2H)-pyridinyl]pentyl-2(1H)-quinolinone;

3-(6-Amino-2-pyridinyl)-1-5-[(2R,6S)-2,6-dimethyltetrahydro-1(2H)-pyridinyl]pentyl-2(1H)-quinolinone;

6-(1-5-[(2R,6S)-2,6-Dimethyltetrahydro-1(2H)-pyridinyl]pentyl-2-oxo-1,2-dihydro-3-quinolinyl)-2-pyridinecarboximidamide;

3-(2-Amino-4-pyridinyl)-1-5-[(2R,6S)-2,6-dimethyltetrahydro-1(2H)-pyridinyl]pentyl-2(1H)-quinolinone;

4-(1-5-[(2R,6S)-2,6-Dimethyltetrahydro-1(2H)-pyridinyl]pentyl-2-oxo-1,2-dihydro-3-quinolinyl)-2-pyridinecarboximidamide;

4-(1-5-[(2R,6S)-2,6-Dimethyltetrahydro-1(2H)-pyridinyl]pentyl-2-oxo-1,2-dihydro-3-quinolinyl)-2-pyrimidinecarboximidamide;

3-(2-Amino-4-pyrimidinyl)-1-5-[(2R,6S)-2,6-dimethyltetrahydro-1(2H)-pyridinyl]pentyl-2(1H)-quinolinone;

2-(1-5-[(2R,6S)-2,6-Dimethyltetrahydro-1(2H)-pyridinyl]pentyl-2-oxo-1,2-dihydro-3-quinolinyl)-4-pyrimidinecarboximidamide;

3-(4-Amino-2-pyrimidinyl)-1-5-[(2R,6S)-2,6-dimethyltetrahydro-1(2H)-pyridinyl)pentyl-2(1H)quinolinone;

6-(1-5-[(2R,6S)-2,6-Dimethyltetrahydro-1(2H)-pyridinyl]pentyl-2-oxo-1,2-dihydro-3-quinolinyl)-2-pyrazinecarboximidamide;

3-(6-Amino-2-pyrazinyl)-1-5-[(2R,6S)-2,6-dimethyltetrahydro-1(2H)-pyridinyl)pentyl-2(1H)-quinolinone;

4-(1-5-[(2R,6S)-2,6-Dimethyltetrahydro-1(2H)-pyridinyl]pentyl-2-oxo-1,2-dihydro-3-quinolinyl)-1,3,5-triazine-2-carboximidamide;

3-(4-Amino-1,3,5-triazin-2-yl)-1-5-[(2R,6S)-2,6-dimethyltetrahydro-1(2H)-pyridinyl]pentyl-2(1H)-quinolinone;

5-(1-5-[(2R,6S)-2,6-Dimethyltetrahydro-1(2H)-pyridinyl]pentyl-2-oxo-1,2-dihydro-3-quinolinyl)-1,2,4-triazine-3-carboximidamide;

3-(3-Amino-1,2,4-triazin-5-yl)-1-S-[(2R,6S)-2,6-dimethyltetrahydro-1(2H)-pyridinyl]pentyl-2(1H)quinolinone;

3-[(-5-[(2R,6S)-2,6-Dimethyltetrahydro-1(2H)-pyridinyl]pentyl-2-oxo-1,2-dihydro-3-quinolinyl)methyl]benzenecarboximidamide;

3-(3-Aminobenzyl)-1-5-[(2R,6S)-2,6-dimethyltetrahydro-1 (2H)-pyridinyl]pentyl-2(1H)-quinolinone;

3-[3-(Aminomethyl)benzyl]-1-5-[(2R,6S)-2,6-dimethyltetrahydro-1(2H)-pyridinyl]pentyl-2(1H)-quinolinone;
3-[(1-5-[(2R,6S)-2,6-Dimethyltetrahydro-1(2H)-pyridinyl]pentyl-2-oxo-1,2-dihydro-3-quinolinyl)methyl] tetrahydro-1(2H)-pyridinecarboximidamide;
3-[(1-5-[(2R,6S)-2,6-Dimethyltetrahydro-1(2H)-pyridinyl)pentyl-2-oxo-1,2-dihydro-3-quinolinyl)methyl]-1-pyrrolidinecarboximidamide;
5-[(1-5-[(2R,6S)-2,6-Dimethyltetrahydro-1(2H)pyridinyl]pentyl-2-oxo-1,2-dihydro-3-quinolinyl)methyl]-2-thiophenecarboximidamide;
5-[(1-5-[(2R,6S)-2,6-Dimethyltetrahydro-1(2H)-pyridinyl]pentyl-2-oxo-1,2-dihydro-3-quinolinyl)methyl]-2-furancarboximidamide;
2-[(1-5-[(2R,6S)-2,6-Dimethyltetrahydro-1(2H)-pyridinyl]pentyl-2-oxo-1,2-dihydro-3-quinolinyl)methyl]-1,3-oxazole-5-carboximidamide;
5-[(1-5-[(2R,6S)-2,6-Dimethyltetrahydro-1(2H)-pyridinyl]pentyl-2-oxo-1,2-dihydro-3-quinolinyl)methyl]-1H-imidazole-2-carboximidamide;
2-[(1-5-[(2R,6S)-2,6-Dimethyltetrahydro-1(2H)-pyridinyl]pentyl-2-oxo-1,2-dihydro-3-quinolinyl)methyl]-1H-imidazole-5-carboximidamide;
6-[(1-5-[(2R,6S)-2,6-Dimethyltetrahydro-1(2H)-pyridinyl]pentyl-2-oxo-1,2-dihydro-3-quinolinyl)methyl]-2-pyridinecarboximidamide;
3-[(6-Amino-2-pyridinyl)methyl]-1-5-[(2R,6S)-2,6-dimethyltetrahydro-1(2H)-pyridinyl]pentyl-2(1H)-quinolinone;
4-[(1-5-[(2R,6S)-2,6-Dimethyltetrahydro-1(2H)-pyridinyl]pentyl-2-oxo-1,2-dihydro-3-quinolinyl)methyl]-2-pyrimidinecarboximidamide;
3-[(2-Amino-4-pyrimidinyl)methyl]-1-5-[(2R,6S)-2,6-dimethyltetrahydro-1(2H)-pyridinyl]pentyl-2(1H)-quinolinone;
2-[(1-5-[(2R,6S)-2,6-Dimethyltetrahydro-1(2H)-pyridinyl]pentyl-2-oxo-1,2-dihydro-3-quinolinyl)methyl]-4-pyrimidinecarboximidamide;
3-[(4-Amino-2-pyrimidinyl)methyl]-1-5-[(2R,6S)-2,6-dimethyltetrahydro-1 (2H)-pyridinyl]pentyl-2(1H)-quinolinone;
6-[(1-5-[(2R,6S)-2,6-Dimethyltetrahydro-1(2H)-pyridinyl]pentyl-2-oxo-1,2-dihydro-3-quinolinyl)methyl]-2-pyrazinecarboximidamide;
3-((6-Amino-2-pyrazinyl)methyl]-1-5-[(2R,6S)-2,6-dimethyltetrahydro-1(2H)-pyridinyl]pentyl-2(1H)-quinolinone;
3-(3-Aminocyclohexyl)-1-5-[(2R,6S)-2,6-dimethyltetrahydro-1(2H)-pyridinyl]pentyl-2(1H)-quinolinone;
3-(1-5-[(2R,6S)-2,6-Dimethyltetrahydro-1(2H)-pyridinyl]pentyl-2-oxo-1,2-dihydro-3-quinolinyl)cyclohexanecarboximidamide;
3-[(3-Aminocyclohexyl)methyl]-1-5-[(2R,6S)-2,6-dimethyltetrahydro-1(2H)-pyridinyl]pentyl-2(1H)-quinolinone;
3-[(1-5-[(2R,6S)-2,6-Dimethyltetrahydro-1(2H)-pyridinyl-pentyl-2-oxo-1,2-dihydro-3-quinolinyl)methyl] cyclohexanecarboximidamide;
3-(3-Aminocyclopentyl)-1-5-[(2R,6S)-2,6-dimethyltetrahydro-1(2H)-pyridinyl]pentyl-2(1H)-quinolinone;
3-(-5-[(2R,6S)-2,6-Dimethyltetrahydro-1(2H)-pyridinyl]pentyl-2-oxo-1,2-dihydro-3-quinolinyl)cyclopentanecarboximidamide;
3-[(3-Aminocyclopentyl)methyl]-1-5-((2R,6S)-2,6-dimethyltetrahydro-1(2M)-pyridinyl pentyl-2(1h)quinolinone;
3-[(1-5-[(2R,6S)-2,6-Dimethyltetrahydro-1(2H)pyridinyl]pentyl-2-oxo-1,2-dihydro-3-quinolinyl)methylcyclopentanecarboximidamide;
3-(1-4[(2R,6S)-2,6-Dimethyltetrahydro-1(2H)-pyridinyl]butyl-2-oxo-1,2-dihydro-3-quinolinyl)benzenecarboximidamide;
3-(1-6-[(2R,6S)-2,6-Dimethyltetrahydro-1(2H)-pyridinyl]hexyl-2-oxo-1,2-dihydro-3-quinolinyl)benzenecarboximidamide;
2-[3-3-[Amino(imino)methyl]phenyl-2-oxo-1(2H)-quinolinyl)-N-2-[(2R,6S)-2,6-Dimethyltetrahydro-1(2H)-pyridinyl]ethylacetamide;
3-f 3-3-[Amino(imino)methyl]phenyl-2-oxo-1(2H)-quinolinyl)-N-[(2R,6S)-2,6-Dimethyltetrahydro-1(2H)-pyridinyl]methylpropanamide;
3-1-[2-(2-[(2R,6S)-2,6-Dimethyltetrahydro-1(2H)-pyridinyl]ethylamino)ethyl)-2-oxo-1,2-dihydro-3-quinolinylbenzenecarboximidamide;
3-[1-(2-2-[(2R,6S)-2,6-Dimethyltetrahydro-1(2H)-pyridinyl]ethoxyethyl)-2-oxo-1,2-dihydro-3-quinolinylbenzenecarboximidamide;
3-(14-[(2R,6S)-2,6-Dimethyltetrahydro-1(2M)-pyridinyl]phenyl-2-oxo-1,2-dihydro-3-quinolinyl)benzenecarboximidamide,
3-(1-4-[(2R,6S)-2,6-Dimethyltetrahydro-1(2H)-pyridinyl]benzyl-2-oxo-1,2-dihydro-3-quinolinyl)benzenecarboximidamide;
3-[1-(4-[(2R,6S)-2,6-Dimethyltetrahydro-1(2H)-pyridinyl]methylphenyl)-2-oxo-1,2-dihydro-3-quinolinyl]benzenecarboximidamide;
3-(1-4-[(2R,6S)-2,6-Dimethyltetrahydro-1(2H)-pyridinyl]cyclohexyl-2-oxo-1,2-dihydro-3-quinolinyl)benzenecarboximidamide;
3-[1-(4-[(2R,6S)-2,6-Dimethyltetrahydro-1(2H)-pyridinyl)cyclohexylmethyl)-2-oxo-1,2-dihydro-3-quinolinyl]benzenecarboximidamide;
3-[1-(4-[(2R,6S)-2,6-Dimethyltetrahydro-1(2H)-pyridinyl)methylcyclohexyl)-2-oxo-1,2-dihydro-3-quinolinyl]benzenecarboximidamide;
3-(1-3-[(2R,6S)-2,6-Dimethyltetrahydro-1(2H)-pyridinyl]cyclopentyl-2-oxo-1,2-dihydro-3-quinolinyl)benzenecarboximidamide;
3-[1-(3-[(2R,6S)-2,6-Dimethyltetrahydro-1(2H)-pyridinyl]cyclopentylmethyl)-2-oxo-1,2-dihydro-3-quinolinyl]benzenecarboximidamide;
3-[1-(3-[(2R,6S)-2,6-Dimethyltetrahydro-[(2H)-pyridinyl]methylcyclopentyl)$_2$-oxo-1,2-dihydro-3-quinolinyl]benzenecarboximidamide;
3-[1-(E)-5-[(2R,6S)-2,6-Dimethyltetrahydro-1(2H)-pyridinyl]-2-pentenyl-2-oxo-1,2-dihydro-3-quinolinyl)benzenecarboximidamide;
3-[2-Oxo-1-(5-piperidinopentyl)-1,2-dihydro-3-quinolinyl]benzenecarboximidamide;
3-2-Oxo-1-[5-(2,2,6,6-tetramethylpiperidino)pentyl]-1,2-dihydro-3-quinolinylbenzenecarboximidamide;
1-5-[3-3-[Amino(imino)methyl]phenyl-2-oxo-1(2H)-quinolinyl]pentyl-2-piperidinecarboxylic acid;
1-5-[3-3-[Amino(imino)methyl)phenyl-2-oxo-1(2H)-quinolinyl]pentyl-3-piperidinecarboxylic acid;
1-5-[3-3-[Amino(imino)methyl]phenyl-2-oxo-1(2H)-quinolinyl]pentyl-4-piperidinecarboxylic acid;
3-1-[5-(3,5-Dimethylpiperidino)pentyl]-2-oxo-1,2-dihydro-3-quinolinylbenzenecarboximidamide;
3-1-[5-(4-Hydroxypiperidino)pentyl]-2-oxo-1,2-dihydro-3-quinolinylbenzenecarboximidamide;
3-1-[5-(2-Iminopiperidino)pentyl]-2-oxo-1,2-dihydro-3-quinolinylbenzenecarboximidamide;

3-2-Oxo-1-[5-(4-oxopiperidino)pentyl]-1,2-dihydro-3-quinolinylbenzenecarboximidamide;

3-[1-(5-2-[(Dimethylamino)methyl]piperidinopentyl)-2-oxo-1,2-dihydro-3-quinolinyl]benzenecarboximidamide;

3-(1-5-[4-(Dimethylamino)piperidinopentyl-2-oxo-1,2-dihydro-3-quinolinyl)benzenecarboximidamide, 1-5-[3-3-[Amino(imino)methyl]phenyl-2-oxo-1(2H)quinolinyl]pentyl 1 piperidinesulfonic acid;

3-2-Oxo-1-[5-(2-phenylpiperidino)pentyl]-1,2-dihydro-3-quinolinylbenzenecarboximidamide;

3-1-[5-(2,5-Dimethyl-1-pyrrolidinyl)pentyl]-2-oxo-1,2-dihydro-3-quinolinylbenzenecarboximidamide;

3-2-Oxo-1-[5-(1-pyrrolidinyl)pentyl]-1,2-dihydro-3-quinolinylbenzenecarboximidamide;

1-5-[3-3-[Amino(imino)methyl]phenyl-2-oxo-1(2H)-quinolinyl]pentyl-2-pyrrolidonecarboxylic acid;

N-(1-5-[3-3-[Amino(imino)methyl]phenyl-2-oxo-1(2H)-quinolinyl]pentyltetrahydro-1H-pyrrol-3-yl)-N-methylacetamide;

3-1-[5-(3-Amino-1-pyrrolidinyl)pentyl]-2-oxo-1,2-dihydro-3-quinolinylbenzenecarboximidamide;

3-(1-5-[2,5-bis(Methoxymethyl)-1-pyrrolidinyl]pentyl-2-oxo-1,2-dihydro-3-quinolinyl)benzenecarboximidamide;

3-(1-5-[2-(Hydroxymethyl)-1-pyrrolidinyl]pentyl-2-oxo-1,2-dihydro-3-quinolinyl)benzenecarboximidamide;

3-(1-5-[2-(Hydroxymethyl)-5-methyl-1-pyrrolidinyl]pentyl-2-oxo-1,2-dihydro-3-quinolinyl)benzenecarboximidamide;

3-1-[5-(Diisopropylamino)pentyl]-2-oxo-1,2-dihydro-3-quinolinylbenzenecarboximidamide;

3-1-[5-(Diethylamino)pentyl]-2-oxo-1,2-dihydro-3-quinolinylbenzenecarboximidamide;

3-1-[5-(Methylamino)pentyl]-2-oxo-1,2-dihydro-3-quinolinylbenzenecarboximidamide;

3-1-[5-(1-Methyl-1H-imidazol-2-yl)pentyl]-2-oxo-1,2-dihydro-3-quinolinylbenzenecarboximidamide;

3-1-[5-(2,5-Dimethyl-1H-imidazol-1-yl)pentyl]-2-oxo-1,2-dihydro-3-quinolinylbenzenecarboximidamide;

3-[1-(5-Morpholinopentyl)-2-oxo-1,2-dihydro-3-quinolinyl]benzenecarboximidamide;

3-1-[5-(3,5-Dimethylmorpholino)pentyl]-2-oxo-1,2-dihydro-3-quinolinylbenzenecarboximidamide;

3-[2-oxo-1-(5-Piperazinopentyl)-1,2-dihydro-3-quinolinyl]benzenecarboximidamide;

3-1-[5-(2,6-Dimethylpiperazino)pentyl]-2-oxo-1,2-dihydro-3-quinolinylbenzenecarboximidamide;

3-2-Oxo-1-[5-(1H-pyrazol-1-yl)pentyl]-1,2-dihydro-3-quinolinylbenzenecarboximidamide;

3-[2-Oxo-1-(5-tetrahydro-1H-pyrazol-1-yl)pentyl]-1,2-dihydro-3-quinolinyl]benzenecarboximidamide;

3-1-[5-(2,5-Dimethyltetrahydro-1H-pyrazol-1-yl)pentyl]-2-oxo-1,2-dihydro-3-quinolinylbenzenecarboximidamide;

3-(7-Chloro-1-5-[(2R,6S)-2,6-dimethyltetrahydro-1(2H)-pyridinyl]pentyl-2-oxo-1,2-dihydro-3-quinolinyl)benzenecarboximidamide;

3-(1-5-[(2R,6S)-2,6-Dimethyltetrahydro-1(2H)-pyridinyl]pentyl-7-fluoro-2-oxo-1,2-dihydro-3-quinolinyl)benzenecarboximidamide;

3-(1-5-[(2R,6S)-2,6-Dimethyltetrahydro-1(2H)-pyridinyl]pentyl-2-oxo-7-sulfanyl-1,2-dihydro-3-quinolinyl)benzenecarboximidamide, 3-[1-5-[(2R,6S)-Dimethyltetrahydro-1(2H)-pyridinyl]pentyl-7-(methylsulfanyl)-2-oxo-1,2-dihydro-3-quinolinyl]benzenecarboximidamide;

3-[1-5-[(2R,6S)-2,6-Dimethyltetrahydro-1(2H)-pyridinyl]pentyl-2-oxo-7-(trifluoromethyl)-1,2-dihydro-3-quinolinyl]benzenecarboximidamide;

3-(1-5-[(2R,6S)-2,6-Dimethyltetrahydro-[(2H)-pyridinyl]pentyl-7-methyl-2-oxo-1,2-dihydro-3-quinolinyl)benzenecarboximidamide;

3-3-[Amino(imino)methyl]phenyl-1-5-[(2R,6S)-2,6-dimethyltetrahydro-1(2H)-pyridinyl]pentyl-2-oxo-1,2-dihydro-7-quinolinecarboxylic acid;

Methyl 3-3-[amino(imino)methyl]phenyl-1-5-((2R,6S)-2,6-dimethyltetrahydro-1(2H)-pyridinyl pentyl-2-oxo-1,2-dihydro-7-quinolinecarboxylate;

3-(7-Cyano-1-5-[(2R,6S)-2,6-dimethyltetrahydro-1(2H)-pyridinyl]pentyl-2-oxo-1,2-dihydro-3-quinolinyl)benzenecarboximidamide;

3-3-[Amino(imino)methyl]phenyl-1-5-[(2R,6S)-2,6-dimethyltetrahydro-1 (2H-pyridinyl]pentyl-2-oxo-1,2-dihydro-7-quinolinecarboximidamide;

3-3-[Amino(imino)methyl]phenyl-1-5-[(2R,6S)-2,6-dimethyltetrahydro-1(2H)-pyridinyl]pentyl-N-hydroxy-2-oxo-1,2-dihydro-7-quinolinecarboximidamide;

3-1-5-[(2R,6S)-2,6-Dimethyltetrahydro-[(2H-pyridinyl)pentyl-7-[hydrazino(imino)methyl]-2-oxo-1,2-dihydro-3-quinolinylbenzenecarboximidamide;

3-3-[Amino(imino)methyl]phenyl-1-5-[(2R,6S)-2,6-dimethyltetrahydro-1(2H)-pyridinyl]pentyl-2-oxo-1,2-dihydro-7-quinolinecarboxamide;

3-[1-5-[(2R,6S)-2,6-Dimethyltetrahydro-1(2H-pyridinyl]pentyl-7-(hydroxymethyl)-2-oxo-1,2-dihydro-3-quinolinyl]benzenecarboximidamide;

3-(7-(Aminomethyl)-1-5-[(2R,6S)-2,6-dimethyltetrahydro-[(2H)-pyridinyl]pentyl-2-oxo-1,2-dihydro-3-quinolinyl)benzenecarboximidamide;

3-(1-5-[(2R,6S)-2,6-Dimethyltetrahydro-1(2M)-pyridinyl]pentyl-7-nitro-2-oxo-1,2-dihydro-3-quinolinyl)benzenecarboximidamide;

3-(1-5-[(2R,6S)-2,6-Dimethyltetrahydro-1(2H)-pyridinyl]pentyl-7-hydroxy-2-oxo-1,2-dihydro-3-quinolinyl)benzenecarboximidamide;

3-(1-5-[(2R,6S)-2,6-Dimethyltetrahydro-1(2H)-pyridinyl]pentyl-7-methoxy-2-oxo-12-dihydro-3-quinolinyl)benzenecarboximidamide;

3-(7-(Benzyloxy)-1-5-[(2R,6S)-2,6-dimethyltetrahydro-1(2H)-pyridinyl]pentyl-2-oxo-1,2-dihydro-3-quinolinyl)benzenecarboximidamide;

2-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)oxy)acetic acid;

3-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)oxy]propanoic acid;

4-[(3-3-[Amino(imino)methyl]phenyl 1-5-[(2R,6S)-2,6-dimethyltetrahydro-1(2H)-pyridinyl]pentyl-2-oxo-1,2-dihydro-7-quinolinyl)oxy]butanoic acid;

2-[(3-3-[Amino(imino)methyl]phenyl-1-5-1(2R,6S)-2,6-dimethyltetrahydro-1(2H)-pyridinyl]pentyl-2-oxo-1,2-dihydro-7-quinolinyl)amino]acetic acid;

3-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)amino]propanoic acid;

4-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)amino]butanoic acid;

3-[1-S-[(2R,6S)-2,6-Dimethyltetrahydro-1(2H)-pyridinyl]pentyl-7-(2-hydroxyethoxy)-2-oxo-1,2-dihydro-3-quinolinyl]benzenecarboximidamide;

3-[1-5-[(2R,6S)-2,6-Dimethyltetrahydro-1(2H)-pyridinyl]pentyl-2-oxo-7-(1H-1,2,3,4-tetraazol-5-ylmethoxy)-1,2-dihydro-3-quinolinyl]benzenecarboximidamide;

3-(7-Amino-1-5-[(2R,6S)-2,6-dimethyltetrahydro-1(2H)-pyridinyl]pentyl-2-oxo-1,2-dihydro-3-quinolinyl)benzenecarboximidamide;

3-(7-(Butylamino)-1-5-[(2R,6S)-2,6-dimethyltetrahydro-1 (2H)-pyridinyl]pentyl-2-oxo-1,2-dihydro-3-quinolinyl) benzenecarboximidamide;

3-(7-(Dimethylamino)-1-5-[(2R,6S)-2,6-dimethyltetrahydro-1(2H)-pyridinyl]pentyl-2-oxo-1,2-dihydro-3-quinolinyl)benzenecarboximidamide;

3-(7-Anilino-1-5-[(2R,6S)-2,6-dimethyltetrahydro-1(2H)-pyridinyl]pentyl-2-oxo-1,2-dihydro-3-quinolinyl) benzenecarboximidamide;

3-(7-(Benzylamino)-1-5-[(2R,6S)-2,6-dimethyltetrahydro-1 (2H)-pyridinyl]pentyl-2-oxo-1,2-dihydro-3-quinolinyl) benzenecarboximidamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)acetamide;

N-(3-3-(Amino(imino)methyl]phenyl-1-5-((2R,6S)-2,6-dimethyltetrahydro-1(2H)-pyridinyl]pentyl-2-oxo-1,2-dihydro-7-quinolinyl)cyclohexanecarboxamide;

N-(3-3-[Amino(imino)methyl]phenyl-1-5-[(2R,6S)-2,6-Dimethyltetrahydro-1(2H)-pyridinyl)pentyl-2-oxo-1,2-dihydro-7-quinolinyl)-2-cyclohexylacetamide;

N-(3-3-(Amino(imino)methyl]phenyl-1-5-((2R,6S)-2,6-dimethyltetrahydro-1(2H)-pyridinyl]pentyl-2-oxo-1,2-dihydro-7-quinolinyl)benzenecarboxamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)-2-phenylacetamide;

3-1-5-[(2R,6S)-2,6-Dimethyltetrahydro-1(2H)-pyridinyl-pentyl-7-[(methylsulfonyl)amino]-2-oxo-1,2-dihydro-3-quinolinylbenzenecarboximidamide;

3-(7-[(Cyclohexylsulfonyl)amino]-1-5-[(2R,6S)-2,6-dimethyltetrahydro-1 (2H)-pyridinyl]pentyl-2-oxo-1,2-dihydro-3-quinolinyl)benzenecarboximidamide;

3-(7-[(Cyclohexylmethyl)sulfonyl]amino-1-5-[(2R,6S)-2,6-dimethyltetrahydro-1(2H)-pyridinyl]pentyl-2-oxo-1,2-dihydro-3-quinolinyl)benzenecarboximidamide;

3-1-5-[(2R,6S)-2,6-Dimethyltetrahydro-1(2H)-pyridinyl) pentyl-2-oxo-7-[(phenylsulfonyl)amino]3-1,2-dihydro-3-quinolinylbenzenecarboximidamide;

3-(7-[(Benzylsulfonyl)amino]-1-5-[(2R,6S)-2,6-dimethyltetrahydro-1(2H)-pyridinyl)pentyl-2-oxo-1,2-dihydro-3-quinolinyl)benzenecarboximidamide;

3-(1-5-[(2R,6S)-2,6-Dimethyltetrahydro-1(2H)-pyridinyl] pentyl-2-oxo-1,2,3,4-tetrahydro-3-quinolinyl) benzenecarboximidamide;

1-5-[(2R,6S)-2,6-Dimethyltetrahydro-1(2H)-pyridinyl] pentyl-3-(3-hydroxyphenyl)-3,4-dihydro-2(1H) quinolinone;

3-(1-5-[(2R,6S)-2,6-Dimethyltetrahydro-1(2H)-pyridinyl] pentyl-2-oxo-1,2,3,4-tetrahydro-3-quinolinyl)-N-hydroxybenzenecarboximidamide;

3-(1-5-[(2R,6S)-2,6-Dimethyltetrahydro-1(2H)-pyridinyl] pentyl-2-oxo-1,2,3,4-tetrahydro-3-quinolinyl) benzenecarboximidohydrazide;

3-[3-(Aminomethyl)phenyl]-1-5-[(2R,6S)-2,6-dimethyltetrahydro-1(2H)-pyridinyl]pentyl-3,4-dihydro-2(1 h)-quinolinone;

3-(3-Aminophenyl)-1-5-[(2R,6S)-2,6-dimethyltetrahydro-1 (2H)-pyridinyl]pentyl-3,4-dihydro-2(1H)-quinolinone;

1-5-[(2R,6S)-2,6-Dimethyltetrahydro-1(2H)-pyridinyl] pentyl-3-[3-(methylamino)phenyl]-3,4-dihydro-2(1H)-quinolinone;

3-[3-(Dimethylamino)phenyl]-1-5-[(2R,6S)-2,6-dimethyltetrahydro-1(2H)-pyridinyl]pentyl-3,4-dihydro-2(1H)-quinolinone;

3-(1-5-[(2R,6S)-2,6-Dimethyltetrahydro-1(2H)-pyridinyl] pentyl-2-oxo-1,2,3,4-tetrahydro-3-quinolinyl)-4-hydroxybenzenecarboximidamide;

3-(1-5-{(2R,6S)-2,6-Dimethyltetrahydro-1(2H)-pyridinyl] pentyl-2-oxo-1,2,3,4-tetrahydro-3-quinolinyl)tetrahydro-1(2H)-pyridinecarboximidamide;

3-(1-5-[(2R,6S)-2,6-Dimethyltetrahydro-1(2H)-pyridinyl] pentyl-2-oxo-1,2,3,4-tetrahydro-3-quinolinyl)-1-pyrrolidinecarboximidamide;

5-(1-5-[(2R,6S)-2,6-Dimethyltetrahydro-1(2H)-pyridinyl] pentyl-2-oxo-1,2,3,4-tetrahydro-3-quinolinyl)-2-thiophenecarboximidamide;

5-(1-5-[(2R,6S)-2,6-Dimethyltetrahydro-1(2H)-pyridinyl] pentyl-2-oxo-1,2,3,4-tetrahydro-3-quinolinyl)-2-furancarboximidamide;

2-(1-5-[(2R,6S)-2,6-Dimethyltetrahydro-1(2H)-pyridinyl] pentyl-2-oxo-1,2,3,4-tetrahydro-3-quinolinyl)-1,3-oxazole-5-carboximidamide;

5-(1-5-[(2R,6S)-2,6-Dimethyltetrahydro-1(2H)-pyridinyl] pentyl-2-oxo-1,2,3,4-tetrahydro-3-quinolinyl)-1,3-oxazole-2-carboximidamide;

1-5-[(2R,6S)-2,6-Dimethyltetrahydro-1(2H)-pyridinyl] pentyl-3-(1H-pyrazol-3-yl)-3,4-dihydro-2(1H)-quinolinone;

1-5-[(2R,6S)-2,6-Dimethyltetrahydro-1(2H)-pyridinyl] pentyl-3-tetrahydro-1H-pyrazol-3-yl-3,4-dihydro-2(1H)-quinolinone;

3-(1-5-[(2R,6S)-2,6-Dimethyltetrahydro-1(2H)-pyridinyl] pentyl-2-oxo-1,2,3,4-tetrahydro-3-quinolinyl)-1-pyrazolidinecarboximidamide;

5-(1-5-[(2R,6S)-2,6-Dimethyltetrahydro-1(2H)-pyridinyl] pentyl-2-oxo-1,2,3,4-tetrahydro-3-quinolinyl)-1H-imidazole-2-carboximidamide;

3-(2-Amino-1H-imidazol-5-yl)-1-5-[(2R,6S)-2,6-dimethyltetrahydro-1(2H)-pyridinyl]pentyl-3,4-dihydro-2(1H)-quinolinone;

2-(1-5-[(2R,6S)-2,6-Dimethyltetrahydro-1(2H)-pyridinyl] pentyl-2-oxo-1,2,3,4-tetrahydro-3-quinolinyl)-1H-imidazole-5-carboximidamide;

3-(5-Amino-1H-imidazol-2-yl)-1-5-[(2R,6S)-2,6-dimethyltetrahydro-1(2H)-pyridinyl]pentyl-3,4-dihydro-2(1H)-quinolinone;

1-5-[(2R,6S)-2,6-Dimethyltetrahydro-1(2H)-pyridinyl] pentyl-3-(3-pyridinyl)-3,4-dihydro-2(1H)-quinolinone;

3-(6-Amino-3-pyridinyl)-1-5-[(2R,6S)-2,6-dimethyltetrahydro-1(2H)-pyridinyl]pentyl-3,4-dihydro-2(1H)-quinolinone;

3-[6-(Dimethylamino)-3-pyridinyl]-1-5-[(2R,6S)-2,6-dimethyltetrahydro-1(2H)-pyridinyl]pentyl-3,4-dihydro-2(1H)-quinolinone;

3-(6-Amino-2-pyridinyl)-1-5-[(2R,6S)-2,6-dimethyltetrahydro-1(2H)-pyridinyl]pentyl-3,4-dihydro-2(1H)-quinolinone;

6-(1-5-[(2R,6S)-2,6-Dimethyltetrahydro-1(2H)-pyridinyl] pentyl-2-oxo-1,2,3,4-tetrahydro-3-quinolinyl)-2-pyridinecarboximidamide;

3-(2-Amino-4-pyridinyl)-1-5-((2R,6S)-2,6-dimethyltetrahydro-1(2H)-pyridinyl]pentyl-3,4-dihydro-2(1H)-quinolinone;

4-(1-5-[(2R,6S)2,6-Dimethyltetrahydro-1(2H)-pyridinyl] pentyl-2-oxo-1,2,3,4-tetrahydro-3-quinolinyl)-2-pyridinecarboximidamide;

4-(1-5-[(2R,6S)-2,6-Dimethyltetrahydro-1(2H)-pyridinyl] pentyl-2-oxo-1,2,3,4-tetrahydro-3-quinolinyl)-2-pyrimidinecarboximidamide;

3-(2-Amino-4-pyrimidinyl)-1-5-[(2R,6S)-2,6-dimethyltetrahydro-1(2H)-pyridinyl]pentyl-3,4-dihydro-2(1H)-quinolinone;

2-(1-5-[(2R,6S)-2,6-Dimethyltetrahydro-1(2H)-pyridinyl] pentyl-2-oxo-1,2,3,4-tetrahydro-3-quinolinyl)-4-pyrimidinecarboximidamide;

3-(4-Amino-2-pyrimidinyl)-1-5-[(2R,6S)-2,6-dimethyltetrahydro-1(2H)-pyridinyl]pentyl-3,4-dihydro-2(1H)-quinolinone;

6-(1-5-[(2R,6S)-2,6-Dimethyltetrahydro-1(2H)-pyridinyl]pentyl-2-oxo-1,2,3,4-tetrahydro-3-quinolinyl)-2-pyrazinecarboximidamide;

3-(6-Amino-2-pyrazinyl)-1-5-[(2R,6S)-2,6-dimethyltetrahydro-1(2H)-pyridinyl]pentyl-3,4-dihydro-2(1H)-quinolinone;

4-(1-5-[(2R,6S)-2,6-Dimethyltetrahydro-1(2H)-pyridinyl]pentyl-2-oxo-1,2,3,4-tetrahydro-3-quinolinyl)-1,3,5-triazine-2-carboximidamide;

3-(4-Amino-1,3,5-triazin-2-yl)-1-5-[(2R,6S)-2,6-dimethyltetrahydro-1 (2H)-pyridinyl]pentyl-3,4-dihydro-2(1H)-quinolinone;

5-(1-5-[(2R,6S)-2,6-Dimethyltetrahydro-1(2H)-pyridinyl]pentyl-2-oxo-1,2,3,4-tetrahydro-3-quinolinyl)-1,2,4-triazine-3-carboximidamide;

3-(3-Amino-1,2,4-triazin-5-yl)-1-5-[(2R,6S)-2,6-dimethyltetrahydro-1(2H)-pyridinyl]pentyl-3,4-dihydro-2(I 1H)-quinolinone;

3-[(1-5-[(2R,6S)-2,6-Dimethyltetrahydro-1(2H)-pyridinyl]pentyl-2-oxo-1,2,3,4-tetrahydro-3-quinolinyl)methyl]benzenecarboximidamide;

3-(3-Aminobenzyl)-1-5-[(2R,6S)-2,6-dimethyltetrahydro-1(2H)-pyridinyl]pentyl-3,4-dihydro-2(1H)-quinolinone;

3-[3-(Aminomethyl)benzyl]-1-5-[(2R,6S)-2,6-dimethyltetrahydro-1(2H)-pyridinyl]pentyl-3,4-dihydro-2(1H)-quinolinone;

3-[(1-5-[(2R,6S)-2,6-Dimethyltetrahydro-1(2H)-pyridinyl]pentyl-2-oxo-1,2,3,4-tetrahydro-3-quinolinyl)methyl]tetrahydro-1(2H)-pyridinecarboximidamide;

3-[(1-5-[(2R,6S)-2,6-Dimethyltetrahydro-1(2H)-pyridinyl]pentyl-2-oxo-1,2,3,4-tetrahydro-3-quinolinyl)methyl]-1-pyrrolidinecarboximidamide;

5-[(1-5-[(2R,6S)-2,6-Dimethyltetrahydro-[(2H)-pyridinyl]pentyl-2-oxo-1,2,3,4-tetrahydro-3-quinolinyl)methyl]-2-thiophenecarboximidamide;

5-[(1-5-[(2R,6S)-2,6-Dimethyltetrahydro-1(2H)-pyridinyl]pentyl-2-oxo 1,2,3,4-tetrahydro-3-quinolinyl)methyl]-2-furancarboximidamide;

2-[(1-5-[(2R,6S)-2,6-Dimethyltetrahydro-1(2H)-pyridinyl]pentyl-2-oxo-1,2,3,4-tetrahydro-3-quinolinyl)methyl]-1,3-oxazole-5-carboximidamide;

5-[(1-5-[(2R,6S)-2,6-Dimethyltetrahydro-1(2H)-pyridinyl]pentyl-2-oxo-1,2,3,4-tetrahydro-3-quinolinyl)methyl]-1H-imidazole-2-carboximidamide;

2-[(1-5-[(2R,6S)-2,6-Dimethyltetrahydro-1(2H)-pyridinyl]pentyl-2-oxo-1,2,3,4-tetrahydro-3-quinolinyl)methyl]-1H-imidazole-5-carboximidamide;

6-[(1-5-[(2R,6S)-2,6-Dimethyltetrahydro-1(2H)-pyridinyl]pentyl-2-oxo-1,2,3,4-tetrahydro-3-quinolinyl)methyl]-2-pyridinecarboximidamide;

3-[(6-Amino-2-pyridinyl)methyl]-1-5-[(2R,6S)-2,6-dimethyltetrahydro-1(2H)-pyridinyl]pentyl-3,4-dihydro-2(1)-quinolinone;

4-[(1-5-[(2R,6S)-2,6-Dimethyltetrahydro-1(2H)-pyridinyl]pentyl-2-oxo-1,2,3,4-tetrahydro-3-quinolinyl)methyl]-2-pyrimidinecarboximidamide;

3-[(2-Amino-4-pyrimidinyl)methyl]-1-5-[(2R,6S)-2,6-dimethyltetrahydro-1(2H)-pyridinyl]pentyl-3,4-dihydro-2(1H)-quinolinone;

2-[(1-5-[(2R,6S)-2,6-Dimethyltetrahydro-1(2H)-pyridinyl]pentyl-2-oxo-1,2,3,4-tetrahydro-3-quinolinyl)methyl]-4-pyrimidinecarboximidamide;

3-[(4-Amino-2-pyrimidinyl)methyl]-1-5-[(2R,6S)-2,6-dimethyltetrahydro-1(2H)-pyridinyl]pentyl-3,4-dihydro-2(1H)-quinolinone;

6-[1-5-[(2R,6S)-2,6-Dimethyltetrahydro-1(2H)-pyridinyl]pentyl-2-oxo-1,2,3,4-tetrahydro-3-quinolinyl)methyl]-2-pyrazinecarboximidamide;

3-[(6-Amino-2-pyrazinyl)methyl]-1-5-[(2R,6S)-2,6-dimethyltetrahydro-1(2H)-pyridinyl]pentyl-3,4-dihydro-2(1H)-quinolinone;

3-(3-Aminocyclohexyl)-1-5-[(2R,6S)-2,6-dimethyltetrahydro-1(2H)-pyridinyl]pentyl-3,4-dihydro-2(1H)-quinolinone;

3-(1-5-[(2R,6S)-2,6-Dimethyltetrahydro-1(2H)-pyridinyl]pentyl-2-oxo-1,2,3,4-tetrahydro-3-quinolinyl)cyclohexanecarboximidamide;

3-[(3-Aminocyclohexyl)methyl]-1-5-[(2R,6S)-2,6-dimethyltetrahydro-1 (2H)-pyridinyl]pentyl-3,4-dihydro-2(1H)-quinolinone;

3-[(1-5-[(2R,6S)-2,6-Dimethyltetrahydro-1(2H)-pyridinyl]pentyl-2-oxo-1,2,3,4-tetrahydro-3-quinolinyl)methyl]cyclohexanecarboximidamide;

3-(3-Aminocyclopentyl)-1-5-[(2R,6S)-2,6-dimethyltetrahydro-1(2H)-pyridinyl]pentyl-3,4-dihydro-2(1H)-quinolinone;

3-(1-5-[(2R,6S)-2,6-Dimethyltetrahydro-1(2H)-pyridinyl]pentyl-2-oxo-1,2,3,4-tetrahydro-3-quinolinyl)cyclopentanecarboximidamide;

3-[(3-Aminocyclopentyl)methyl]-1-5-[(2R,6S)-2,6-dimethyltetrahydro-1(2H)-pyridinyl]pentyl-3,4-dihydro-2(1H)-quinolinone;

3-[(1-5-[(2R,6S)-2,6-Dimethyltetrahydro-1(2H)-pyridinyl]pentyl-2-oxo-1,2,3,4-tetrahydro-3-quinolinyl)methyl]cyclopentanecarboximidamide;

3-(1-4-[(2R,6S)-2,6-Dimethyltetrahydro-1(2H)-pyridinyl]butyl-2-oxo-1,2,3,4-tetrahydro-3-quinolinyl)benzenecarboximidamide;

3-(1-6-[(2R,6S)-2,6-Dimethyltetrahydro-1(2H)-pyridinyl]hexyl-2-oxo-1,2,3,4-tetrahydro-3-quinolinyl)benzenecarboximidamide;

2-[3-3-[Amino(imino)methyl]phenyl-2-oxo-1(2H)-quinolinyl]-N-2-[(2R,6S)-2,6-dimethyltetrahydro-1(2H)-pyridinyl]ethylacetamide;

3-[3-3-[Amino(imino)methyl]phenyl-2-oxo-1(2H)-quinolinyl]-N-[(2R,6S)-2,6-dimethyltetrahydro-1(2H)-pyridinyl]methylpropanamide;

3-1-[2-(2-[(2R,6S)-2,6-Dimethyltetrahydro-1(2H)-pyridinyl]ethylamino)ethyl]-2-oxo-1,2,3,4-tetrahydro-3-quinolinyl]benzenecarboximidamide;

3-[1-(2-2-[(2R,6S)-2,6-Dimethyltetrahydro-1(2H)-pyridinyl]ethoxyethyl)-2-oxo-1,2,3,4-tetrahydro-3-quinolinyl]benzenecarboximidamide;

3-(1-4-[(2R,6S)-2,6-Dimethyltetrahydro-1(2H)-pyridinyl]phenyl-2-oxo-1,2,3,4-tetrahydro-3-quinolinyl)benzenecarboximidamide;

3-(1, [(2R,6S)-2,6-Dimethyltetrahydro-[(2H)-pyridinyl]benzyl-2-oxo-1,2,3,4-tetrahydro-3-quinolinyl)benzenecarboximidamide;

3-[1-(4-[(2R,6S)-2,6-Dimethyltetrahydro-1(2H)-pyridinyl]methylphenyl)-2-oxo-1,2,3,4-tetrahydro-3-quinolinyl]benzenecarboximidamide;

3-(14-[(2R,6S)-2,6-Dimethyltetrahydro-1(2H)-pyridinyl]cyclohexyl-2-oxo-1,2,3,4-tetrahydro-3-quinolinyl)benzenecarboximidamide;

3-[1-(4-[(2R,6S)-2,6-Dimethyltetrahydro-1(2H)-pyridinyl]cyclohexylmethyl)-2-oxo-1,2,3,4-tetrahydro-3-quinolinyl]benzenecarboximidamide;

3-[1-(4-[(2R,6S)-2,6-Dimethyltetrahydro-1(2H)-pyridinyl]methylcyclohexyl)-2-oxo-1,2,3,4-tetrahydro-3-quinolinyl]benzenecarboximidamide;

3-(1-3-[(2R,6S)-2,6-Dimethyltetrahydro-1(2H)-pyridinyl]-cyclopentyl-2-oxo-1,2,3,4-tetrahydro-3-quinolinyl)benzenecarboximidamide;

3-[1-(3-[(2R,6S)-2,6-Dimethyltetrahydro-1(2H)-pyridinyl]
  cyclopentylmethyl)-2-oxo-1,2,3,4-tetrahydro-3-
  quinolinyl]benzenecarboximidamide;
3-[1-(3-[(2R,6S)-2,6-Dimethyltetrahydro-1(2H)-pyridinyl]
  methylcyclopentyl)-2-oxo-1,2,3,4-tetrahydro-3-
  quinolinyl]benzenecarboximidamide;
3-(1-(E)-5-[(2R,6S)2,6-Dimethyltetrahydro-1(2M-
  pyridinyl-2-pentenyl-2-oxo-1,2,3,4-tetrahydro-3-
  quinolinyl]benzenecarboximidamide;
3-[2-Oxo-1(5-piperidinopentyl) 1,2,3,4-tetrahydro-3-
  quinolinyl]benzenecarboximidamide;
3-2-Oxo-1-[5-(2,2,6,6-tetramethylpiperidino)pentyl]-1,2,3,
  4-tetrahydro-3-quinolinylbenzenecarboximidamide;
1-5-[3-3-[Amino(imino)methyl]phenyl-2-oxo-1(2H)-
  quinolinyl]pentyl-2-piperidinecarboxylic acid;
1-S-[3-3-[Amino(imino)methyl]phenyl-2-oxo-1(2H)-
  quinolinyl]pentyl-3-piperidinecarboxylic acid;
1-5-[3-3-[(Amino(imino)methyl]phenyl-2-oxo-1(2H)-
  quinolinyl]pentyl-4-piperidinecarboxylic acid;
3-1-[5-(3,5-Dimethylpiperidino)pentyl]-2-oxo-1,2,3,4-
  tetrahydro-3-quinolinylbenzenecarboximidamide;
3-1-[5-(4-Hydroxypiperidino)pentyl]-2-oxo-1,2,3,4-
  tetrahydro-3-quinolinylbenzenecarboximidamide;
3-1-(5-(2-Iminopiperidino)pentyl]-2-oxo-1,2,3,4-
  tetrahydro-3-quinolinylbenzenecarboximidamide;
3-2-Oxo-1-[5-(4-oxopiperidino)pentyl]-1,2,3,4-tetrahydro-
  3-quinolinylbenzenecarboximidamide;
3-[1-(5-2-[(Dimethylamino)methyl]piperidinopentyl)-2-
  oxo-1,2,3,4-tetrahydro-3-quinolinyl]
  benzenecarboximidamide;
3-(1-5-[4-(Dimethylamino)piperidino]pentyl-2-oxo-1,2,3,4-
  tetrahydro-3-quinolinyl)benzenecarboximidamide;
1-5-(3-3-[amino(imino)methyl]phenyl-2-oxo-1(2H)-
  quinolinyl]pentyl-4-piperidinesulfonic acid;
3-2-Oxo-1-[5-(2-phenylpiperidino)pentyl]-1,2,3,4-
  tetrahydro-3-quinolinylbenzenecarboximidamide;
3-1-[5-(2,5-Dimethyl-1-pyrrolidinyl)pentyl]-2-oxo-1,2,3,4-
  tetrahydro-3-quinolinylbenzenecarboximidamide;
3-2-Oxo-1-[5-(1-pyrrolidinyl)pentyl]-1,2,3,4-tetrahydro-3-
  quinolinylbenzenecarboximidamide;
1-5-[3-3-[Amino(imino)methyl]phenyl-2-oxo-1(2H)-
  quinolinyl]pentyl-2-pyrrolidinecarboxylic acid;
N-(1-5-[3-3-[Amino(imino)methyl]phenyl-2-oxo-1(2H)-
  quinolinyl pentyltetrahydro-1H-pyrrol-3-yl)-N-
  methylacetamide;
3-1-[5-(3-Amino-1-pyrrolidinyl)pentyl]-2-oxo-1,2,3,4-
  tetrahydro-3-quinolinylbenzenecarboximidamide;
3-(1-5-[2,5-bis(Methoxymethyl)-1-pyrrolidinyl]pentyl-2-
  oxo-1,2,3,4-tetrahydro-3-quinolinyl)
  benzenecarboximidamide;
3-(1-5-[2-(Hydroxymethyl)-1-pyrrolidinyl]pentyl-2-oxo-1,
  2,3,4-tetrahydro-3-quinolinyl)benzenecarboximidamide;
3-(1-5-[2-(Hydroxymethyl)-5-methyl-1-pyrrolidinyl]
  pentyl-2-oxo-1,2,3,4-tetrahydro-3-quinolinyl)
  benzenecarboximidamide;
3-1-[5-(Diisopropylamino)pentyl]-2-oxo-1,2,3,4-
  tetrahydro-3-quinolinylbenzenecarboximidamide;
3-1-[5-(Diethylamino)pentyl]-2-oxo-1,2,3,4-tetrahydro-3-
  quinolinylbenzenecarboximidamide;
3-1-[5-(Methylamino)pentyl]-2-oxo-1,2,3,4-tetrahydro-3-
  quinolinylbenzenecarboximidamide;
3-1-5-(1-Methyl-1H-imidazol-2-yl)pentyl]-2-oxo-1,2,3,4-
  tetrahydro-3-quinolinylbenzenecarboximidamide;
3-1-[5-(2,5-Dimethyl-1H-imidazol-1-yl)pentyl]-2-oxo-1,2,
  3,4-tetrahydro-3-quinolinylbenzenecarboximidamide;
3-[1-(5-Morpholinopentyl)-2-oxo-1,2,3,4-tetrahydro-3-
  quinolinyl]benzenecarboximidamide;
3-1-[5-(3,5-Dimethylmorpholino)pentyl]-2-oxo-1,2,3,4-
  tetrahydro-3-quinolinylbenzenecarboximidamide;
3-[2-Oxo-1-(5-piperazino)pentyl]-1,2,3,4-tetrahydro-3-
  quinolinyl]benzenecarboximidamide;
3-1-[5-(2,6-Dimethylpiperazino)pentyl]-2-oxo-1,2,3,4-
  tetrahydro-3-quinolinylbenzenecarboximidamide;
3-2-Oxo-1-[5-(1H-pyrazol-1-yl)pentyl]-1,2,3,4-tetrahydro-
  3-quinolinylbenzenecarboximidamide;
3-[2-Oxo-1-(5-tetrahydro-1H-pyrazol-1-yl)pentyl]-1,2,3,4-
  tetrahydro-3-quinolinyl]benzenecarboximidamide;
3-1-[5-(2,5-Dimethyltetrahydro-1H-pyrazol-1-yl)pentyl]-2-
  oxo-1,2,3,4-tetrahydro-3-
  quinolinylbenzenecarboximidamide;
3-(7-Chloro-1-5-[(2R,6S)-2,6-dimethyltetrahydro-1(2H)-
  pyridinyl]pentyl-2-oxo-1,2,3,4-tetrahydro-3-quinolinyl)
  benzenecarboximidamide;
3-(1-5-[(2R,6S)-2,6-Dimethyltetrahydro-1(2H)-pyridinyl]
  pentyl-7-fluoro-2-oxo-1,2,3,4-tetrahydro-3-quinolinyl)
  benzenecarboximidamide;
3-(1-5-[(2R,6S)-2,6-Dimethyltetrahydro-1(2H)-pyridinyl]
  pentyl-2-oxo-7-sulfanyl-1,2,3,4-tetrahydro-3-quinolinyl)
  benzenecarboximidamide;
3-[1-5-[(2R,6S)-2,6-Dimethyltetrahydro-1(2H)-pyridinyl]
  pentyl-7-(methylsulfanyl)-2-oxo-1,2,3,4-tetrahydro-3-
  quinolinyl]benzenecarboximidamide;
3-(1-5-[(2R,6S)-2,6-Dimethyltetrahydro-1(2H)-pyridinyl]
  pentyl-2-oxo-7-(trifluoromethyl)-1,2,3,4-tetrahydro-3-
  quinolinyl]benzenecarboximidamide;
3-(1-5-[(2R,6S)-2,6-Dimethyltetrahydro-1(2H)-pyridinyl]
  pentyl-7-methyl-2-oxo-1,2,3,4-tetrahydro-3-quinolinyl)
  benzenecarboximidamide;
3-3-[Amino(imino)methyl]phenyl-1-5-[(2R,6S)-2,6-
  dimethyltetrahydro-1(2H)-pyridinyl]pentyl-2-oxo-1,2,3,
  4-tetrahydro-7-quinolinecarboxylic acid;
methyl 3-3-[Amino(imino)methyl]phenyl-1-5-[(2R,6S)-2,6-
  dimethyltetrahydro-1(2H)-pyridinyl]pentyl-2-oxo-1,2,3,
  4-tetrahydro-7-quinolinecarboxylate;
3-(7-Cyano-1-5-[(2R,6S)-2,6-dimethyltetrahydro-1(2H)-
  pyridinyl]pentyl-2-oxo-1,2,3,4-tetrahydro-3-quinolinyl)
  benzenecarboximidamide;
3-3-[Amino(imino)methyl]phenyl-1-5-[(2R,6S)-2,6-
  dimethyltetrahydro-1(2H)-pyridinyl]pentyl-2-oxo-1,2,3,
  4-tetrahydro-7-quinolinecarboximidamide;
3-3-[Amino(imino)methyl]phenyl-1-5-[(2R,6S)-2,6-
  dimethyltetrahydro-1 (2H)-pyridinyl]pentyl-N-hydroxy-
  2-oxo-1,2,3,4-tetrahydro-7-quinolinecarboximidamide;
3-1-5-[(2R,6S)-2,6-Dimethyltetrahydro-1(2H)-pyridinyl]
  pentyl-7-[hydrazino(imino)methyl]-2-oxo-1,2,3,4-
  tetrahydro-3-quinolinylbenzenecarboximidamide;
3-3-[Amino(imino)methyl]phenyl-1-5-[(2R,6S)-2,6-
  dimethyltetrahydro-1(2H)-pyridinyl]pentyl-2-oxo-1,2,3,
  4-tetrahydro-7-quinolinecarboxamide;
3-[1-5-[(2R,6S)-2,6-Dimethyltetrahydro-1(2H)-pyridinyl]
  pentyl-7-(hydroxymethyl)-2-oxo-1,2,3,4-tetrahydro-3-
  quinolinyl]benzenecarboximidamide;
3-(7-(Aminomethyl)-1-5-[(2R,6S)-2,6-dimethyltetrahydro-
  [(2H)-pyridinyl]pentyl-2-oxo-1,2,3,4-tetrahydro-3-
  quinolinyl)benzenecarboximidamide;
3-(1-5-[(2R,6S)-2,6-Dimethyltetrahydro-1(2H)-pyridinyl]
  pentyl-7-nitro-2-oxo-1,2,3,4-tetrahydro-3-quinolinyl)
  benzenecarboximidamide;
3-(1-5-[(2R,6S)-2,6-Dimethyltetrahydro-1(2H)-pyridinyl]
  pentyl-7-hydroxy-2-oxo-1,2,3,4-tetrahydro-3-quinolinyl)
  benzenecarboximidamide;
3-(1-5-[(2R,6S)-2,6-Dimethyltetrahydro-1(2H)-pyridinyl]
  pentyl-7-methoxy-2-oxo-1,2,3,4-tetrahydro-3-quinolinyl)
  benzenecarboximidamide;

3-(7-(Benzyloxy)-1-5-[(2R,6S)-2,6-dimethyltetrahydro-1(2H)-pyridinyl]pentyl-2-oxo-1,2,3,4-tetrahydro-3-quinolinyl)benzenecarboximidamide;

2-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)oxy]acetic acid;

3-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)oxy]propanoic acid;

4-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)oxy]butanoic acid;

2-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)amino]acetic acid;

3-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)amino]propanoic acid;

4-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)amino]butanoic acid;

3-[1-S-[(2R,6S)-2,6-Dimethyltetrahydro-1(2H)-pyridinyl]pentyl-7-(2-hydroxyethoxy)-2-oxo-1,2,3,4-tetrahydro-3-quinolinyl]benzenecarboximidamide;

3-[1-5-[(2R,6S)-2,6-Dimethyltetrahydro-1(2H)-pyridinyl]pentyl-2-oxo-7-(1H-1,2,3,4-tetraazol-5-ylmethoxy)-1,2,3,4-tetrahydro-3-quinolinyl]benzenecarboximidamide;

3-(7-Amino-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-(7-(Butylamino)-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-(7-(Dimethylamino)-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-(7-Anilino-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-(7-(Benzylamino) 1-5-((2R,6S)2,6-dimethyltetrahydro-[(21)-pyridinyl]pentyl-2-oxo-1,2,3,4-tetrahydro-3-quinolinyl)benzenecarboximidamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)acetamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)cyclohexanecarboxamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)-2-cyclohexylacetamide;

N-(3-3-[Amino(imino)methylphenyl-1-5-[(2R,6S)-2,6-dimethyltetrahydro-1(2H)-pyridinyl]pentyl-2-oxo-1,2-dihydro-7-quinolinyl)benzenecarboxamide;

3N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)-2-phenylacetamide;

3-1-5-[(2R,6S)-2,6-Dimethyltetrahydro-1(2H)-pyridinyl]pentyl-7-[(methylsulfonyl)amino]-2-oxo-1,2,3,4-tetrahydro-3-quinolinylbenzenecarboximidamide;

3-(7-[(Cyclohexylsulfonyl)amino]-1-5-[(2R,6S)-2,6-dimethyltetrahydro-1 (2H)-pyridinyl]pentyl-2-oxo-1,2,3,4-tetrahydro-3-quinolinyl)benzenecarboximidamide;

3-(7-[(Cyclohexylmethyl)sulfonyl]amino-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-1-5-[(2R,6S)-2,6-Dimethyltetrahydro-1(2H)-pyridinyl]pentyl-2-oxo-7-[(phenylsulfonyl)amino]-1,2,3,4-tetrahydro-3-quinolinylbenzenecarboximidamide;

3-(1-[5-(2,6-Dimethyl-piperidin-1-yl)-pentyl]-2-oxo-1,2-dihydro-quinolin-3-yl}-4-hydroxy-benzamidine;

4-{1-[5-(2,6-Dimethyl-piperidin-1-yl)-pentyl]-2-oxo-1,2,3,4-tetrahydro-quinolin-3-yl}-benzoic acid methyl ester;

4-{1-[5-(2,6-Dimethyl-piperidin-1-yl)-pentyl]-2-oxo-1,2,3,4-tetrahydro-quinolin-3-yl}-benzamidine;

3-Phenyl-1-(5-piperidin-1-yl-pentyl)-1H-quinolin-2-one;

3-{1-[5-(2,6-Dimethyl-piperidin-1-yl)-pentyl]-2-oxo-1,2,3,4-tetrahydro-quinolin-3-yl}-benzamide;

3-Phenyl-1-(5-piperidin-1-yl-pentyl)-3,4-dihydro-1H-quinolin-2-one;

2(1H)-Quinolinone, 1,1'-(1,5-pentylidene)bis[3,4-dihydro-3-phenyl-, (±)-;

3-(7-[(Benzylsulfonyl)amino]-1-5-[(2R,6S)-2,6-dimethyltetrahydro-1(2H)-pyridinyl]pentyl-2-oxo-1,2,3,4-tetrahydro-3-quinolinyl)benzenecarboximidamide; and 1-[5-(2,6-Dimethyl-piperidin-1-yl)-pentyl]-3-(4-methoxyphenyl)-3,4-dihydro-1H-quinolin-2-one.

DETAILED DESCRIPTION OF THE INVENTION

The term "alkyl" means a straight, branched, saturated or unsaturated carbon chain having from 1 to 20 carbon atoms. Typical alkyl groups include methyl, isobutyl, pentyl, 2-methyl-pentyl, pent-1,4-dienyl, but-1-enyl and the like.

The term "cycloalkyl" means a saturated or unsaturated carbon chain which forms a ring having from 3 to 20 carbon atoms. Typical examples include cyclopropyl, cyclohexyl and the like.

The term "cycloalkylalkyl" means a cycloalkyl group attached to an alkyl group wherein "cycloalkyl" and "alkyl" are as defined above and includes, for example, cyclopropylmethyl, cyclopentylethyl and the like.

The term "heteroalkyl" means a straight, branched, saturated or unsaturated carbon chain having from 1 to 20 carbon atoms wherein one or more carbon atoms is replaced by a heteroatom selected from oxygen, nitrogen, sulfur, sulphoxide, or sulphone. Typical "heteroalkyl" groups include methoxymethyl, 3-thiomethylpropyl, and 2-thiomethoxyethoxymethyl and the like.

The term "aryl" represents an unsaturated carbocyclic ring(s) of 6 to 16 carbon atoms which is optionally substituted with OH, O(alkyl), SH, S(alkyl), amine, halogen, acid, ester, amide, alkyl ketone, aldehyde, nitrile, fluoroalkyl, nitro, sulphone, sulfoxide, or $(C_{1-6})$alkyl. Typical rings include phenyl, naphthyl, phenanthryl, and anthracenyl. Preferred aryl rings are phenyl, substituted phenyl, and naphthyl.

The term "arylalkyl" means an aromatic radical attached to an alkyl radical wherein "aryl" and "alkyl" are as defined above and includes, for example, benzyl and naphthylmethyl.

The term "heterocycle" means a saturated or unsaturated mono- or polycyclic (i.e., bicyclic) ring incorporating one or more (i.e., 1–4) heteroatoms selected from N, O, and S. It is understood that a heterocycle is optionally substituted with OH, O(alkyl), SH, S(alkyl), amine, halogen, acid, ester, amide, alkyl ketone, aldehyde, nitrile, fluoroalkyl, nitro, sulphone, sulfoxide, or $C_{1-6}$ alkyl. Examples of suitable monocyclic heterocycles include, but are not limited to substituted or unsubstituted thienyl, furanyl, pyrrolyl, imidazolyl, pyrazolyl, thiazolyl, isothiazolyl, oxazolyl, isoxazolyl, triazolyl, tetrazolyl, pyridinyl, pyrazinyl, pyrimidinyl, piperidinyl, pyrrolidinyl, piperazinyl, azetidinyl, aziridinyl, morpholinyl, thietanyl, oyetanyl. Preferred monoydicheterocycles include, but are not limited to, 2- or 3-thienyl; 2- or 3-furanyl; 1-, 2-, or 3-pyrrolyl; 1-, 2-, 4-, or 5-imidazolyl; 1-, 3-, 4-, or 5-pyrazolyl; 2-, 4-, or 5-thiazolyl; 3-, 4- or 5-isothiazolyl; 2-, 4-, or 5-oxazolyl; 3-, 4-, or 5-isoxazolyl; 1-, 3-, or 5-triazolyl; 1-, 2-, or 3-tetrazolyl; 2-, 3-, 4-pyridinyl; 2-pyrazinyl; 2-, 4-, or 5-pyrimidinyl; 1-, 2-, 3-, or 4-piperidinyl; 1-, 2-, or 3-pyrrolidinyl; 1-, or 2-piperazinyl; 1-, 2-, or 3-azetidinyl; 1- or 2-aziridinyl; 2-, 3-, or 4-morpholinyl; 2- or 3-thietanyl; 2- or 3-oxetanyl. Examples of suitable bicyclic heterocycles include, but are not limited to, indolizinyl, isoindolyl, benzothienyl, benzoxazolyl, benzimidazolyl, quinolinyl, isoquinolinyl, and preferably 1-, 2-, 3-, 4-, 5-, 6-, or 7-indolyl; 1-, 2-, 3-, 5-, 6-, 7-, or 8-indolizinyl; 1-, 2-, 3-, 4-, 5-, 6-, or 7-isoindolyl; 2-, 3-, 4-, 5-, 6-, or 7-benzothienyl; 2-, 4-, 5-, 6-, or 7-benzoxazolyl, 1-, 2-, 4-, 5-, 6-, or 7-benzimidazolyl; 2-, 3-, 4-, 5-, 6-, 7-, or 8-quinolinyl; 1-, 3-, 4-, 5-, 6-, 7-, or 8-isoquinolinyl.

The term "heteroatom" as used herein represents oxygen, nitrogen, or sulfur (O, N, or S) as well as sulfoxyl or sulfonyl ($SO$ or $SO_2$) unless otherwise indicated. It is understood that alkyl chains interrupted by one or more heteroatoms means that a carbon atom of the chain is replaced with a heteroatom having the appropriate valency. Preferably, an alkyl chain is interrupted by 1 to 4 heteroatoms and that two adjacent carbon atoms are not both replaced. Examples of such groups include methoxymethyl, 3-thiomethylpropyl, and 2-thiomethoxyethoxymethyl.

The term "amine" refers to a group such as $NH_2$, NHalkyl, NH(cycloalkyl), NH(cycloalkylalkyl), NH(aryl), NH(arylalkyl), NH(heteroaryl), NH(heteroarylalkyl), N(alkyl)(alkyl), N(alkyl)(cycloalkyl), N(alkyl)(cycloalkylalkyl), N(alkyl)(aryl), N(alkyl)(arylalkyl), N(alkyl)(heteroaryl), N(alkyl)(heteroarylalkyl), N(cycloalkyl)(cycloalkyl), N(cycloalkyl)(cycloalkylalkyl), N(cycloalkyl)(aryl), N(cycloalkyl)(arylalkyl), N(cycloalkyl)(heteroaryl), N(cycloalkyl)(heteroarylalkyl), N(cycloalkylalkyl)(cycloalkylalkyl), N(cycloalkylalkyl)(aryl), N(cycloalkylalkyl)(arylalkyl), N(cycloalkylalkyl)(heteroaryl), N(cycloalkylalkyl)(heteroarylalkyl), N(aryl)(cycloalkylalkyl), N(aryl)(aryl), N(aryl)(arylalkyl), N(aryl)(heteroaryl), N(aryl)(heteroarylalkyl), N(arylalkyl)(arylalkyl), N(arylalkyl)(heteroaryl), N(arylalkyl)(heteroarylalkyl), N(heteroaryl)(heteroaryl), N(heteroaryl)(heteroarylalkyl), N(heteroarylalkyl)(heteroarylalkyl).

The term "acid" refers to C(=O)OH.

The term "ketone" refers to C(=O)alkyl, C(=O)cycloalkyl, C(=O)cycloalkylalkyl, C(=O)aryl, C(=O)arylalkyl, C(=O)heteroaryl, C(=O)heteroarylalkyl.

The term "ester" refers to a group such as C(=O)Oalkyl, C(=O)Ocycloalkyl, C(=O)Ocycloalkylalkyl, C(=O)Oaryl, C(=O)Oarylalkyl, C(=O)Oheteroaryl, C(=O)Oheteroarylalkyl.

The term "amide" refers to a group such as, C(=O)NH$_2$, C(=O)NHalkyl, C(=O)NH(cycloalkyl), C(=O)NH(cycloalkylalkyl), C(=O)NH(aryl), C(=O)NH(arylalkyl), C(=O)NH(heteroaryl), C(=O)NH(heteroarylalkyl), C(=O)N(alkyl)(alkyl), C(=O)N(alkyl)(cycloalkyl), C(=O)N(alkyl)(cycloalkylalkyl), C(O)N(alkyl)(aryl), C(=O)N(alkyl)(arylalkyl), C(=O)N(alkyl)(heteroaryl), C(=O)N(alkyl)(heteroarylalkyl), C(=O)N(cycloalkyl)(cycloalkyl), C(=O)N(cycloalkyl)(cycloalkylalkyl), C(=O)N(cycloalkyl)(aryl), C(=O)N(cycloalkyl)(arylalkyl), C(=O)N(cycloalkyl)(heteroaryl), C(=O)N(cycloalkyl)(heteroarylalkyl), C(=O)N(cycloalkylalkyl)(cycloalkylalkyl), C(=O)N(cycloalkylalkyl)(aryl), C(=O)N(cycloalkylalkyl)(arylalkyl), C(=O)N(cycloalkylalkyl)(heteroaryl), C(=O)N(cycloalkylalkyl)(heteroarylalkyl), C(=O)N(aryl)(cycloalkylalkyl), C(=O)N(aryl)(aryl), C(=O)N(aryl)(arylalkyl), C(=O)N(aryl)(heteroaryl), C(=O)N(aryl)(heteroarylalkyl), C(=O)N(arylalkyl)(heteroaryl), C(=O)N(arylalkyl)(heteroarylalkyl), C(=O)N(heteroaryl)(heteroaryl), C(=O)N(heteroaryl)(heteroarylalkyl), C(=O)N(heteroarylalkyl)(heteroarylalkyl).

The term "urea" refers to a group such as NHC(=O)N(alkyl)(alkyl), NHC(=O)N(alkyl)(cycloalkyl), NHC(=O)N(alkyl)(cycloalkylalkyl), NHC(=O)N(alkyl)(aryl), NHC(=O)N(alkyl)(arylalkyl), NHC(=O)N(alkyl)(heteroaryl), NHC(=O)N(alkyl)(heteroarylalkyl), NHC(=O)N(cycloalkyl)(cycloalkyl), NHC(=O)N(cycloalkyl)(cycloalkylalkyl), NHC(=O)N(cycloalkyl)(aryl), NHC(=O)N(cycloalkyl)(arylalkyl), NHC(=O)N(cycloalkyl)(heteroaryl), NHC(=O)N(cycloalkyl)(heteroarylalkyl), NHC(=O)N(cycloalkylalkyl)(cycloalkylalkyl), NHC(=O)N(cycloalkylalkyl)(aryl), NHC(=O)N(cycloalkylalkyl)(arylalkyl), NHC(=O)N(cycloalkylalkyl)(heteroaryl), NHC(=O)N(cycloalkylalkyl)(heteroarylalkyl), NHC(=O)N(aryl)(cycloalkylalkyl), NHC(=O)N(aryl)(aryl), NHC(=O)N(aryl)(arylalkyl), NHC(=O)N(aryl)(heteroaryl), NHC(=O)N(aryl)(heteroarylalkyl), NHC(=O)N(arylalkyl)(arylalkyl), NHC(=O)N(arylalkyl)(heteroaryl), NHC(=O)N(arylalkyl)(heteroarylalkyl), NHC(=O)N(heteroaryl)(heteroaryl), NHC(=O)N(heteroaryl)(heteroarylalkyl), NHC(=O)N(heteroarylalkyl)(heteroarylalkyl).

The term "halogen" refers to chlorine, fluorine, bromine, and iodine.

The wedge or hash is only one representation of a stereochemical descriptor. All stereoisomers, including enantiomers and diastereomers, are included within Formulas I to IV and are provided by this invention. When specific isomers are drawn, they are the preferred isomers.

In some situations, compounds may exist as tautomers. All tautomers are included within Formulas I to IV and are provided by this invention.

When compounds are administered, some metabolism may occur. All metabolites are included within Formulas I to IV and are provided by this invention.

When a bond to a substituent is shown to cross the bond connecting 2 atoms in a ring, then such substituent may be bonded to any atom in the ring, provided the atom will accept the substituent without violating its valency. When there appears to be several atoms of the substituent that may bond to the ring atom, then it is the first atom of the listed substituent that is attached to the ring.

When a bond is represented by a line such as "---" this is meant to represent that the bond may be absent or present provided that the resultant compound is stable and of satisfactory valency.

Compounds of the present invention are capable of forming acid addition salts (see for example, Berge S. M et al., "Pharmaceutical Salts," *Journal of Pharmaceutical Science,* 1977: 1–10) with inorganic acids such as, for example, hydrochloric acid, sulfuric acid and the like as well as salts derived from organic acids such as, for example, aliphatic mono- and dicarboxylic acids or aliphatic and aromatic sulphonic acids. The acid addition salts are prepared by contacting the free base form with a sufficient amount of the desired acid to produce the salt. The free base form may be regenerated by contacting the salt form with a base. While the free base more may differ from the salt form in terms of physical properties, such as solubility, the salts are equivalent to their respective free bases for the purposes of the present invention.

Certain compounds of the present invention can exist in unsolvated form as well as solvated form including hydrated form. In general, the solvated form including hydrated form are equivalent to unsolvated form and are intended to be encompassed within the scope of the present invention.

"Prodrugs" are intended to include any covalently bonded carrier which releases the active parent drug according to Formulas I to IV in vivo. Examples of prodrugs include acetates, formates, benzoate derivatives of alcohols, and amines present in compounds of Formulas I to IV. They also include derivatives of the amidine or guanine functionality and would include $C(=NR_3)NH_2$ where $R_3$ is selected from OH, $NH_2$, $C_{1-4}$ alkoxy, $C_{6-10}$ aryloxy, $C_{10}$ alkoxycarbonyl, $C_{6-10}$ aryloxycarbonyl. Preferred derivatives include examples wherein $R_3$ is OH, $NH_2$, methoxy, and ethoxycarbonyl.

The following table provides a list of abbreviations and definitions thereof used in the present invention.

| Abbreviation | Description |
| --- | --- |
| AMC | Aminomethylcoumarin |
| aPTT | Activated partial thromboplastin time |
| BOC | Tertiary-butyloxycarbonyl |
| BOP-reagent | Benzotriazol-1-yloxy-tris(dimethylamino) phosphonium hexafluorophosphate |
| Bz | Benzoate |
| CDCl3 | Deuterochloroform |
| DMF | Dimethyl formamide |
| DMSO | Dimethylsulfoxide |
| $^1$H-NMR | Proton nuclear magnetic resonance |
| HCl | Hydrogen chloride |
| HF | Hydrogen fluoride |
| HMPA | Hexamethylphosphoramide |
| HPLC | high pressure liquid chromatography |
| MOT | Mean occlusion time |
| MS (APCI) | Mass spectrometry (atmospheric pressure CI) |
| MS (CI) | Mass spectrometry (chemical ionization) |
| MS (ES) | Mass spectrometry (electro spray) |
| NaOH | Sodium hydroxide |
| nBuLi | n-butyl lithium |
| NH4Cl | Ammonium chloride |
| Pd/C | Palladium on carbon |
| PtO2 | Platinum oxide |
| r.t. or RT | Room temperature |
| TFA | Trifluoroacetic acid |
| THF | Tetrahydrofuran |
| TT | Thrombin time |
| VAZO-52 | 2,2'-Azobis-2-methylvaleronitrile |

Also provided by this invention is a method for preventing and treating acute, subacute, and chronic thrombotic disorder in a mammal comprising administering to such mammal an effective amount of a compound of Formulas I to IV. The compounds are useful as anticoagulants for the treatment and prophylaxis of disorders such as venous and arterial thrombosis, pulmonary embolism, and ischemic events such as myocardial infarction or cerebral infarction. These compounds also have therapeutic utility for the prevention and treatment of complications of indwelling vascular access ports and arteriovenous shunts and coagulopathies associated with cardiopulmonary bypass or other extracorporeal systems. These compounds are useful for preventing or treating unstable angina, refractory angina, intermittent claudication, disseminated intravascular coagulation, and ocular buildup of fibrin. Since thrombin and serine proteases have also been demonstrated to activate a number of different cell types, these compounds are useful for the treatment or prophylaxis of septic shock and other inflammatory responses such as acute or chronic atherosclerosis. The compounds also have utility in treating neoplasia/metastasis and neurodegenerative diseases such as Alzheimer's and Parkinson's disease. In a preferred method, the thrombotic disorder is selected from venous thrombosis, arterial thrombosis, pulmonary embolism, myocardial infarction, cerebral infarction, angina, cancer, and diabetes. A further embodiment of this invention is a pharmaceutical formulation comprising a compound of Formulas I to IV administered with a diluent, excipient, or carrier thereof.

Preparation of Compounds of the Invention

The compounds of Formulas I to IV can be prepared by any of various methods known to those skilled in the art of organic chemistry. The following general schemes represent preferred routes to provide the compounds of this disclosure. The reactions are typically performed in solvents appropriate to the reagents and substrates employed. It is understood that functionality present in the molecule must be compatible with the reagents and reaction conditions proposed. Not all compounds of Formulas I to IV falling into a given class may be compatible with some of the reaction conditions described. Such restrictions are readily apparent to those skilled in the art of organic synthesis, and alternative methods must then be used.

Quinolinones of Formula I are prepared according to Scheme 1.

Scheme 1

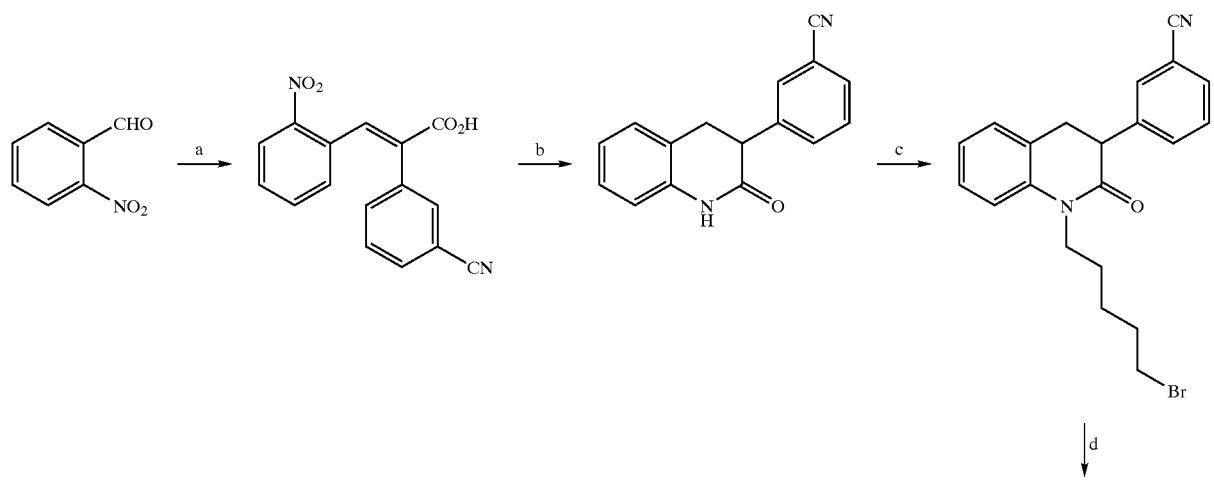

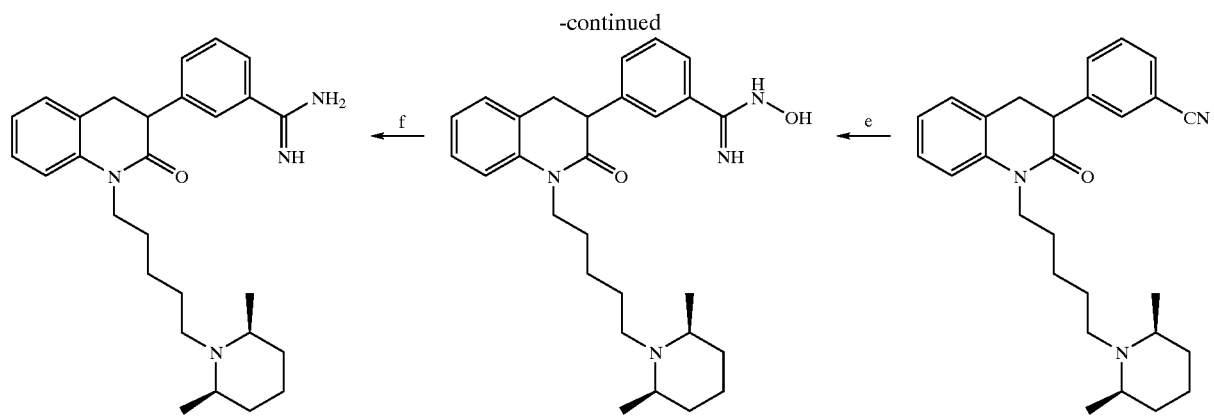

-continued

Step a:

Treatment of a suitably substituted ortho-nitro benzaldehyde with a phenyl acetic acid, such as 3-cyano-phenylacetic acid, in acetic anhydride and in the presence of base, such as triethylamine, at elevated temperatures, such as at reflux, affords the (E)-2-(3-cyanophenyl)-3-(2-nitrophenyl)prop-2-enoic acid.

Step b:

Reduction of the nitro and alkene functionality is affected by the hydrogenation of the material in the presence of palladium on carbon under a hydrogen atmosphere. Allowing this reaction to proceed for an extended period, such as 24 hours, results in the formation of the 3-(3-cyanophenyl)-1,2,3,4-tetrahydro-2-quinolinone. It is, of course, realized that the cyano substituent may undergo reduction with palladium on carbon and hydrogen. In some situations, it is necessary to employ an alternative substituent that is subsequently converted to the cyano group. Such substituents may include an ester, acid, amide, or hydroxymethyl group. Alternatively in situations where concomitant reduction of the substituents on the 3-phenyl ring, such as a bromine or cyano substituent occurs, then reduction to afford the quinolinone is affected by milder procedures such as the use of Raney nickel as a hydrogenation catalyst. It is also apparent that the $NO_2$ group may be reduced selectively, with for example, Sn/HCl, $H_2S/NH_3$ or by careful hydrogenation. These anilines may then be cyclized with sulfuric acid in acetic anhydride at elevated temperature to afford the dihydroquinolinones according to the procedure of Hino et at., *Chem. Pharm. Bull.*, 1987:2819 and Hey et al., *J. Chem. Soc.*, 1949:3164.

Step c:

Alkylation is typically achieved by treatment with an appropriate electrophile and by the addition of a base in a dipolar aprotic solvent. Typical conditions include, for example, use of a bis-electrophilic substrate such as 1,5-dibromopentane in a dipolar aprotic solvent such as DMF or DMSO and addition of a base, such as sodium hydride. Alternatively, alkylation can be achieved by the addition of a phase transfer reagent such as an alkylammonium salt, such as benzyltriethylammonium chloride, and employing a base such as sodium ethoxide. Reaction rates are typically improved by the application of heat, and hence, reactions are run at from 0° C. to 70° C.

Step d:

Treatment with an amine, such as cis-2,6-dimethylpiperidine at an elevated temperature such as 50° C. affords the expected N-alkylated piperidine. The amine may be used as solvent, or alternatively, the amine may be added in stoichiometric proportions and the reaction mixture refluxed in a solvent such as ethanol, acetonitrile, or toluene. The product, as the appropriate acid addition salt, is then neutralized by the addition of base such as aqueous potassium hydroxide. In situations where the amine is volatile, then the reaction mixture is heated, typically from 50° C. to 150° C., in a sealed tube.

Step e:

Conversion of the nitrile to the hydroxyamidine is achieved by allowing the nitrile to react with hydroxylamine in methanol at room temperature. Typically hydroxylamine hydrochloride is added to the nitrile containing substrate at room temperature, and the reaction is initiated by the addition of base such as potassium carbonate or diisopropylethylamine. The reaction is usually monitored by HPLC to determine the absence of starting material, the nitrile, and are typically complete within a 24-hour period.

Step f:

The amidoxime is activated by the addition of acetic anhydride of trifluoroacetic anhydride intermediate in a solvent such as acetic acid or trifluoroacetic acid to afford the O-acylated, which may be isolated or alternatively used directly in the subsequent reduction step. This step and the subsequent reduction may be combined, i.e., the reduction with Pd/C is performed in acetic anhydride/acetic acid, or trifluoroacetic anhydride/trifluoroacetic acid.

Alternatively, treatment of the nitrile with hydrogen chloride in an alcoholic solvent affords the corresponding iminoether hydrochloride. These intermediates are then treated with a source of ammonia, for example, ammonia in methanol, or ammonium chloride, or ammonium acetate, and the mixture is stirred and warmed, if necessary, to afford the amidine.

A procedure for preparing the compounds of Formula I, when the optional bond is present, is outlined in Scheme 2.

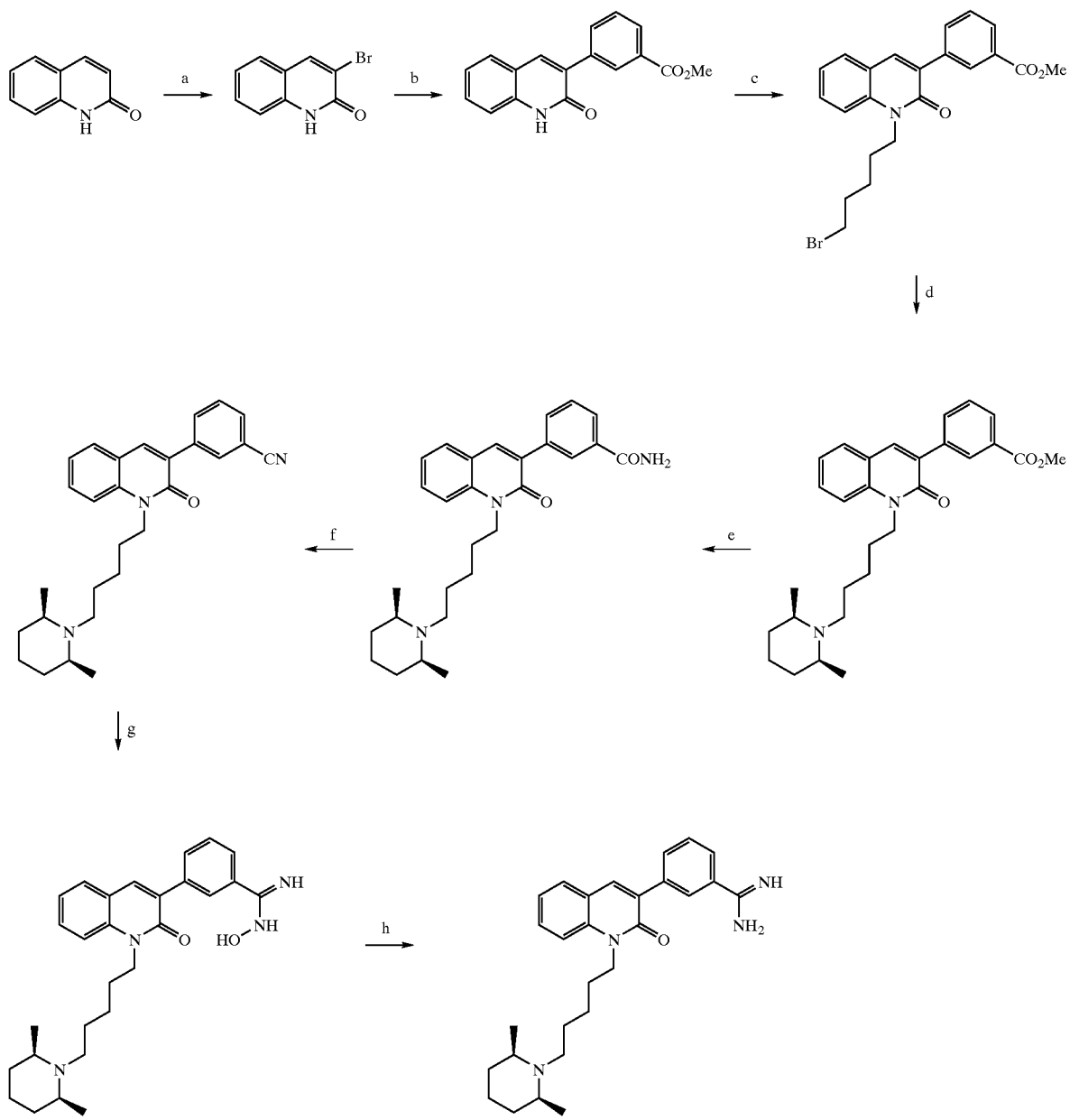

Step a:

Treatment of the 3,4-dihydro-quinolin-2-one with a strong base, such as BuLi and tetramethylpiperidine, affords after exchange with mercury (an) chloride and then addition of the 3-bromo derivative (see Fernandez et al., *Synthesis*, 1995:1362). Alternatively, the required 3-bromohydroquinolin-2-one is available from 3-bromoquinoline via its N-oxide according to the procedure of Leclerc et al., *J. Med. Chem.*, 1986:2427.

Step b:

A palladium cross-coupling reaction employing an aryl boronic acid, such as 3-(methoxycarbonyl)phenylboronic acid or aryl stannane, effects the transformation of the vinylic bromide to the corresponding aryl alkene. Typically, palladium (0) tetrakis triphenylphosphine is added to a mixture of the halide and aryl boronic acid in a solvent such as a mixture of toluene and DMF, and mixture is then warmed to about 100° C. under a nitrogen atmosphere. The procedure is analogous to that described by Timari et al., *Syn. Lett.*, 1997:1067. An alternative procedure employing aryl zinc halide organometalics has also been described by Leclerc et al., *J. Med. Chem.*, 1986:2427.

Alternatively, according to the procedure of Meng et al., *J. Het. Chem.*, 1991:1481, the vinyl halide may be irradiated with a mercury lamp in a quartz vessel in the presence of, for example, thiophene to afford the 3-(2-thienyl). Use of benzene as a solvent would afford the 3-phenyl adduct.

Step c:

Alkylation is typically achieved by treatment with an appropriate electrophile and by the addition of a base in a dipolar aprotic solvent. Typical conditions include, for example, use of a bis-electrophilic substrate such as 1,5-dibromopentane in a dipolar aprotic solvent such as DMF or DMSO and addition of a base, such as sodium hydride. Alternatively, alkylation can be achieved by the addition of a phase transfer reagent such as an alkylammonium salt, such as benzyltriethylammonium chloride, and employing a base such as sodium ethoxide. Reaction rates are typically improved by the application of heat and hence reactions are un at from 0° C. to 70° C.

Step d:

Treatment with an amine, such as cis-2,6-dimethylpiperidine at an elevated temperature such as 50° C., affords the expected N-alkylated piperidine. The amine may be used as solvent, or alternatively, the amine may be added in stoichiometric proportions and the reaction mixture refluxed in a solvent such as ethanol, acetonitrile, or toluene. In situations where the amine is volatile, then the reaction mixture is heated, typically from 50° C. to 150° C., in a sealed tube.

Step e:

Conversion of the methyl ester to the amide is achieved by addition of ammonium hydroxide to a solution of the ester in a solvent such as THF. The reaction mixture is stirred at room temperature for several hours, or alternatively, heated in a sealed tube. An alternative procedure for the transformation involves conversion of the ester to the corresponding carboxylic acid with aqueous sodium hydroxide and then conversion of the acid to the corresponding acid chloride with for example oxalyl chloride, catalytic DMF, in a solvent such as methylene chloride. Finally, the acid chloride is then treated with aqueous ammonia, which readily affords the amide.

Step f:

Addition of trichloroacetyl chloride and triethylamine to a solution of the amide in methylene chloride at 0° C. and then stirring with warming to room temperature over 1 hour readily affords the nitrile.

Steps g and h:

Conversion of the nitrile to the corresponding amidine is achieved according to the procedure in Scheme 1.

An alternative procedure to afford the required quinolinones proceeds according to the procedure of Chupp et al., *J. Het. Chem.*, 1979:65–71, and outlined in Scheme 3.

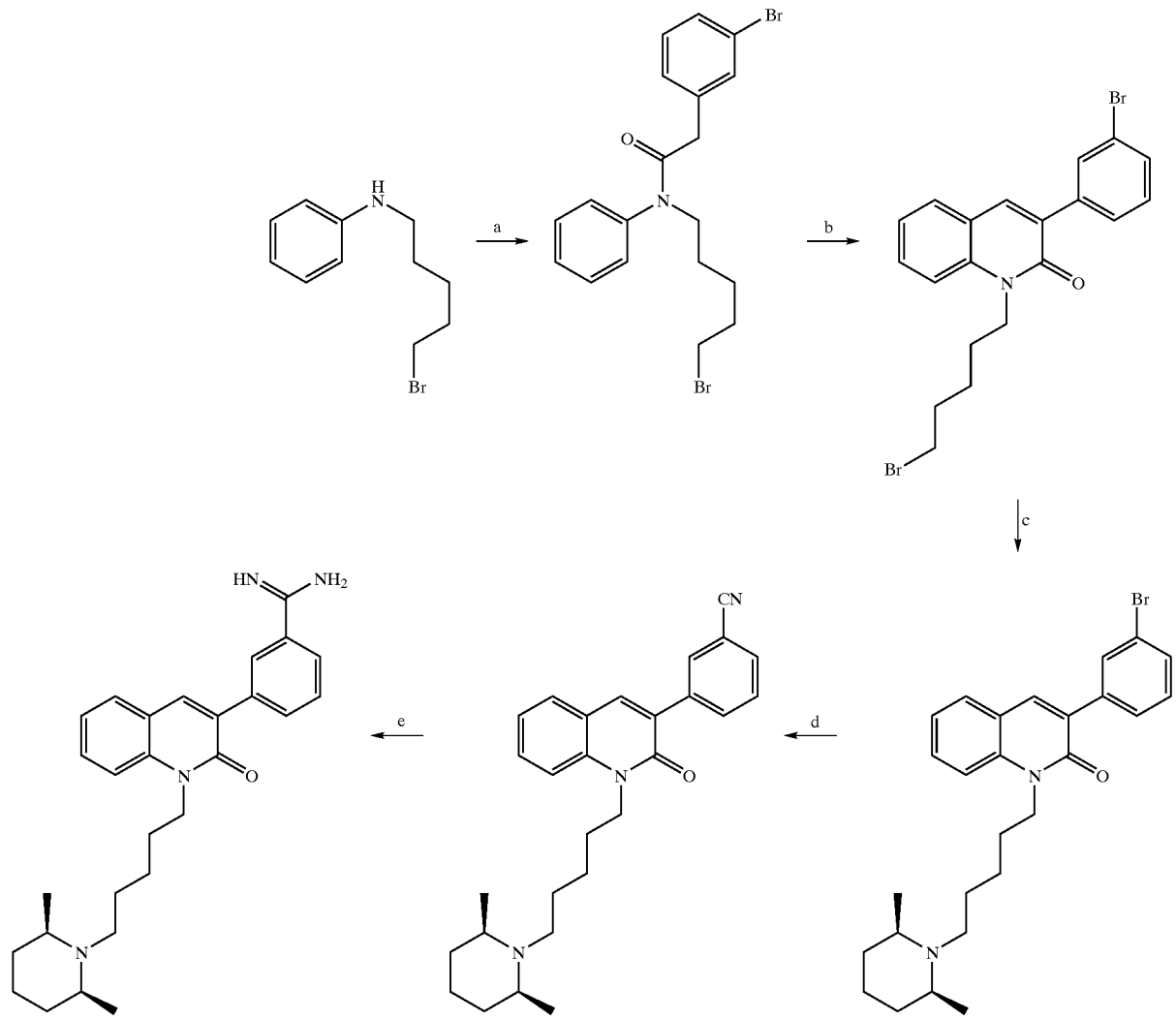

Step a:
The aniline is converted to the anilide by treatment with the appropriate arylacetyl chloride in a solvent such as methylene chloride.

Step b:
Treatment of the anilide with Vilsmier reagent, prepared from DMF and phosphoryl chloride in methylene chloride, affords after refluxing the appropriate quinolinone.

Step c:
Treatment with an amine, such as cis-2,6-dimethylpiperidine at an elevated temperature such as 50° C. affords the expected N-alkylated piperidine. The amine may be used as solvent, or alternatively, the amine may be added in stoichiometric proportions and the reaction mixture refluxed in a solvent such as ethanol, acetonitrile or toluene. In situations where the amine is volatile, then the reaction mixture is heated, typically from 50° C. to 150° C., in a sealed tube.

Step d:
The aryl bromide is converted to the corresponding nitrile by, for example, treatment with copper cyanide in a solvent such as DMF. Typically, the reaction mixture is warmed to 160° C. and maintained at this temperature for several hours, typically 12, to afford the required product. Alternatively, the bromide, or iodide, or triflate is converted to the nitrile by treatment with a transition metal, such as palladium tetrakis triphenylphosphine and zinc cyanide. The mixture is then warmed in a solvent such as DMF, typically to a temperature of 80° C. for several hours or until the reaction is judged complete by, for example, TLC.

Step e:
The nitrile can be converted to the amidine by a number of procedures. Two useful procedures include: conversion of the nitrile to the hydroxyamidine which is achieved by allowing the nitrile to react with hydroxylamine in methanol at room temperature. Typically, hydroxylamine hydrochloride is added to the nitrile containing substrate at room temperature, and the reaction is initiated by the addition of base such as potassium carbonate or diisopropylethylamine. The amidoxime may be reduced directly to the amidine, but is typically activated by the addition of acetic anhydride of trifluoroacetic anhydride to afford the O-acylated, or O-trifluoroacetyl, intermediate, which may be isolated or alternatively used directly in the subsequent reduction step. The reduction with Pd/C is performed in acetic anhydride/acetic acid, or trifluoroacetic anhydride/trifluoroacetic acid.

Alternatively, the nitrile may be treated with anhydrous HCl in an alcoholic solvent such as methanol to afford the imino ether hydrochloride. This intermediate is then treated with a source of ammonia to afford the expected amidine. Typical sources of ammonia include ammonia in methanol or ammonium acetate and ammonium chloride.

Scheme 4 represents an alternative procedure for preparing the requisite compounds of Formula I. It is particularly useful for introducing heterocyclic functionality at C-3.

Scheme 4

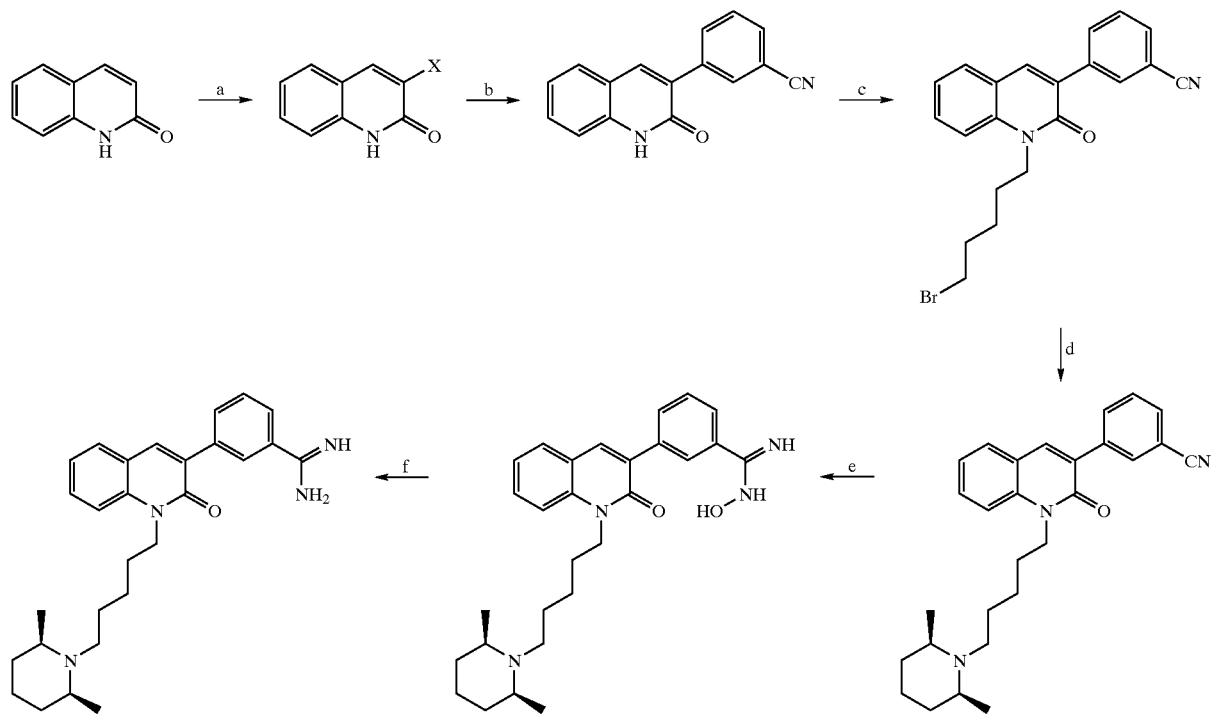

Step a:
Treatment of hydroquinolin-2-one with strong base, such as butyl lithium, and then tributylstannyl chloride, or hexabutyldistannane, readily affords the corresponding 3-stannyl quinolin-2-one.

Step b:
Addition of the stannane to a solution of 3-bromobenzonitrile in a solvent such as THF, DMF, toluene, or dioxane and in the presence of palladium, such as Pd(PPh$_3$)$_2$Cl$_2$, or Pd(PPh$_3$)$_4$ with the application of heat such as reflux, affords the 3-aryl (or 3-heteroaryl adduct in the case of a halo substituted heterocycle).

Steps c–f:

Typical procedures for these transformations are available in the above schemes.

The substituted acetic acid derivatives used in these reactions are prepared by a number of standard procedures. For example, substituted benzoic acids or benzoylchlorides may be elaborated according to Scheme 5.

Scheme 5

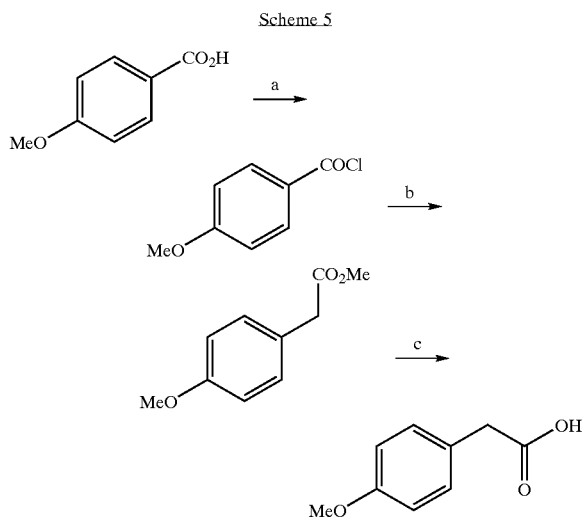

Step a:

The substituted benzoic acid is converted to the corresponding acid chloride with, for example, oxalyl chloride and catalytic DMF in a solvent such as methylene chloride at 0° C. to room temperature over a period of several hours, such as 1 to 4 hours.

Step b:

Addition of ethereal diazomethane to the acid chloride in, for example, ether at about 5° C. The mixture is then stirred for 1 hour at room temperature in which, in advantageous situations, the acid chloride typically goes into solution and the intermediate diazo species precipitates from solution. Rearrangement with silver oxide, freshly prepared from silver nitrate and aqueous sodium hydroxide in an alcoholic solvent such as methanol at reflux, affords the acetic acid methyl ester. During the reaction, loss of nitrogen is observed as effervescence and a silver mirror forms. Replacement of methanol with water affords the corresponding acid.

Step c:

Conversion of the methyl ester is performed by the addition of aqueous base, such as lithium hydroxide, in a solvent such as THF/methanol/water and stirring the reaction mixture at room temperature for several hours.

Compounds of the present invention are further characterized by their ability to inhibit the catalytic activity of factor Xa, which is demonstrated in the assay as follows. Compounds of the present invention may be prepared for assay by dissolving them in buffer to give solutions ranging in concentrations from 1 to 100 $\mu$M. In an assay to determine the inhibitory dissociation constant, Ki, for a given compound, a chromogenic or fluorogenic substrate of factor Xa would be added to a solution containing a test compound and factor Xa; the resulting catalytic activity of the enzyme is spectrophotometrically determined. This assay is well-known to those skilled in the art and is commonly used to determine antithrombotic activity.

The compounds of the present invention may be used as anti-coagulants in vitro or ex vivo as in the case of contact activation with foreign thrombogenic surfaces such as is found in tubing used in extracorporeal shunts. The compounds of the invention may also be used to coat the surface of such thrombogenic conduits. To this end, the compounds of the invention can be prepared as lyophilized powders, redissolved in isotonic saline or similar diluent, and added in an amount sufficient to maintain blood in an anticoagulated state.

The therapeutic agents of the present invention may be administered alone or in combination with pharmaceutically acceptable carriers. The proportion of each carrier is determined by the solubility and chemical nature of the compound, the route of administration, and standard pharmaceutical practice. For example, the compounds may be injected parenterally; this being intramuscularly, intravenously, or subcutaneously. For parenteral administration, the compound may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may also be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and/or flavoring agents. Typical formulations will contain from about 5 to 95 percent by weight of an invention compound.

The amount of invention compound to be utilized to prevent and treat thrombotic disorders is that amount which is effective to prevent or treat the condition without causing unacceptable side effects. Such effective amounts will be from about 0.01 mg/kg to about 500 mg/kg, preferably from about 1 mg/kg to about 100 mg/kg. Physicians will determine the precise dosage of the present therapeutic agents which will be most suitable. Dosages may vary with the mode of administration and the particular compound chosen. In addition, the dosage may vary with the particular patient under treatment.

When the composition is administered orally, a larger quantity of the active agent will typically be required to produce the same effect as caused with a smaller quantity given parenterally.

To further assist in understanding the present invention, the following non-limiting examples of such factor Xa inhibitory compounds are provided. The following examples, of course, should not be construed as specifically limiting the present invention, variations presently known or later developed, which would be within the purview of one skilled in the art and considered to fall within the scope of the present invention as described herein. The preferred compounds as of the present invention are synthesized using conventional preparative steps and recovery methods known to those skilled in the art of organic and bio-organic synthesis, while providing a new and unique combination for the overall synthesis of each compound. Preferred synthetic routes for intermediates involved in the synthesis, as well as the resulting anti-thrombotic compounds of the present invention, follow.

EXAMPLES

In general, evaporation of reaction mixtures were carried out by rotary evaporation in vacuo at room temperature 18° C. to 25° C. or at elevated temperatures up to 50° C.

Chromatography, preferably by medium pressure liquid chromatography, were generally performed on Merck Kieselgel. Reverse phase purification via high pressure liquid chromatography (HPLC), for particular polar compounds, was performed on C-18 reverse phase silica gel employing a gradient elution of water and acetonitrile containing 0.1% trifluoroacetic acid. The final products displayed nuclear magnetic resonance (NMR) spectra and mass spectra consistent with their assigned structure. Intermediates were not typically fully characterized, and their purity was routinely assessed by HPLC or thin layer chromatography.

Example 1

1-[5(2,6-Dimethylpiperidino)pentyl]-3-(4-methoxyphenyl)-1,2,3,4-tetrahydro-2-quinolinone Step (a) Preparation of: (E)-2-(4-Methoxyphenyl)-3-(2-nitrophenyl)-2-propanoic acid

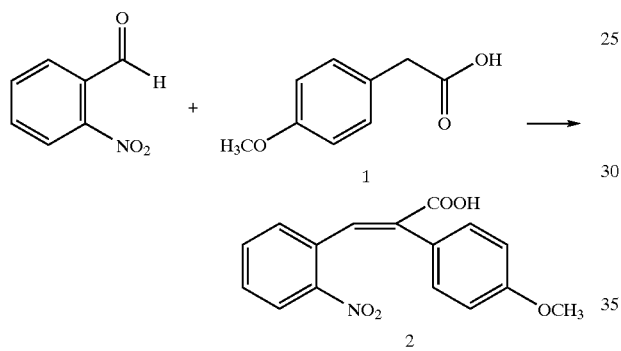

Into a mixture of o-nitrobenzaldehyde (6.19 g, 41.0 mmol) and 4-methoxyphenylacetic acid (1) (10.02 g, 60.3 mmol) in acetic anhydride (20 mL) was added triethylamine (5.66 mL, 41.0 mmol), and the reaction mixture was stirred and heated at reflux (150° C.) for 15 minutes. The solution was cooled, diluted with water, and extracted with ethyl acetate (3×200 mL). The combined organic extracts were washed with brine (2×100 mL), dried with magnesium sulfate, filtered, evaporated in vacuo, and dried under high vacuum to give 16.20 g as an orange solid. The product (2) was crystallized from ethyl acetate in hexane to give 10.21 g (87%) as a solid.

$^1$H NMR (DMSO, 300 M): δ 8.06 (1H, m), 7.91 (1H, s), 7.47 (3H, m), 6.97 (2H, d, J=8.78 Hz), 6.76 (2H, d, J=8.97 Hz), 3.68 (3H, s).

Step (b) Preparation of: 3-(4-Methoxyphenyl)-1,2,3,4-tetrahydro-2-quinolinone

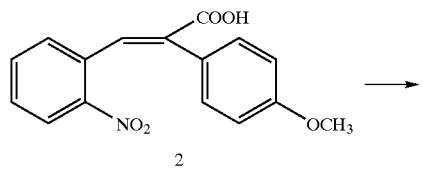

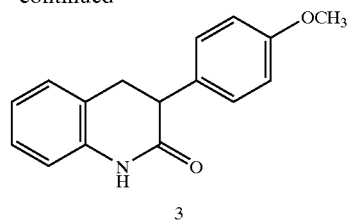

To (2) (8.22 g, 28.6 mmol) in methanol (100 mL) was added 20% palladium on carbon (1.0 g) and hydrogenated at 23° C. for 3 hours. The mixture was filtered through celite and the filter pad washed with THF and DMF. The combined filtrate and washings were concentrated in vacuo. The product (3) was crystallized from methanol in water to give 6.4 g (88%) as a solid.

$^1$H NMR (DMSO, 300 M): δ 10.26 (1H, s), 7.14 (4H, m), 6.84 (4H, m), 3.69 (3H, s), 3.32 (1H, s), 3.11 (2H, d, J=7.69 Hz).

Step (c) Preparation of: 1-(5-Bromopentyl)-3-(4-methoxyphenyl)-1,2,3,4-tetrahydro-2-quinolinone

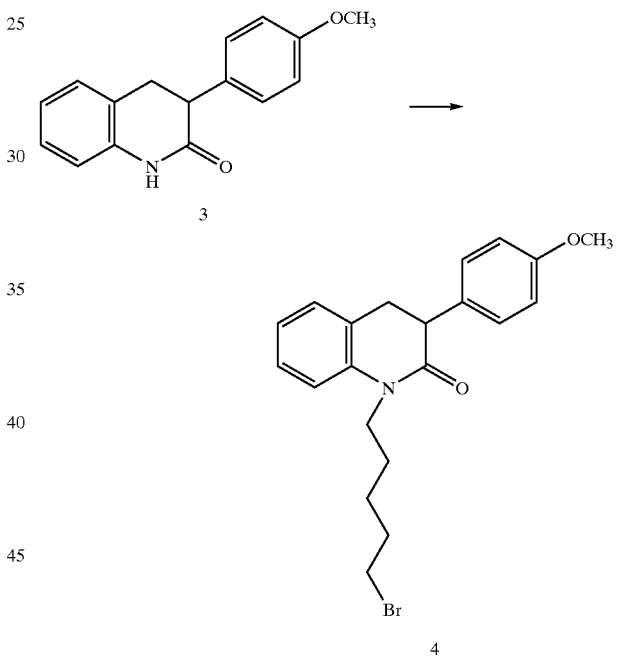

To the quinolinone (3) (2.02 g, 7.98 mmol) in DMF (10 mL) was added sodium hydride (0.35 g, 8.75 mmol), and the solution was stirred at 70° C. for fit 15 minutes until bubbling stopped. To this solution was added 1,5-dibromopentane (4.37 mL, 31.9 mmol), and the solution was stirred at 70° C. for additional 12 hours. The solution was cooled, diluted with water, and extracted with ethyl acetate (4×200 mL). The combined organic extracts were washed with brine (2×100 mL), dried with magnesium sulfate, filtered, and evaporated in vacuo. The residue was purified on a silica gel column eluted with 20% to 40% ethyl acetate in hexane. The product (4) was isolated 2.43 g (76%) as a yellow oil.

$^1$H NMR (DMSO, 300 M): δ 7.26–6.94 (6H, in), 6.80 (2H, d, J=7.69 Hz), 3.91–3.78 (2H, m), 3.67 (3H, s), 3.50 (2H, m), 3.33 (1H, s), 3.12 (2H, d, J=6.78 Hz), 1.81 (2H, m), 1.57 (2H, m), 1.41 (2H, m).

Step (d) Preparation of: 1-[5-(2,6-Dimethylpiperidino)pentyl]-3-(4-methoxyphenyl)-1,2,3,4-tetrahydro-2-quinolinone

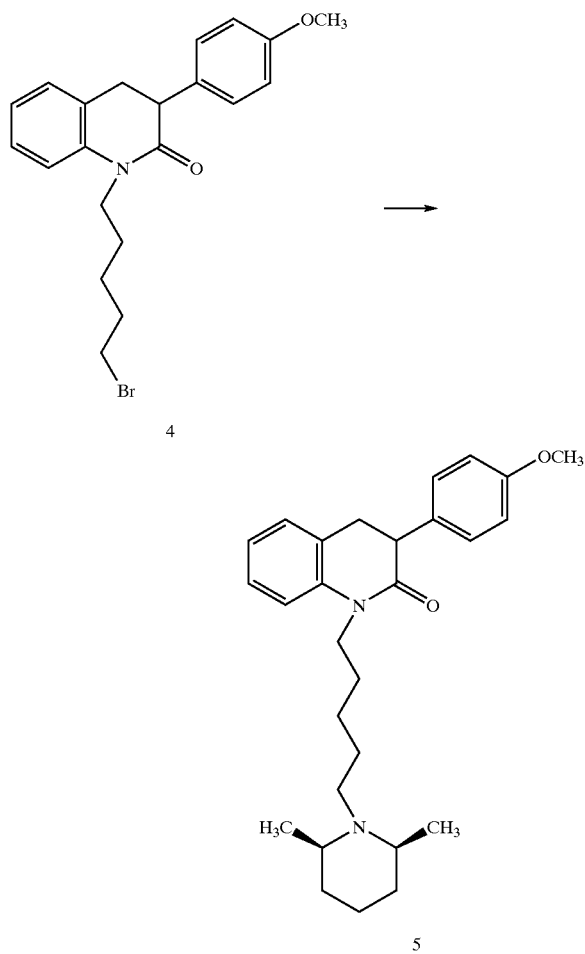

To (4) (0.32 g, 0.795 mmol) was added cis-2,6-dimethylpiperidine (6.2 mL, 46.0 mmol), and the solution was stirred at 70° C. for 48 hours. The solution was cooled, diluted with water, and extracted with ethyl acetate (3×100 mL). The combined organic extracts were washed with saturated sodium bicarbonate (2×100 mL), washed with brine (2×100 mL), dried with magnesium sulfate, filtered, and evaporated in vacuo. The residue was purified by preparative HPLC (Vydac 218TP 1022 C18, eluted with a mixture of solvents consisting of (i) 0.1% trifluoroacetic acid in water, and (ii) 0.1% trifluoroacetic acid in acetonitrile, gradient profile 95:5 (i):(ii) to 60:40 (i):(ii) over 90 minutes, flow rate 20 mL/minute, λ=214 nM) and was lyophilized to give 276 mg (78%) of product (5) as an oil.

$^1$H NMR (DMSO, 400 MHz): δ 7.28–6.98 (6H, m), 6.82 (2H, d, J=8.68 Hz), 3.99–3.81 (4H, m), 3.70 (3H, s), 3.24–3.15 (3H, m), 1.86–1.29 (14H, m), 1.24 (6H, m). CI MS M+1=437. HPLC: RT=14.4 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Example 2

3-(1-5-[(2R,6S)-2,6-dimethyltetrahydro-1(2H)-pyridinyl]pentyl-2-oxo-1,2,3,4-tetrahydro-3-quinolinyl)-4-hydroxybenzenecarboximidamide Step (a) Preparation of: 3-[(E)-(2-nitrophenyl)methylidene]-1-benzofuran-2-one

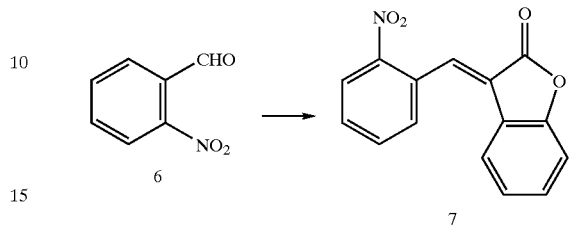

Ortho-hydroxyphenylacetic acid (1.835 g, 0.012 mmol) was added to a mixture of ortho-nitrobenzaldehyde (1.835 g, 0.012 mmol), acetic anhydride (10 mL) and triethylamine (1.7 mL, 0.012 mol), and then the mixture was heated at 140° C. for 15 minutes. The mixture was allowed to cool to 80° C., at which point water (10 mL) was carefully added. The precipitated material was washed with methanol and dried to afford the required product (7) (0.905 g, 28%). A further amount of product (1.523 g) was recovered from the filtrate.

$^1$H NMR (DMSO, 400 MHz): δ 8.36 (1H, d, J=8.3 Hz), 8.15 (1H, s), 8.0–7.8 (3H, m), 7.42 (1H, t, J=7.0 Hz), 7.31 (1H, d, J=7.5 Hz), 7.04 (2H, m).

APCI MS 267.

Step (b) Preparation of: 3-(2-hydroxyphenyl)-3,4-dihydro-2(1H)-quinolinone

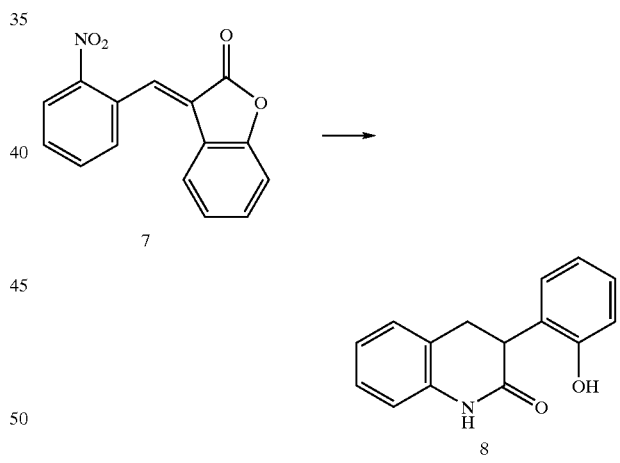

To 3-[(E)-(2-nitrophenyl)methylidene]-1-benzofuran-2-one (7) (2.18 g, 7.65 mmol) in methanol (70 mL) and THF (30 mL) was added Pd/C 20% (0.050 g) and the mixture hydrogenated for 5 hours. Filtration and chromatography, eluant 30% EtOAc to 50% EtOAc in hexane, afforded the required product (8) (0.913 g, 49%).

$^1$H NMR (DMSO, 300 MHz): δ 9.52 (1H, s), 7.15 (2H, m), 7.05 (1H, m), 6.97 (1H, m), 6.89 (2H, d, J=7.3 Hz), 6.83 (1H, d, J=7.9 Hz), 6.67 (1H, t, J=7.3 Hz), 3.96 (1H, dd, J=10.4 Hz, 6.4 Hz), 3.19 (1H, dd, J=15.8 Hz, 10.6 Hz), 2.99 (1H, dd, J=15.8 Hz, 10.6 Hz).

APCI MS 240.

Analysis $C_{15}H_{13}N_1O_2$: Required: C, 75.30; H, 5.48; N, 5.85. Found: C, 74.95; H, 5.51; N, 5.61.

Step (c) Preparation of: 3-(5-bromo-2-hydroxyphenyl)-3,4-dihydro-2(1H)-quinolinone

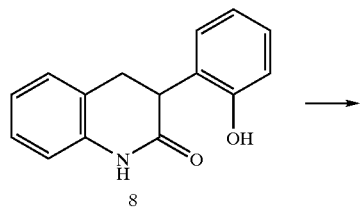
8

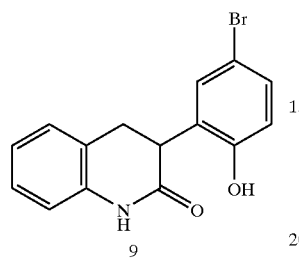
9

To 3-(2-hydroxyphenyl)-3,4-dihydro-2(1H)quinolinone (8) (0.650 g, 2.72 mmol) in carbon disulphide (10 mL) and methylene chloride (10 mL) was slowly added (110 minutes) a solution of bromine (0.17 mL, 3.30 mmol) in carbon disulphide (5 mL). After 2 hours a precipitate had fully formed which was collected and washed with ether (2×10 mL). This afforded the required product (9) (0.738 g, 85%).

$^1$H NMR (DMSO, 400 MHz): δ 10.29 (1H, s), 7.21 (2H, m), 7.16 (2H, m), 6.91 (2H, m), 6.78 (1H, d, J=8.5 Hz), 3.93 (1H, dd, 3=12.0 Hz, 6.4 Hz), 3.19 (1H, dd, J=15.4 Hz, 12.1 Hz), 2.97 (1H, dd, J=15.4 Hz, 6.3 Hz).

APCI MS 318/320.

Step (d) Preparation of: 3-[2-(benzyloxy)-5-bromophenyl]-3,4-dihydro-2-(1H)-quinolinone

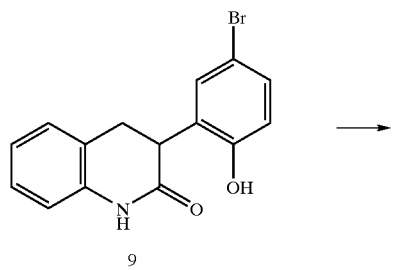
9

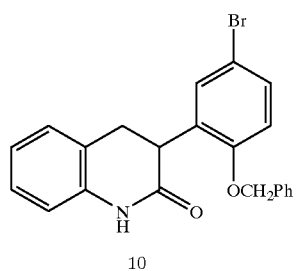
10

To 3-(5-bromo-2-hydroxyphenyl)-3,4-dihydro-2(1H)-quinolinone (9) (3.16 g, 9.94 mmol) in DMF (15 mL) was added cesium carbonate (5.2 g, 31 mmol) and then benzyl bromide (1.18 mL, 9.92 mmol). The mixture was stirred at room temperature for 16 hours, diluted with ethylacetate (200 mL), washed with brine (100 mL), and then dried over MgSO$_4$. Chromatography, silica gel, eluant 20% EtOAc in hexane, affords the required product (10) (2.77 g, 68%).

$^1$H NMR (CDCl$_3$, 300 MHz): δ 8.40 (1H, brs), 7.30 (7H, m), 7.17 (1H, d, J=7.5 Hz), 7.11 (1H, d, J=7.5 Hz), 6.98 (1H, t, J=6.3 Hz), 6.84 (1H, d, J=8.3 Hz), 6.78 (1H, d, J=7.9 Hz), 5.07 (2H, s), 4.09 (1H, dd, J=13.2 Hz, 6.6 Hz), 3.38 (1H, dd, J=15.2 Hz, 13.2 Hz), 2.99 (1H, dd, J=15.8 Hz, 6.6 Hz).

APCI MS 408/410.

Step (e) Preparation of: 4-(benzyloxy)-3-(2-oxo-1,2,3,4-tetrahydro-3-quinolinyl)benzenecarbonitrile

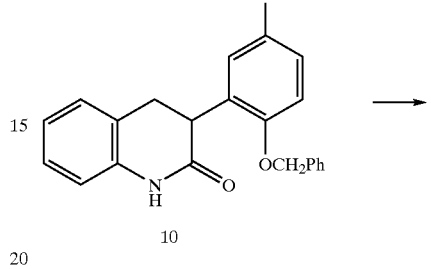
10

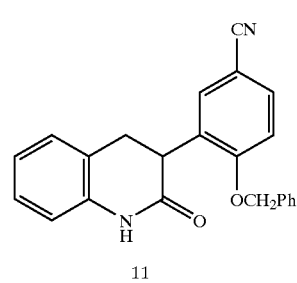
11

To 3-[2-(benzyloxy)-5-bromophenyl]-3,4-dihydro-2(1H)-quinolinone (10) (2.77 g, 6.79 mmol) in DMF (8 mL) was added copper (I) cyanide (2.7 g, 30 mmol), and then the mixture was heated at an oil bath temperature of 160° C. for 16 hours. The mixture was cooled, diluted with ethylacetate (200 mL), and washed with aqueous NH$_4$OH (2×°100 mL). After washing with brine (2×100 mL) and drying over MgSO$_4$, the product was isolated by chromatography, silica gel eluant 30% ethylacetate to 50% ethylacetate in hexane, to afford (11) (1.077 g, 45%).

$^1$H NMR (DMSO, 300 MHz): δ 10.40 (1H, s), 7.77 (1H, dd, J=8.4 Hz, 2.0 Hz), 7.69 (1H, d, J=2.2 Hz), 7.40–7.1 (8H, m), 6.89 (2H, m), 5.22 (2H, m), 4.04 (1H, dd, J=13.5 Hz, 6.6 Hz), 3.31 (1H, dd, J=15.7 Hz, 13.2 Hz), 2.93 (1H, dd, J=15.7 Hz, 6.6 Hz).

APCI MS 355.

Step (f) Preparation of: 4-(benzyloxy)-3-[1-(5-bromopentyl)-2-oxo-1,2,3,4-tetrahydro-3-quinolinyl]benzenecarbonitrile

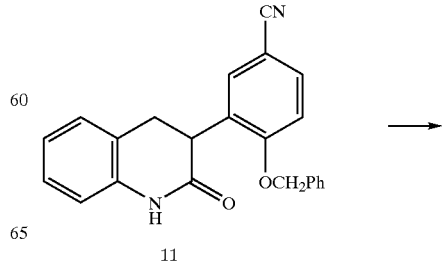
11

-continued

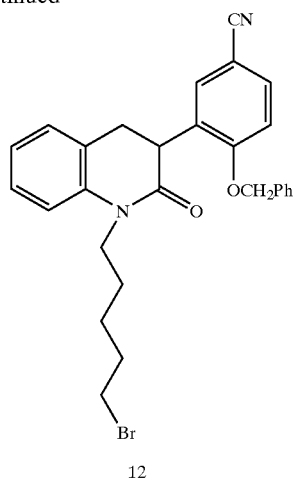

12

To 4-(benzyloxy)-3-(2-oxo-1,2,3,4-tetrahydro-3-quinolinyl)-benzenecarbonitrile (11) (0.270 g, 0.76 mmol) in DMF (3 mL) was added sodium hydride (60% in oil) (0.035 g, 0.9 mmol) and 1,5-dibromopentane (0.5 mL, 3.67 mmol), and then the solution was stirred for 1 hour. The solution was diluted with 1 N HCl (10 mL) and extracted with ethyl acetate (2×100 mL). The combined organic extracts were washed with brine (2×100 mL), dried with magnesium sulfate, filtered, and evaporated in vacuo. The residue was purified on a silica gel column eluted with 20% ethyl acetate in hexane. The product (12) was isolated 0.230 g (60%) as an oil.

$^1$H NMR (CDCl$_3$, 300 MHz): δ 7.57 (1H, dd, J=8.6 Hz, 2.0 Hz), 7.42 (1H, d, J=2.0 Hz), 7.40–7.2 (6H, m), 7.13 (1H, d, J=6.4 Hz), 7.02 (3H, m), 5.15 (2H,m), 4.04 (1H, dd, J=12.9 Hz, 5.9 Hz), 3.98 (2H, m), 3.39 (2H, t, J=6.6 Hz), 3.30 (1H, dd, J=15.4 Hz, 12.9 Hz), 2.96 (1H, dd, J=15.4 Hz, 5.9 Hz), 1.88 (2H, m), 1.75–1.45 (4H, m).

APCI MS 503/505.

Step (g) Preparation of: 3-(1-5-[(2R,6S)-2,6-dimethyltetrahydro 1(2H)-pyridinyl]pentyl-2-oxo-1,2,3,4-tetrahydro-3-quinolinyl)$_4$ hydroxybenzenecarboximidamide

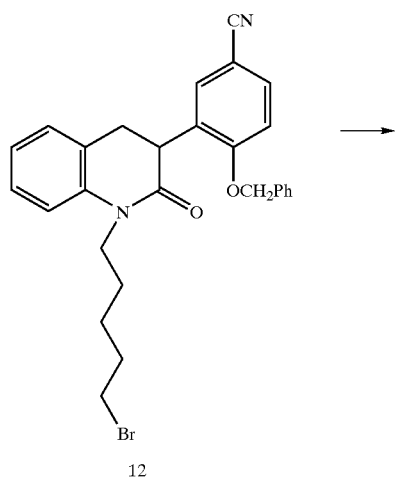

12

→

-continued

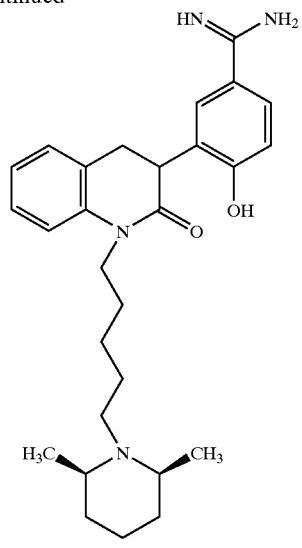

13

To (12) 4-(benzyloxy)-3-[1-(5-bromopentyl)-2-oxo-1,2,3,4-tetrahydro-3-quinolinyl]benzenecarbonitrile (0.23 g, 0.457 mmol) was added cis-2,6-dimethylpiperidine (5 mL, 37.0 mmol), and the solution was stirred at 70° C. for 48 hours. The mixture was evaporated in vacuo. HPLC: RT=18.06 min. (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

This mixture was dissolved in ethanol (10 mL) and treated with hydroxyl amine hydrochloride (0.70 g, 10 mmol) and diisopropylethylamine (1.8 mL, 10 mmol). After stirring for 24 hours, the reaction mixture was evaporated and HPLC indicated the reaction was complete to afford 4-(benzyloxy)-3-(1-5-[(2R,6S)-2,6-dimethyltetrahydro-1 (2H)-pyridinyl]pentyl-2-oxo-1,2,3,4-tetrahydro-3-quinolinyl)-N-hydroxybenzenecarboximidamide RT=12.37 min. (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

To this mixture was added trifluoroacetic acid (5 mL) and trifluoroacetic anhydride (1 mL). After 2 hours the reaction mixture was evaporated and HLPC indicated the reaction was complete RT=21.5 min. (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

The residue was redissolved in trifluoroacetic acid (10 mL) and treated with Pd/C 20% (0.05 g) and hydrogenated for 16 hours. The mixture was filtered through celite, treated with water 1 mL, and then evaporated. The residue was purified by preparative HPLC (Vydac 218TP 1022 C18, eluted with a mixture of solvents consisting of (i) 0.1% trifluoroacetic acid in water, and (ii) 0.1% trifluoroacetic acid in acetonitrile, gradient profile 95:5 (i):(ii) to 60:40 (i):(ii) over 90 minutes, flow rate 20 mL/minute, λ=214 nM), converted to the HCl salt by ion exchange chromatography, and then lyophilized to give 3-(1-5-[(2R,6S) 2,6-dimethyltetrahydro-1(2H)-pyridinyl]pentyl-2-oxo-1,2,3,4-tetrahydro-3-quinolinyl)₄-hydroxybenzenecarboximidamide dihydrochloride (0.123 g, 50%) of product (13) as a powder.

CI MS M+1=463.

HPLC: RT=10.1 min. (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

¹H NMR (DMSO, 400 MHz): δ 10.89 (1H, s), 10.2 (1H, brs), 9.09 (2H, s), 8.8 (1H, s), 7.62 (2H, m), 7.20 (3H, m), 7.0 (2H, in), 3.90 (3H, in), 3.40 (1H in), 3.20 (2H, m), 3.00 (1H, m), 2.85 (2H, m), 1.80–1.2 (18H, in).

APCI MS 463.

Example 3
3-(1-5-[(2R,6S)2,6-dimethyltetrahydro-[(2H)-pyridinyl]pentyl-2-oxo-1,2,3,4-tetrahydro-3-quinolinyl) benzenecarboximidamide Step (a) Preparation of: (E)-2-(3-hydroxyphenyl)-32-nitrophenyl)-2-propenoic acid

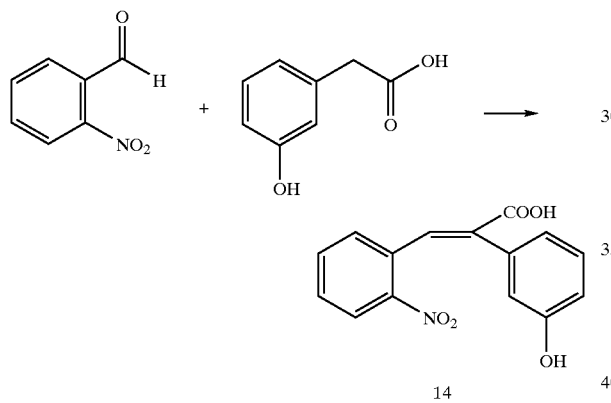

Into a mixture of o-nitrobenzaldehyde (19.22 g, 127 mmol) and 3-hydroxyphenylacetic acid (19.30 g, 127 mmol) in acetic anhydride (87 mL) was added triethylamine (17.5 mL, 126 mmol), and the reaction mixture was stirred and heated at reflux (150° C.) for 45 minutes. The solution was diluted with water (200 mL), cooled, diluted 2N NaOH (200 mL), and washed with ether. The aqueous solution was then acidified with 6N HCl to pH 3 and stirred for 3 hours. The solid was collected and dried under high vacuum at 45° C. to give 23.15 g (64%) of the required product (14).

¹H NMR (DMSO, 300 MHz): δ 8.09 (1H, m), 7.93 (1H, s), 7.48 (2H, in), _7.00 (2H, m), 6.59 (1H, in), 6.48 (2H, m).

CI MS M+1=285.

Step (b) Preparation of: 3-(3-hydroxyphenyl)-3,4-dihydro-2 (1H)quinolinone

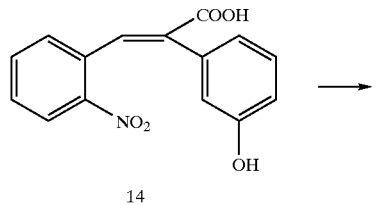

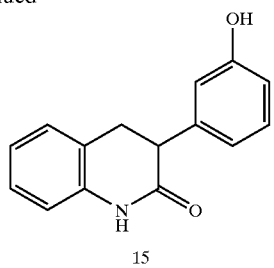

To (E)-2-(3-hydroxyphenyl)-3-(2-nitrophenyl)-2-propenoic acid (14) (26.29 g, 92.0 mmol) in methanol (600 mL) was added 20% palladium on carbon (1.5 g), and the mixture was hydrogenated at 45 PSI of H₂ at 30° C. for 3.5 hours. The mixture was filtered through celite and the filter pad washed with MeOH. The combined filtrate and washings were concentrated in vacuo. The product (15) was crystallized from methanol in water to give 17.95 g (82%) as a solid.

¹H NMR (DMSO, 400 MHz): δ 10.30 (1H, s), 9.31 (1H, s), 7.14 (2H, m), 7.05 (1H, m), 6.90 (2H, m), 6.61 (3H, m), 3.70 (1H, m), 3.20–3.06 (2H, m).

Step (c) Preparation of 3-(2-oxo-12,3,4-tetrahydro-3-quinolinyl)phenyl trifluoromethanesulfonate

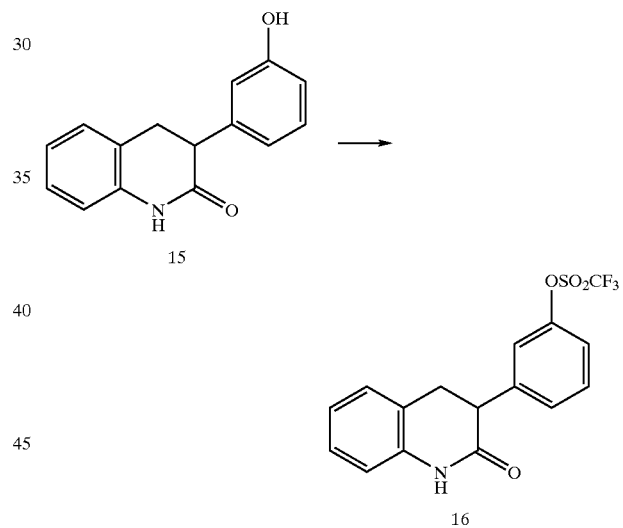

To 3-(3-hydroxyphenyl)-3,4-dihydro-2(1H)-quinolinone (15) (3.01 g, 12.6 mmol) in THF (40 mL) was added sodium hydride (0.55 g, 13.8 mmol), and the solution was stirred at room temperature for 5 minutes. To this solution was added N-phenyltrifluoromethanesulfonimide (4.92 g, 13.8 mmol), and the solution was stirred at room temperature for 1 hour. The solution was cooled, diluted with water, and extracted with ethyl acetate (3×200 mL). The combined organic extracts were washed with brine (2×100 mL), dried with magnesium sulfate, filtered, and evaporated in vacuo. The residue was purified on a silica gel column eluted with 20% to 40% ethyl acetate in hexane. The product (16) was isolated 4.29 g (92%) as a yellow solid.

¹H NMR (CDCl₃, 400 MHz): δ 8.06 (1H, s), 7.40–7.15 (6H, bm), 7.00 (1H, m), 6.76 (1H, m), 3.87 (1H, m), 3.22 (2H, m).

CI MS M+1=372.

Step (d) Preparation of: 3-(2-oxo-1,2,3,4-tetrahydro-3 quinolinyl)benzenecarbonitrile

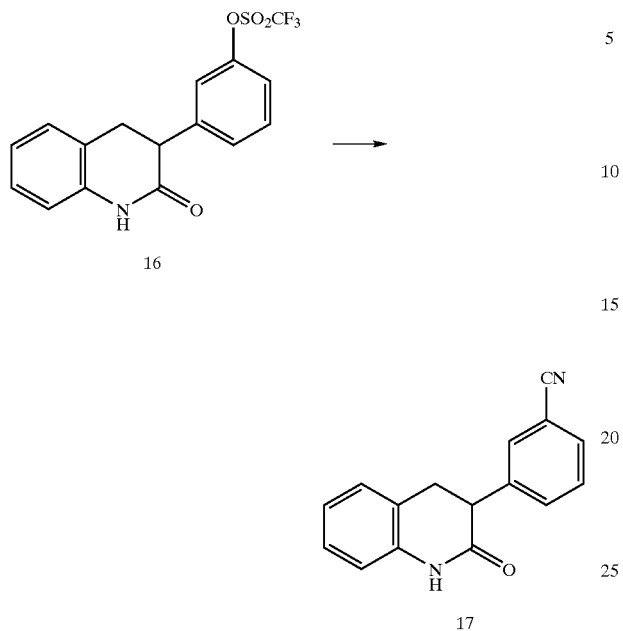

To 3-(2-oxo-1,2,3,4-tetrahydro-3-quinolinyl)phenyl trifluoromethanesulfonate (16) (0.410 g, 1.11 mmol) in DMF (5 mL) were added zinc cyanide (0.078 g, 0.690 mmol) and tetrakis(triphenylphosphine)palladium(0) (0.128 g, 0.11 mmol). The reaction mixture was stirred and heated at 100° C. for 1 hour. The solution was cooled, diluted with water (200 mL) and 2 M sulfuric acid (20 mL), and extracted with ethyl acetate (3×200 mL). The combined organic extracts were washed with brine (2×100 mL), dried with magnesium sulfate, filtered, and evaporated in vacuo. The product (17) was crystallized from hexane and ethyl acetate to give (0.222 g, 81%) as a solid.

$^1$H NMR (CDCl$_3$, 300 MHz): δ 8.23 (1H, s), 7.70–7.18 (6H, bm), 7.04 (1H, m), 6.81 (1H, m), 3.89 (1H, m), 3.24 (2H, in).

CI MS M+1=249.

Step (e) Preparation of: 3-[1-(5-bromopentyl)-2-oxo-1,2,3,4-tetrahydro-3-quinolinyl]benzenecarbonitrile

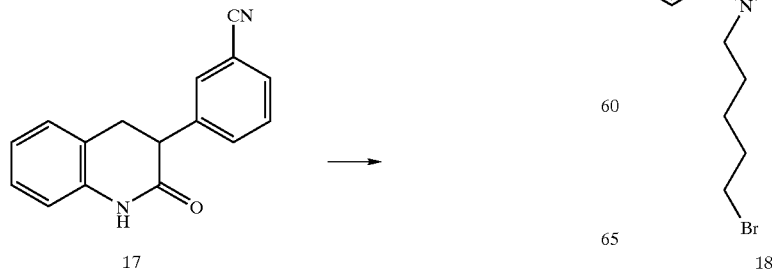

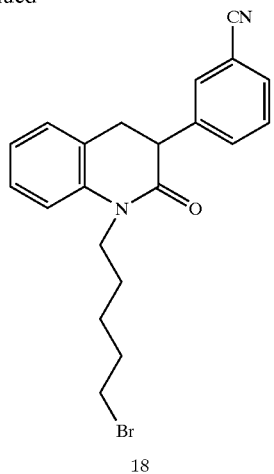

To 3-(2-oxo-1,2,3,4-tetrahydro-3-quinolinyl)benzenecarbonitrile (17) (2.76 g, 11.1 mmol) in DMF (15 mL) at 0° C. were added 1,5-dibromopentane (10.22 g, 44.4 mmol) and sodium hydride (0.48 g, 12.0 mmol), and the solution was stirred at this temperature for 3 hours. The solution was diluted with water and extracted with ethyl acetate (3×200 mL). The combined organic extracts were washed with brine (2×100 mL), dried with magnesium sulfate, filtered, and evaporated in vacuo. The residue was purified on a silica gel column eluted with 20% ethyl acetate in hexane. The product (18) was isolated 1.59 g (36%) as a yellow oil.

$^1$H NMR (CDCl$_3$, 300 MHz): δ 7.58–7.28 (5H, bm), 7.20 (1H, m), 7.05 (2H, m), 3.99 (2H, m), 3.85 (1H, m), 3.41 (2H, m), 3.19 (2H, m), 1.91 (2H, m), 1.70 (2H, m), 1.54 (2H, m).

CI MS M+1=397/399, M−1=395/396.

Step (f) Preparation of: 31−5-[(2R,6S)2,6-dimethyltetrahydro-t(2H)-pyridinyl]pentyl-2-oxo-1,2,3,4-tetrahydro-3-quinolinyl)benzenecarbonitrile

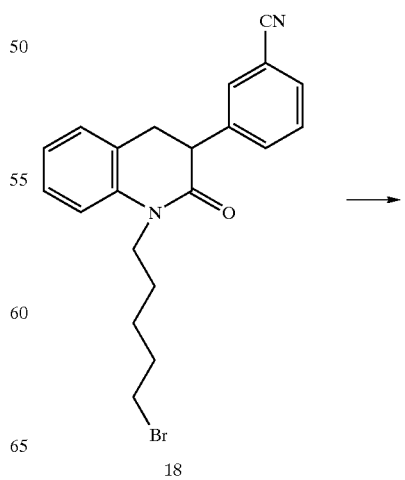

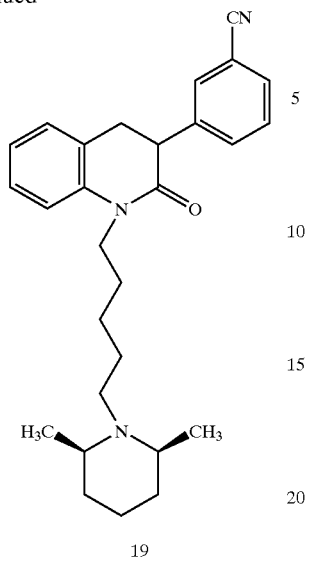

19

To 3-[1-(5-bromopentyl)-2-oxo-1,2,3,4-tetrahydro-3-quinolinyl]-benzenecarbonitrile (18) (1.59 g, 4.00 mmol) in DMF (3 mL) was added cis-2,6-dimethylpiperidine (10 mL, 74 mmol). The solution was stirred at 70° C. for 24 hours. The solution was cooled, diluted with water, and extracted with ethyl acetate (3 t 200 mL). The combined organic extracts were washed with saturated sodium bicarbonate (2×100 mL), washed with brine (2×100 mL), dried with magnesium sulfate, filtered, evaporated in vacuo, coevaporated with toluene, and dried under high vacuum to give (19) in quantitative yield as a yellow oil.

$^1$H NMR (CDCl$_3$, 300 MHz): δ 7.50–6.96 (8H, bm), 3.91 (2H, m), 3.80 (1H, in), 3.13 (2H, m), 2.67 (2H, bs), 2.36 (2H, bs), 1.66–1.15 (12H, bm), 1.01 (6H, in).

HPLC: RT=14.25 min. (Beckman 235328 C18 5 µm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (g) Preparation of: 3-(1-5-[(2R,6S)-2,6-dimethyltetrahydro-1(2H)-pyridinyl]pentyl-2-oxo-1,2,3,4-tetrahydro-3-quinolinyl)-N-hydroxybenzenecarboximidamide

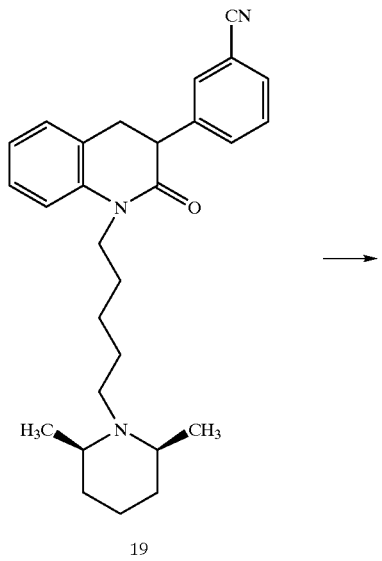

19

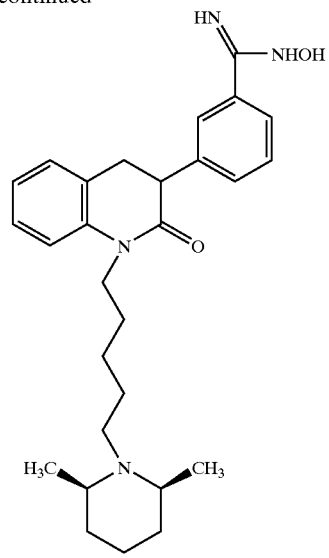

20

To 3-(1-5-[(2R,6S)-2,6-dimethyltetrahydro-1(2H)-pyridinyl]pentyl-2-oxo-1,2,3,4-tetrahydro-3-quinolinyl)benzenecarbonitrile (19) (1.00 g, 2.33 mmol) in methanol (20 mL) were added hydroxylamine hydrochloride (0.40 g, 5.76 mmol) and diisopropylethylamine (0.40 mL, 2.30 mmol). The solution was stirred at room temperature for 16 hours. The solvent was evaporated in vacuo, and the oil was dried under high vacuum to give (20) in quantitative yield.

HPLC: RT=9.22 min. (Beckman 235328 C18 5 µm 4.6 nm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (h) Preparation of: 3-(1-5-[(2R,6S)-2,6-dimethyltetrahydro-1 (2H)-pyridinyl]pentyl-2-oxo-1,2,3,4-tetrahydro-3-quinolinyl)-N-[(2,2,2-trifluoroacetyl)oxy]benzenecarboximidamide

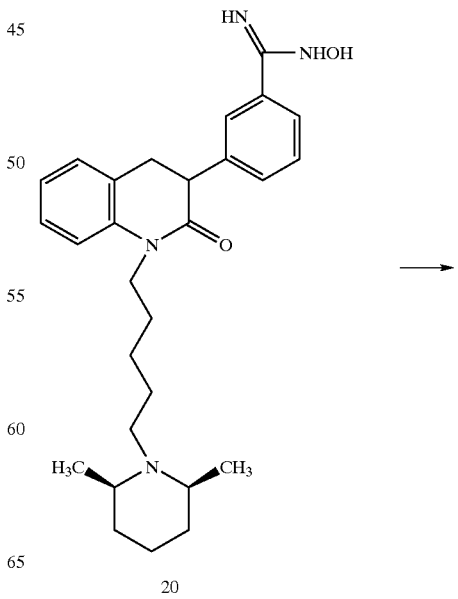

20

53

-continued

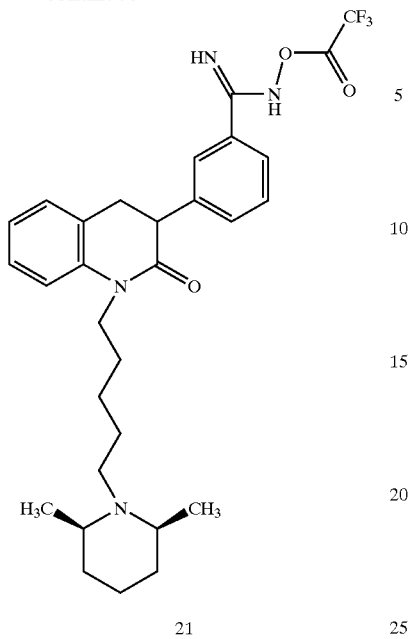

21

To 3-(1-5-[(2R,6S)-2,6-dimethyltetrahydro-1(2H)-pyridinyl]pentyl-2-oxo-1,2,3,4-tetrahydro-3-quinolinyl)-N-hydroxybenzenecarboximidamide (20) (1.07 g, 23.1 mmol) was added trifluoroacetic anhydride (10 mL), and the solution was stirred at room temperature for 3 hours. The solvent was removed in vacuo to give (21) as a yellow oil in quantitative yield.

HPLC: RT=18.37 min. (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (i) Preparation of: 3-(1-5-[(2R,6S)-2,6-dimethyltetrahydro 1 (2H)-pyridinyl]pentyl-2-oxo-1,2,3,4-tetrahydro-3-quinolinyl)benzenecarboximidamide

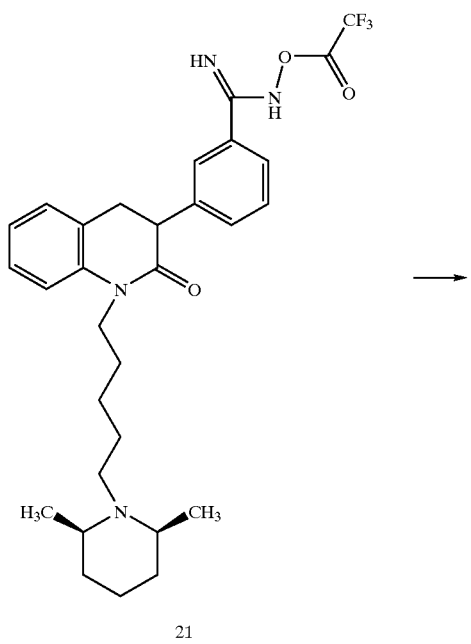

21

54

-continued

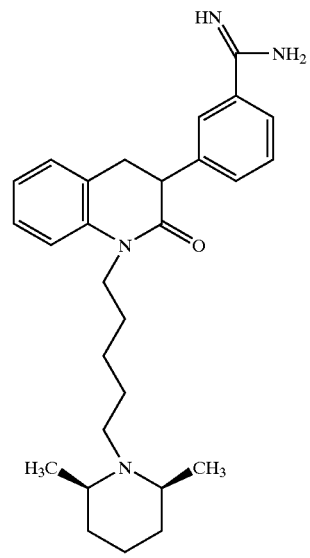

22

To 3-(1-5-[(2R,6S)-2,6-dimethyltetrahydro-[(2H)-pyridinyl]pentyl-2-oxo-1,2,3,4-tetrahydro-3-quinolinyl)-N-[(2,2,2-trifluoroacetyl)oxy]-benzenecarboximidamide (21) (1.27 g, 23.1 mmol) in trifluoroacetic acid (16 mL) was added 20% palladium on carbon (0.2 g), and the mixture was hydrogenated 33 PSI of 112 at 23° C. for 3 hours. The mixture was filtered, and the filter pad washed with trifluoroacetic acid. The combined filtrate and washings were evaporated in vacuo, and the residue was purified by preparative HPLC (Vydac 218TP54C18, eluted with a mixture of solvents consisting of (i) 0.11% trifluoroacetic acid in water, and (ii) 0.11% trifluoroacetic acid in acetonitrile, gradient profile 95:5 (i):(ii) to 60:40 (i):(ii) over 90 minutes, flow rate mL/minute, 214 mm) and lyophilized to give the TFA salt of (22) as an off-white solid. To the solid in acetonitrile (2 mL) and water (2 mL) was added Amberlite® IRA-400(CI) ion exchange resin. The mixture was filtered through additional resin, and the filtrate was lyophilized to give 619 mg (52%) of (22) as an off-white solid.

$^1$H NMR (DMSO, 400 MHz): 39.35 (1H, s), 9.07 (2H, s), 7.66 (2H, m), 7.49 (2H, m), 7.21 (3H, m), 6.97 (1H, m), 3.95 (3H, m), 3.42 (4H, bs), 3.35–2.86 (6H, bm), 1.75–1.26 (8H, bm), 1.20 (6H, m).

CI MS M+1=447.

HPLC: RT=9.65 min. (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Example 4
3-[3-(aminomethyl)phenyl]-1-5-[(2R,6S)-2,6-dimethyltetrahydro-1(2H)-pyridinyl]pentyl-3,4-dihydro-2(1H)-quinolinone

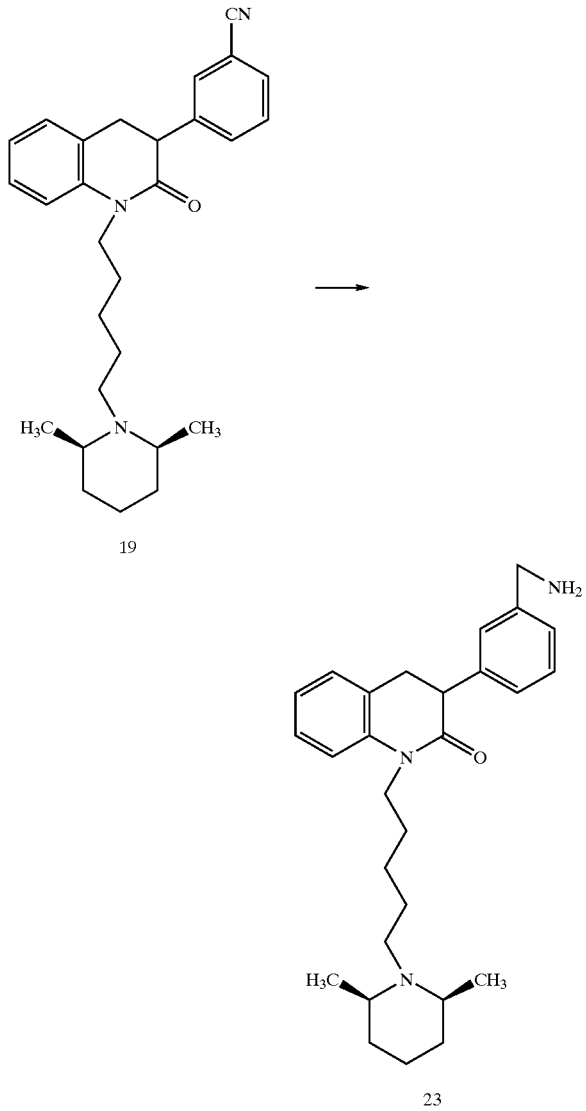

3-(1-5-[(2R,6S)-2,6-Dimethyltetrahydro-1(2H)-pyridinyl]pentyl-2-oxo-1,2,3,4-tetrahydro-3-quinolinyl)benzenecarbonitrile (19) (0.71 g, 16.5 mmol) was hydrogenated over Raney nickel (0.5 g) in methanol (45 mL) and triethylamine (5 mL) for 4 hours at room temperature. The mixture was filtered and the filter pad washed with methanol. The combined filtrate and washings were evaporated in vacuo, and the residue was purified by preparative HPLC (Vydac 218TP54 C18, eluted with a mixture of solvents consisting of (i) 0.1% trifluoroacetic acid in water, and (ii) 0.1% trifluoroacetic acid in acetonitrile, gradient profile 95:5 (i):(ii) to 60:40 (i):(ii) over 90 minutes, flow rate 20 mL/minute, λ=214 nm) and lyophilized to give the TFA salt of (23) as an off-white oily solid. To the oily solid in acetonitrile (2 mL) and water (2 mL) was added Amberlite® IRA-400(CI) ion exchange resin. The mixture was filtered through additional resin, and the filtrate was lyophilized to give 380 mg (45%) of (23) as an off-white solid.

$^1$H NMR (DMSO, 400 MHz): δ 8.38 (2H, s), 7.35–7.10 (7H, m), 6.95 (1H, m), 3.92 (4H, m), 3.83 (1H, m), 3.36 (4H, s), 3.23–2.86 (6H, bm), 1.75–1.30 (8H, bm), 1.21 (6H, m).

CI MS M+1=434.

HPLC: RT=9.56. (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

The invention compounds have demonstrated factor Xa inhibitory activity in the standard assays commonly employed by those skilled in the art.

Determination of Factor Xa $IC_{50}$ and $K_i$ Constants

The ability of compounds to act as inhibitors of human factor Xa catalytic activity is assessed by determination of that concentration of test substance that inhibits by 50% ($IC_{50}$) the ability of human factor Xa to cleave the chromogenic substrate S2765 (N-CBz-D-Arg-L-Gly-L-Arg-p-nitroanilide. 2HCl, DiaPharma). Typically, 145 μL human factor Xa (1 nM final, Enzyme Research Laboratories) in 10 mM HEPES, 150 mM NaCl, 0.1% BSA, pH 7.4 (HBSA buffer) and 5 μL of test substance in DMSO (2% final) are incubated for 60 minutes at room temperature. Following preheating to 37° C. for 5 minutes, to this mixture is added 1100 μL of S2765 in HBSA buffer. The velocity of S2765 hydrolysis is determined at 37° C. by measuring the initial rate of change of the optical density at $OD_{405}$ nM every 10 seconds for 5 minutes using a ThermoMax®D Kinetic Microplate Reader.

For $K_i$ determinations the assay conditions were essentially the same as above except for the following. The concentration of factor Xa was 50 μM, and that of the substrate, in this case a fluorogenic S2765 (i.e., S2765 with AMC tag instead of pNA, California Peptide Research), was over the range of 10 to 500 μM. The test compound and substrate in HBSA buffer were incubated as above, and the reaction was initiated with enzyme-buffer. The data (steady-state velocity at various concentrations of the substrate and the inhibitors) of the competitive inhibition was analyzed using the methods described by Segel (Enzyme Kinetics, Wiley Interscience Publications, 1993). A non-linear regression program, Kaleidograph and/or Microsoft Excel, was used to estimate the kinetic parameters ($K_m$, $V_{max}$ and $K_i$) by use of Michaelis-Menten and reciprocal Dixon plot fits.

Determination of Thrombin $IC_{50}$ and $K_i$ Constants

The ability of compounds to act as inhibitors of human thrombin catalytic activity is assessed by determination of that concentration of test substance that inhibits by 50% ($IC_{50}$) the ability of human thrombin to cleave the chromogenic substrate Chromozym TH (Tosyl-Gly-Pro-Arg-pNA*Ac, Boehringer Mannheim). Typically, 145 μL human thrombin (0.75 nM, Enzyme Research Laboratories) in a HPB buffer (10 mM HEPES, 100 mM NaCl, 0.05% BSA, 0.1% PEG-8000, pH 7.4) and 5 μL of test substance in DMSO (2% final) are incubated for 60 minutes at room temperature. Following preheating to 37° C. for 5 minutes, to this mixture is added 100 μL of Chromozym TH in HPB buffer. The velocity of Chromozym TH hydrolysis is determined at 37° C. by measuring the initial rate of change of the optical density at $OD_{405}$ nM every 10 seconds for 5 minutes using a ThermoMax® Kinetic Microplate Reader.

For $K_i$ determinations the assay conditions were essentially the same as the aforementioned except for the following. The concentration of thrombin used was 50 μM, and that of a fluorogenic Chromozym TH (i.e., Chromozym TH with AMC instead of pNA tag, Novabiochem) was over the range of 1 to 40 μM. The test compound and substrate in HPB buffer were incubated as above, and the reaction was initiated with enzyme-buffer and run at 24° C. Kinetic analysis was performed as for factor Xa $K_i$ determinations.

Determination of Trypsin $IC_{50}$ and $K_i$ Constants

The ability of compounds to act as inhibitors of human trypsin catalytic activity is assessed by determination of that concentration of test substance that inhibits by 50% ($IC_{50}$) the ability of human trypsin to cleave the chromogenic substrate S2222 (N-Bz-L-Ile-L-Glu-L-Gly-L-Arg-p-nitroanilide. HCl, DiaPharma). Typically, 145 $\mu$L human trypsin (0.5 nM final) in 10 mM HEPES, 150 mM NaCl, 0.1% BSA, and 5 $\mu$L of the test substance in DMSO (2% final) are incubated for 60 minutes at room temperature. Following preheating to 37° C. for 5 minutes, to this mixture is added 100 $\mu$L of S2222 in HBSA buffer (100 $\mu$M final), and the velocity of S2222 hydrolysis is determined at 37° C. by measuring the optical density at $OD_{405}$ nM every 10 seconds over 5 minutes using a ThermoMax® Kinetic Microplate Reader.

For $K_i$ determinations, the assay conditions were essentially the same as the aforementioned except that the reaction was initiated with enzyme-buffer and run at 24° C. using a substrate range of 10 to 500 $\mu$M. Kinetic analysis was performed as for factor Xa $K_i$ determinations.

Determination of Tissue Factor/Factor VIIa $IC_{50}$

The ability of compounds to act as inhibitors of the catalytic activity of human tissue factor/factor VIIa complex is assessed by determination of that concentration of test substance that inhibits by 50% ($IC_{50}$ the ability of a complex of human recombinant tissue factor/factor VIIa to cleave the chromogenic substrate Spectrozyme VIIa ($CH_3\ SO_2$-D-CHA-Arg-pNA*AcOH, American Diagnostica). Typically, 50 $\mu$L human factor VIIa (Enzyme Research Laboratories) is incubated for 10 minutes as a 1:1 mixture (5 nM final each) with 95 $\mu$L recombinant human tissue factor (American Diagnostica) in a modified HBSA buffer (10 mM Hepes, 5 mM $CaCl_2$, 0.1% BSA, pH 8.0). Then, 5 $\mu$L of the test substance in DMSO (2% final) is added and incubated for 60 minutes at room temperature. Following preheating to 37° C. for 5 minutes, to this mixture is added 100 $\mu$L of Spectrozyme VIIa (500 $\mu$M final) in modified HBSA, and the velocity of Spectrozyme VIIa hydrolysis is determined at 37° C. by measuring the optical density at an $OD_{405}$ nM every 10 seconds over 5 minutes using a ThermoMax® Kinetic Microplate Reader.

In Vitro Assay for Human Prothrombinase

This assay demonstrates the ability of test compounds of the invention to inhibit the human prothrombinase (PTase) complex (typically comprising of human factor Va, human factor Xa, $Ca^{2+}$, and phospholipid moiety) and thereby, the subsequent cleavage of prothrombin to yield thrombin. For determination of $IC_5'$ (PTase) of the compounds of the invention, PTase activity was expressed by thrombin activity.

PTase reaction was performed in 100 $\mu$L of mixture containing PTase (20 $\mu$M) PCPS (Avanti Polar Lipids following a procedure modified from Barenholz et al., Biochemistry, 1977;16:2806–2810) in a 30:70 ratio, 2.5 nM human factor Va (Enzyme Research Laboratories) and 2.5 $\mu$M human factor Xa (Enzyme Research Laboratories) in modified HEPES buffer (10 mM Hepes, 150 mM NaCl, 0.1% PEG-8000, 0.05% BSA, 2.5 mM $CaCl_2$, pH 7.4), 3 $\mu$M human prothrombin (Enzyme Research Laboratories) and varied concentrations of the test compounds (1 nM to 100 $\mu$M in DMSO, 2% final). Reaction was started by co-incubating PTase with test compound for 60 minutes at room temperature, followed by addition of prothrombin for 6 minutes at room temperature. Next, the reaction was quenched by the addition of 100 $\mu$L of 20 mM EDTA. Activity of the thrombin (product) is then measured in the presence of 50 $\mu$L S2238 (250 $\mu$M final, H-D-Phe-Pip-Arg-pNA*Ac, DiaPharma) as substrate by measuring the change at 37° C. in $OD_{405}$ nM for 5 minutes at 10-second intervals using a ThermoMax® Kinetic Microplate Reader.

Determination of Prothrombin Time (PT)

Rat, rabbit, dog and human blood (typically 1.8 mL) was collected and added to a sodium citrate solution (3.8%) to afford a 1:10 dilution. After centrifugation (2000 g for 10 minutes), the blood plasma was stored at –70° C. to 0° C. Conventional prothrombin time tests were carried out in the presence of various concentrations of test compound and the concentration of test compound required to double the clotting time determined. Typically, the test compound (50 $\mu$L volume of varying concentrations 0.1 $\mu$M to 1000 $\mu$M) and blood plasma (100 $\mu$L volume) were incubated at 37° C. for 10 minutes and then tissue thromboplastin, typically Neoplastine from American Bioproducts with calcium, was added. Fibrin formation and the time required for a clot to form were determined using an automated ST4 Clot Detection System in duplicate.

In an ex-vivo modification of this assay, drug was administered intravenously or orally to a group of rats or rabbits. At various times blood samples were collected, and the PT coagulation assay as described above were performed.

Arterio-Venous Shunt Stasis Antithrombotic Model

In vivo measurements of antithrombotic activity were performed according to the procedure of Vogel et al., Thromb. Res., 1989;54:399–410. Briefly, the vena cava was exposed, collateral veins were ligated, and sutures were loosely located around the inferior vena cava. These sutures were tightened after drug administration to induce stasis within the ligated portion of the vena cava. After an appropriate time, the thrombus was isolated and weighed. The effect of varying drug concentrations administered intravenously or orally on thrombus mass reflected antithrombotic activity.

Alternatively, and according to the procedure of Smith et al., Br. J. Pharmacol., 1982;77:29–38, the left jugular and right carotid artery were exposed and cannulated. A shunt, which contains silk threads or preweighed cotton, is then inserted which connects the two cannulated vessels. Once drug has been administered, the shunt is closed, and the thrombus that forms on the foreign surface in the shunt is removed after a period of time. Clot weight then reflects antithrombotic activity.

Arterial Thrombosis Model $FeCl_3$ Induced Carotid Arterial Injury Model

The $FeCl_3$ induced injury to the carotid artery in rats was induced according to the method described by Kurz K. D., Main R. W., Sandusky G. E., Thrombosis Research, 1990;60:269–280 and Schumacher W. A. et al., J. Pharmacology and Experimental Therapeutics, 1993;267: 1237–1242.

Male, Sprague-Dawley rats (375–410 g) were anesthetized with urethane (1500 mg\kg·ip). Animals were laid on a 37° C. heating pad. The carotid artery was exposed through a midline cervical incision. Careful blunt dissection was used to isolate the vessel from the carotid sheath. Using forceps, the artery was lifted to provide sufficient clearance to insert two small pieces of polyethylene tubing (PE-205) underneath it. A temperature probe (Physitemp MT23/3) was placed between one of the pieces of tubing and the artery. Injury was induced by topical application on the carotid artery above the temperature probe of a small disc (3 mm diameter) of Whatman No. 1 filter paper previously dipped in a 35% solution of $FeCl_3$. The incision area was covered with aluminum foil in order to protect the $FeCl_3$ from degradation by light. The vessel temperature was monitored for 60 minutes after application of $FeCl_3$ as an indication of blood flow. Vessel temperature changes were recorded on a thermister (Cole-Palmer Model 0853341).

The time between the $FeCl_3$ application and the time at which the vessel temperature decreased abruptly (>2.4° C.) was recorded as the time to occlusion of the vessel. The fold shift in mean occlusion time (MOT), therefore, refers to the time to occlusion in drug-treated animal divided by control time to occlusion. Inhibitor compounds were given as an intravenous bolus (0.75 mg/kg) followed immediately by an intravenous infusion (50 µg/kg/min via femoral vein).

Typically, the compounds of the invention show 50% inhibition of factor Xa proteolytic activity on a synthetic substrate in concentrations ranging from 50 µM to 1 nM.

| Structure | Name | Thrombin $IC_{50}$ µM | Trypsin $IC_{50}$ µM | Xa $IC_{50}$ µM |
|---|---|---|---|---|
| 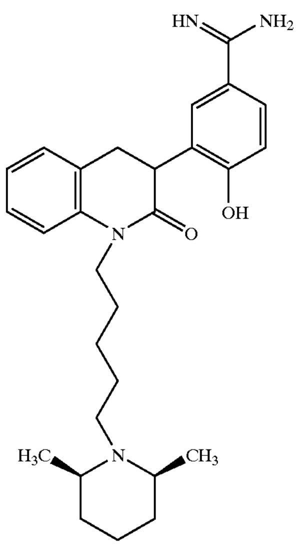 | 3-(1-5-[(2R,6S)-2,6-dimethyltetrahydro-1(2H)-pyridinyl]pentyl-2-oxo-1,2,3,4-tetrahydro-3-quinolinyl)-4-hydroxybenzene carboximidamide (Example 2) | 1.14 | 0.562 | 0.02 |

The foregoing biological test has been used to establish the compounds of this invention are useful for preventing and treating thrombotic disorders, for example, venous thrombosis, deep vein thrombosis, thrombophlebitis, arterial embolism, coronary and cerebral arterial thrombosis, cerebral embolism, kidney embolism, pulmonary embolism, first or recurrent myocardial infarction, unstable angina, and cerebral infarction, stroke, and atherosclerosis.

The compounds of the present invention can be administered alone or in combination with one or more therapeutic agents. These include, for example, other anticoagulant, antiplatelet, or platelet inhibitory agents which include non-steroidal anti-inflammatory agents such as aspirin, ibuprofen, naproxen sodium, indomethacin, piroxicam and ticlopidine, thrombin inhibitors such as argatroban, efegatran, inogatran, factor VIIa inhibitors, thrombolytic or fibrinolytic agents such as tissue plasminogen activator, urokinase or streptokinase, and GP IIIb-IIa antagonists.

The compounds are thus well-suited to formulation for convenient administration to mammals for the prevention and treatment of such disorders, The following examples farther illustrate typical formulations provided by the invention.

| Formulation 1 | |
|---|---|
| Ingredient | Amount |
| Compound of Formulas I-IV | 200 mg |
| Sodium benzoate | 5 mg |
| Isotonic saline | 1000 mL |

The above ingredients are mixed and dissolved in the saline for IV administration to a human suffering from, for example, arterial thrombosis.

| Formulation 2 | |
|---|---|
| Ingredient | Amount |
| Compound of Formulas I-IV | 100 mg |
| Cellulose, microcrystalline | 400 mg |
| Stearic acid | 5 mg |
| Silicon dioxide | 10 mg |
| Sugar, confectionery | 50 mg |

The ingredients are blended to uniformity and pressed into a tablet that is well-suited for oral administration to a human for preventing, for example, cerebral infarction.

| Formulation 3 | |
|---|---|
| Ingredient | Amount |
| Compound of Formulas I-IV | 200 mg |
| Starch, dried | 250 mg |
| Magnesium stearate | 10 mg |

The ingredients are combined and milled to afford material suitable for filling hard gelatin capsules administered to humans suffering from, for example, venous thrombosis.

| Formulation 4 | |
|---|---|
| | Amount % wt/wt |
| Compound of Formulas I-IV | 1 |
| Polyethylene glycol 1000 | 74.5 |
| Polyethylene glycol 4000 | 24.5 |

The ingredients are combined via melting and then poured into molds containing 2.5 g total weight.

| Formulation 5 | |
|---|---|
| Ingredient | Amount % wt/wt |
| Compound of Formulas I-IV | 0.1% |
| Propellant 11/12 | 98.9% |
| Oleic acid | 1% |

The ingredients are dispersed in oleic acid with the propellant. The mixture is added to an aerosol container fitted with a metering device.

What is claimed is:

1. A compound according to Formula I

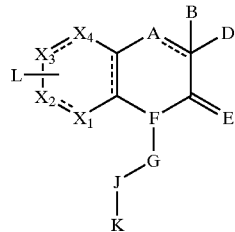

I or a stereoisomers or pharmaceutically acceptable salts, esters, or amides thereof, wherein:

A is selected from $CH_2$, CH, C(alkyl);

B is selected from H, alkyl, cycloalkyl, heteroalkyl, cycloalkylalkyl, heteroalkylalkyl, aryl, arylalkyl, heterocycle, heterocycloalkyl, each optionally substituted with $R_1$ and $R_2$;

D is selected from H, alkyl, cycloalkyl, heteroalkyl, cycloalkylalkyl, heteroalkylalkyl, aryl, arylalkyl, heterocycle, heterocycloalkyl, each optionally substituted with $R_1$ and $R_2$;

E is absent or selected from O, S, NH;

F is selected from N or $NCH_2$;

G is selected from alkyl, alkyl interrupted by one or more heteroatoms, cycloalkyl, cycloalkyl interrupted by one or more heteroatoms;

J is heterocycle optionally substituted with $R_1$ and $R_2$;

K is absent or selected from an alkyl, alkyl interrupted by one or more heteroatoms, cycloalkyl interrupted by one or more heteroatoms, cycloalkylalkyl interrupted by one or more heteroatoms, each optionally substituted with $R_1$ and $R_2$;

L is selected from H, chlorine, fluorine, bromine, iodine, OH, O(alkyl), alkyl, fluoroalkyl, $NO_2$, SH, $S(O)_n$(alkyl), $SO_3H$, $SO_3$alkyl, C(=O)heteroaryl, C(=O)heteroarylalkyl, C(=O)OH, NC(=O)alkyl, NC(=O)aryl, NC(=O)cycloalkyl, NC(=O)cycloalkylalkyl, NC(=O) alkylaryl, $R_1$, $R_2$;

$R_1$ is selected from H, C(=NH)$NHNH_2$, alkylC(=NH)$NHNH_2$, C(=NH)NHOH, alkylC(=NH)NHOH, NHC(=NH)$NH_2$, alkylNHC(=NH)$NR_2$, C(=S)$NH_2$, alkylC(=S)$NH_2$, C(=NH)alkyl, alkylC(=NH)alkyl, C(=$NR_3$)N($R_4$)($R_5$), alkylC(=$NR_3$)N($R_4$)($R_5$);

$R_2$ is selected from H, chlorine, fluorine, bromine, iodine, OH, Oalkyl, NC(=O)alkyl, NC(=O)aryl, NC(=O)cycloalkyl, NC(=O)alkylaryl, C(=O)alkyl, C(=O)cycloalkyl. C(=O)cycloalkyl, C(=O)aryl, C(=O)alkyl, C(=O)heteroaryl and C(=O)heteroarylalkyl, $NO_2$, SH, $S(O)_n$($C_{1-10}$alkyl), $SO_3H$, $SO_3$alkyl, CHO, C(=O)OH, alkyl, C(=NH)alkyl, C(=NH)$NHNH_2$, alkylC(=NH)$NHNH_2$, C(=NH)NHOH, alkylC(=NH)NHOH, NHC(=NH)$NH_2$, alkylNHC(=NH)$NHNH_2$, C(=S)$NH_2$, alkylC(=S)$NH_2$, alkylC(—NH)alkyl, C(=$NR_3$)N($R_4$)($R_5$), alkylC(=$NR_3$)N($R_4$)($R_5$);

$R_3$, $R_4$, and $R_5$ are a hydrogen atom, alkyl group having 1 to 4 carbon atoms optionally interrupted by a heteroatom, or $R_4$ and $R_5$ arc bonded to form —$(CH_2)_p$—W—$(CH_2)_q$-, wherein p and q are an integer of 2 or 3, a certain position on the methylene chain is unsubstituted or substituted by an alkyl group having 1 to 4 carbon atoms, W is a direct bond, —$CH_2$—, —O—, —N($R_6$)—, or —$S(O)_2$— wherein $R_6$ is H or alkyl, and r is 0 or 1 or 2;

n is selected from 0, 1, 2;

$X_1$ is C;

$X_2$ is C;

$X_3$ is C;

$X_4$ is C; and

--- represents an optional additional bond.

2. A compound according to claim 1 according to Formula II

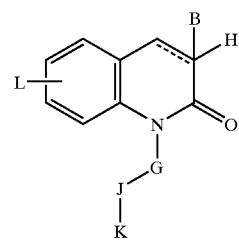

II or a stereoisomers or pharmaceutically acceptable salts, esters, or amides thereof, wherein B, G, J, K, L, and --- are as defined above.

3. A compound according to Formula III

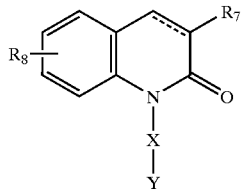

III or a stereoisomer or pharmaceutically acceptable salts, esters, or amide thereof, wherein X, Y, $R_7$, $R_9$, and --- are as follows:

X is selected from $(CH_2)_5$,
$(CH_2)_4$,
$(CH_2)_6$,
$CH_2C(=O)NHCH_2CH_2$,
$CH_2CH_2NHC(=O)CH_2$,
$(CH_2)_2NH(CH_2)_2$,
$(CH_2)_2O(CH_2)$,
$C_6H_4$,
$CH_2C_6$,
$C_6H_4CH_2$,
$C_6H_{10}$,
$CH_2C_6H_{10}$,
$C_5H_8$,
$CH_2C_5H_8$,
$C_5H_8CH_2$, and
$CH_2CH=CHCH_2CH_2$;

Y is selected from 2,6-dimethylpiperidinyl,
piperidinyl,
2,2,6,6-tetramethyl-piperidinyl-4-one,
(2-carboxy)piperidinyl,
(3-carboxy)piperidinyl,
(4-carboxy)piperidinyl,
3,5-dimethylpiperidinyl,
(4-hydroxy)piperidinyl,
(2-imino)piperidinyl,
piperidin-4-one-yl,
(2-dimethylaminomethyl)-piperidinyl,
(4-dimethylamino)-piperidinyl,
(4-sulphonyloxy)piperidinyl,
(2-phenyl)piperidinyl,
2,5-dimethylpyrrolidinyl,
pyrrolidinyl,
(2-carboxy)pyrrolidinyl,
(3-N-acetyl-N-methyl)pyrrolidinyl,
(3-amino)pyrrolidinyl,
(2,5-bis-methoxymethyl)-pyrrolidinyl,
2-hydroxymethyl-pyrrolidinyl,
2-hydroxymethyl-5-methyl-pyrrolidinyl,
diisopropylamino,
diethylamino,
methylamino,
1-methyl-4,5-dihydro-1H-imidazol-2-yl,
2,5-dimethyl-1H-1-imidazolyl,
morpholinyl,
2,6-dimethylmorpholinyl,
piperazinyl,
2,6-dimethylpiperazinyl,
1H-pyrazolyl,
tetrahydro-1H-pyrazolyl,
2,5-dimethyltetrahydro-1H-1-pyrazolyl, and
1,2,3,4-tetrahydro-2-oxo-3-phenyl-1-quinolinyl;

$R_7$ is selected from (3-amidino)phenyl,
phenyl,
4-methoxyphenyl,
4-(amidino)phenyl,
3-(aminocarbonyl)phenyl,
3(methoxycarbonyl)phenyl,
(3-hydroxy)phenyl,
[3-hydroxyamino(imino)methyl]-phenyl,
[3-hydrazino(imino)methyl]-phenyl
(3-aminomethyl)phenyl, (3-amino)phenyl,
(3-methylamino)phenyl,
(3-dimethylamino)phenyl,
(5-amidino-2-hydroxy)phenyl,
(1-amidino)piperid-3-yl,
(1-amidino)pyrrolid-3-yl,
(5-amidino)thien-2-yl,
(5-amidino)furan-2-yl,
(5-amidino)-1,3-oxazol-2-yl,
(2-amidino)-1,3-oxazol-5-yl,
1H-pyrazol-5-yl,
tetrahydro-1H-pyrazol-3-yl,
(1-amidino)tetrahydro-1H-pyrazol-3-yl,
(2-amidino)-1H-imidazol-4-yl,
(2-amino)-1H-imidazol-4-yl,
(5-amidino)-1H-imidazol-2-yl,
(5-amino)-1H-imidazol-2-yl,
pyridin-3-yl,
(4-amino)pyridin-3-yl,
(4-dimethylamino)pyridin-3-yl,
(6-amino)pyridin-2-yl,
(6-amidino)pyridin-2-yl,
(2-amino)pyridin-4-yl,
(2-amidino)pyridin-4-yl,
(2-amidino)pyrimid-4-yl,
(2-amino)pyrimidin-4-yl,
(4-amidino)pyrimid-2-yl,
(4-amino)pyridin-2-yl
(6-amidino)pyrazin-2-yl,
(6-amino)pyrazin-2-yl,
(4-amidino)-1,3,5-triazin-2-yl,
(4-amino)-1,3,5-triazin-2-yl,
(3-amidino)1,2,4-triazin-5-yl,
(3-amino)-1,2,4-pyridin-5-yl,
(3-amidino)benzyl,
(3-amino)benzyl,
(3-aminomethyl)benzyl,
(1-amidino)piperid-3-ylmethyl,
(1-amidino)pyrrolid-3-ylmethyl,
(5-amidino)thien-2-ylmethyl,
(5-amidino)furan-2-ylmethyl, (5-amidino)oxazol-2-ylmethyl,
(2-amidino)imidazol-5-ylmethyl,
(5-amidino)imidazol-2-ylmethyl,
(6-amidino)pyridin-2-ylmethyl,
(6-amidino)pyridin-2-ylmethyl,
(2-amidino)pyridin-4-ylmethyl,
(2-amino)pyrimidin-4-ylmethyl,
(4-amidino)pyrimidin-2-ylmethyl,
(4-amino)pyrimidin-2-ylmethyl,
(6-amidino)pyrazin-2-ylmethyl,
(6-amino)pyrazin-2-ylmethyl,
3-aminocyclohexyl,
3-amidinocyclohexyl,
3-aminocyclohexylmethyl,
3-amidinocyclohexylmethyl,
3-aminocyclopentyl,
3-amidinocyclopentyl,
3-aminocyclopentylmethyl, and
3-amidinocyclopentylmethyl; and
$R_8$ is selected from H,
Cl,
F,
SH,
SMe,
$CF_3$,
$CH_3$,
$CO_2H$,
$CO_2Me$,
CN,
C(=NH)$NH_2$,
C(=NH)NHOH,
C(=O)$NH_2$,
C(=O)$NH_2$,
$CH_2OH$,
$CH_2NH_2$,
$NO_2$,
OH,
OMe,
$OCH_2Ph$,
$OCH_2CO_2H$,
$O(CH_2)_2CO_2H$,
$O(CH_2)_3CO_2H$,
$NHCH_2CO_2H$,
$NH(CH_2)_2CO_2H$,
$NH(CH_2)_3CO_2H$,
$OCH_2CH_2OH$,
$OCH_2$(1H-tetrazol-5-yl),
$NH_2$,
NHButyl,
$NMe_2$,
$NHCH_2Ph$,
NHC(=O)Me,
NHC(=O)c-Hexyl,
NHC(=O)$CH_2$c-Hexyl,
NHC(=O)Ph,
NHC(=O)$CH_2Ph$,
NHS(=O)$_2$Me, NHS(=O)$_2$c-Hexyl,
NHS(=O)$_2CH_2$c-Hexyl,
NHS(=O)$_2$Ph, and
NHS(=O)$_2CH_2$Ph; and
--- represents an optional additional end.
4. A compound according to Formula IV

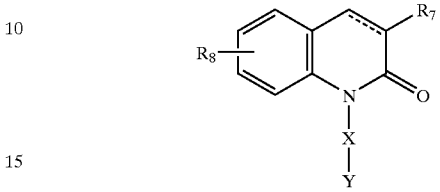

IV or a stereoisomers or pharmaceutically acceptable salts, esters, or amides thereof, wherein X, Y, $R_7$, $R_8$, and --- are as follows:
X is selected from $(CH_2)_5$,
$(CH_2)_4$,
$(CH_2)_6$,
$CH_2C(=O)NHCH_2CH_2$,
$CH_2CH_2NHC(O)CH_2$,
$(CH_2)_2NH(CH_2)_2$,
$(CH_2)_2O(CH_2)_2$,
$C_6H_4$,
$CH_2C_6H_4$,
$C_6H_4CH_2$,
$C_6H_{10}$,
$CH_2C_6H_{10}$,
$C_6H_{10}CH_2$,
$C_5H_8$,
$CH_2C_5H_8$,
$C_5H_8CH_2$, and
$CH_2CH=CHCH_2CH_2$;
Y is selected from 2,6-dimethylpiperidinyl,
piperidinyl,
2,2,6,6-tetramethyl-piperidinyl-4-one,
(2-carboxy)piperidinyl
(3-carboxy)piperidinyl,
(4-carboxy)piperidinyl,
3,5-dimethylpiperidinyl,
(4-hydroxy)piperidinyl,
(2-imino)piperidinyl,
piperidin-4-one-yl,
(2-dimethylaminomethyl)-piperidinyl,
(4 dimethylamino)-piperidinyl,
(4-sulphonyloxy)-piperidinyl,
(2-phenyl)piperidinyl,
2,5-dimethylpyrrolidinyl,
pyrrolidinyl,
(2-carboxy)pyrrolidinyl,
(3-N-acetyl-N-methyl)pyrrolidinyl,
(3-amino)pyrrolidinyl,
(2,5-bis-methoxymethyl)-pyrrolidinyl,
2-hydroxymethyl-pyrrolidinyl,
2-hydroxymethyl-5-methyl-pyrrolidinyl,
diisopropylamino, diethylamino,
methylamino,
1-methyl-4,5-dihydro-1H-imidazol-2-yl,
2,5-dimethyl-1H-1-imidazolyl,
morpholinyl,
2,6-dimethylmorpholinyl,
piperazinyl,
2,6-dimethylpiperazinyl
1H-pyrazolyl,
tetrahydro-1H-pyrazolyl, and
2,5-dimethyltetrahydro-1H-1-pyrazolyl;

$R_7$ is selected from (3-amidino)phenyl,
(3-hydroxy)phenyl,
[3-hydroxy]amino(imino)methyl-phenyl,
[3-hydrazino(imino)methyl)-phenyl,
(3-aminomethyl)phenyl
(3-methylamino)phenyl,
(3-dimethylamino)phenyl,
(5-amidino-2-hydroxy)phenyl,
(1-amidino)piperid-3-yl,
(1-amidino)pyrrolid-3-yl,
(5-amidino)thien-2-yl,
(5-amidino)film-2-yl,
(5-amidino)-1,3-oxazol-2-yl,
(2-amidino)-1,3-oxazol-5-yl,
1H-pyrazol-5-yl,
tetrahydro-1H-pyrazol-3-yl,
(1-amidino)tetrahydro-1H-pyrazol-3-yl,
(2-amidino)-1H-imidazol-4-yl,
(2-amidino)-1H-imidazol-4-yl,
(5-amidino)-1H-imidazol-2-yl,
(5-amino)-1H-imidazol-2-yl,
pyridin-3-yl,
(4-amino)pyridin-3-yl
(4-dimethylamino)pyridin-3-yl,
(6-amino)pyridin-2-yl,
(6-amidino)pyridin-2-yl,
(2-amino)pyridinyl,
(2-amidino)pyridin-4-yl,
(2-amidino)pyridine-4-yl,
(2-amino)pyrimidin-4-yl,
(4-amidino)pyrimid-2-yl
(4-amino)pyrimidin-2-yl,
(6-amino)pyrazin-2-yl,
(6-amidino)pyrazin-2-yl,
(4-amidino)-1,3,5-triazin-2-yl,
(4-amino)-1,3,5-triazin-2-yl,
(3-amidino)-1,2,4-triazin-5-yl,
(3-amino)-1,2,4-triazin-5-yl,
(3 amidino)benzyl, (3-amino)benzyl,
(3-aminomethyl)benzyl,
(1-amidino)piperid-3-ylmethyl,
(1-amidino)pyrrolid-3-ylmethyl,
(5-amidino)thien-2-ylmethyl,
(5-amidino)furan-2-ylmethyl,
(5-amidino)oxazol-2-ylmethyl,
(2-amidino)imidazol-5-ylmethyl,
(5-amidino)imidazol-2-ylmethyl,
(6-amidino)pyridin-2-ylmethyl,
(6-amino)pyridin-2-ylmethyl,
(2-amidino)pyrimidin-4-ylmethyl,
(2-amino)pyrimidin-4-ylmethyl,
(4-amidino)pyrimidin-2-ylmethyl,
(4-amino)pyrimidin-2-ylmethyl,
(6-amidino)pyrazin-2-ylmethyl,
(6-amino)pyrazin-2-ylmethyl,
3-aminocyclohexyl,
3-amidinocyclohexyl,
3-aminocyclohexylmethyl,
3-amidinocyclohexylmethyl,
3-aminocyclopentyl
3-amidinocyclopentyl
3-aminocyclopentylmethyl, and
3-amidinocyclopentylmethyl; and $R_8$ is selected from H,
Cl,
F,
SH,
SMe,
$CF_3$,
$CH_3$,
$CO_2H$,
$CO_2Me$,
CN,
C(=NH)$NH_2$,
C(=NH)NHOH,
C(=NH)$NHNH_2$,
C(=O)$NH_2$,
$CH_2OH$,
$CH_2NH_2$,
$NO_2$,
OH,
OMe,
$OCH_2Ph$,
$OCH_2CO_2H$,
$O(CH_2)_2CO_2H$,
$O(CH_2)_3CO_2H$,
$NHCH_2CO_2H$,
$NH(CH_2)_2CO_2H$,
$NH(CH_2)_3CO_2H$,
$OCH_2CH_2OH$,
$OCH_2$(1H-tetrazol-5-yl),
$NH_2$,
NHButyl,
$NMe_2$,
NHPh,
$NHCH_2Ph$,
NHC(=O)Me,
NHC(=O)c-Hexyl,
NHC(=O)$CH_2$c-Hexyl,
NHC(=O)Ph,
NHC(=O)$CH_2Ph$,
NHS(=O)$_2$Me,
NHS(=O)$_2$c-Hexyl, NHS(=O)₂CH₂c-Hexyl,
NHS(=O)₂P, and
NHS(=O)₂CH₂Ph; and
--- represents an optional additional bond.

5. A compound according to claim 4 where X is (CH₂)₅.
6. A compound according to claim 4 where Y is 2,6-dimethylpiperidinyl.
7. A compound according to claim 4 where R₇ is (2-hydroxy-5-amidino)phenyl.
8. A compound according to claim 4 wherein R₈ is H.
9. A compound according to claim 4 where X is (CH₂)₅, Y is 2,6-dimethylpiperidinyl and R₈ is H.
10. A compound according to claim 4 where X is (CH₂)₅, Y is 2,5-dimethylpyrrolidinyl and R₈ is H.
11. A compound which is:

3-(1-5-[(2)-2,6-2,6-Dimethyltetrahydro-1(2H)-pyridinyl]pentyl-2-oxo-1,2-dihydro-3-quinolinyl)benzenecarboximidamide;

1-5-[(2R,6S)-2,6-Dimethyltetrahydro-[(2H)-pyridinyl]pentyl-33-hydroxyphenyl)-2(1H)-quinolinone;

3-(1-5-[(2R,6S)-2,6-Dimethyltetrahydro-1(2H)pyridinyl]pentyl-2-oxo-1,2-dihydro-3-quinolinyl)-N-hydroxybenzenecarboxamide;

3-(1-S-[(2R,6S)-2,6-Dimethyltetrahydro-1(2H)-pyridinyl]pentyl-2-oxo-1,2-dihydro-3-quinolinyl)benzenecarboximidohydrazide;

3-[3-(Aminomethyl)phenyl]-1-5-[(2R,6S)-2,6dimethyltetrahydro-1(2H)-pyridinyl]pentyl-2(1H)-quinolinone;

3-(3-Aminophenyl)-1-5-[(2R,6S)-2,6-dimethyltetrahydro-1(2H)-pyridinyl]pentyl-2(1H)-quinolinone;

1-5-[(2R,6S)-2,6-Dimethyltetrahydro-1(2H)-pyridinyl]pentyl-3-[3-(methylamino)phenyl]-2(1H)-quinolinone;

3-[3-Dimethylamino)phenyl]-1-5-[(2R,6S)2,6-dimethyltetrahydro-1(2H)-pyridinyl]pentyl-2(1H)-quinolinone;

3-(1-5-[(2R,6S)-2,6-Dimethyltetrahydro-1(2H)-pyridinyl]pentyl-2-oxo 1,2-dihydro-3-quinolinyl)-4-hydroxybenzenecarboximidamide;

3-(1-5-[(2R,6S)-2,6-Dimethyltetrahydro-1(2H)-pyridinyl]pentyl-2-oxo-1,2-dihydro-3-quinolinyl)tetrahydro-[(2H)-pyridinecarboximidamide;

3-(1-5-[(2R,6S)-2,6-Dimethyltetrahydro-1(2H)-pyridinyl]pentyl-2-oxo-1,2-dihydro-3-quinolinyl-1-pyrrolidinecarboximidamide;

5-(1-5-[(2R,6S)-2,6-Dimethyltetrahydro-1(2H)-pyridinyl]pentyl-2-oxo-1,2-dihydro-3-quinolyl)-2-thiophenecarboximidamide;

5-(1-S-(2R,6S) 2-Dimethyltetrahydro-1(2H)-pyridinyl]pentyl-2-oxo-1,2-dihydro-3-quinolinyl)₂-furancarboximidamide;

2-(1-5-[(2R,6S)-2,6-Dimethyltetrahydro-1(2H)-pyridinyl]pentyl-2-oxo-1,2-dihydro-3-quinolinyl)-1,3-oxazole-5-carboximidamide;

5-(1-5-[(2R,6S)-2,6-Dimethyltetrahydro-1(2H)-pyridinyl-pentyl-2-oxo-1,2-dihydro-3-quinolinyl)-1,3-oxazole-2-carboximidamide;

1-5-[(2R,6S)-2,6-Dimethyltetrahydro-1(2H)-pyridinyl]pentyl-1H-pyrazol-3-yl)-2(1H)-quinolinone;

1-5-(2R,6S)-2,6-Dimethyltetrahydro-1(2H)-pyridinyl]pentyl-3-tetrahydro-1H-pyrazol-3-yl-2(1-quinolinone;

3-(1-5-[(2R,6S)-2,6-Dimethyltetrahydro-1(2H)-pyridinyl]pentyl-2-oxo-1,2-dihydro-3-quinolinyl)-1-pyrazolidinecarboximidamide;

5-(1-5-[(2R,6S)-2,6-Dimethyltetrahydro-1(2H)-pyridinyl]pentyl-2-oxo-1,2-dihydro-3 quinolinyl)-1H-imidazole-2-carboximidamide;

3(2-Amino-1H-imidazol-5-yl)-1-5-[(2R,6S)-2,6-dimethyltetrahydro-[(2H)-pyridinyl]pentyl-2(1H)-quinolinone;

2-(1-5-[(2R,6S)-2,6-Dimethyltetrahydro-1(2H)-pyridinyl-pentyl-2-oxo-1,2-dihydro-3-quinolinyl)1H-imidazole-5-carboximidamide;

3-(5-Amino-1H-imidazol-2-yl)-5-[(2R,6S)-2,6-dimethyltetrahydro-1(2H)-pyridinyl]pentyl-2(1H)-quinolinone;

1-5-[(2R,6S)-2,6-Dimethyltetrahydro-1(2H)-pyridinyl]pentyl-3-(3-pyridinyl)-2(1H)quinolinone;

3-(6-Amino-3-pyridinyl)-1-5-[(2R,6S)-2,6-dimethyltetrahydro-1(2H)-pyridinyl]pentyl-2(1H)-quinolinone;

3-[6(Dimethylamino)-3-pyridinyl]-1-5-1(2R,6S)-2,6-dimethyltetrahydro-1(2H)-pyridinyl]pentyl-2(1H)-quinolinone;

3-(6-Amino-2-pyridinyl)-1-5-[(2R,6S)-2,6-dimethyltetrahydro-1(2H)-pyridinyl]pentyl-2(1H)quinolinone;

(1-5-[(2R,6S)-2,6-Dimethyltetrahydro-1(2H)-pyridinyl]pentyl-2-oxo-1,2-dihydro-3-quinolinyl)-2-pyridinecarboximidamide;

(2-Amino-4-pyridinyl)-1-5-[(2R,6S)-2,6-dimethyltetrahydro-[(2H)-pyridinyl]pentyl-2(1H)-quinolinone;

4-1-5-[(2R,6S)-2,6-Dimethyltetrahydro-1(2H)-pyridinyl]pentyl-2-oxo-1,2-dihydro-3-quinolinyl)-2-pyridinecarboximidamide;

4-(1-S-[(2R,6S)-2,6-Dimethyltetrahydro-1-(2H)-pyridinyl]pentyl-2-oxo 1,2-dihydro-3-quinolinyl)2-pyridinecarboximidamide;

3-(2-Amino-4-pyridyl)-1-5-[(2R₆S)-2,6-methyltetrahydro-(2H)-pyridinyl]pentyl-2(1H)-quinolinone;

2-(1-5-[(2R,6S)-2,6-Dimethyltetrahydro-1(2H)pyridinyl]pentyl-2-oxo-1,2-dihydro-3-quinolinyl)-4-pyrimidinecarboximidamide;

3-(4-Amino-2-pyrimidinyl)-1-5-[(2R,6S)-2,6-dimethyltetrahydro-1(21)-pyridinyl]pentyl-2(1H)-quinolinone;

6-(1-5-[((2R,6S)-2,6-Dimethyltetrahydro-1(2H)-pyridinyl-pentyl-2-oxo-1,2-dihydro-3-quinolinyl)-2-triazine-3-carboximidamide;

3-(6-Amino-2-pyrazinyl)-1-5-[(2R,6S)-2,6-dimethyltetrahydro-1(2H)-pyridinyl]pentyl-2(1H)-quinolinone;

4-(1-5-[(2R,6S)-2,6-Dimethyltetrahydro-1(2H)-pyridinyl]pentyl-2-oxo-1,2-dihydro-3-quinolinyl)-1,3,5-triazine-2-carboximidamide;

3-(4-Amino-1,3,5-triazin-2-yl)-1-5-[(2R,6S)-2,6-dimethyltetrahydro-1(2H)-pyridinyl]pentyl-2(1H)-quinolinone;

5-(1-5-[(2R,6S)-2,6-Dimethyltetrahydro-1(2H)-pyridinyl]pentyl-2-oxo-1,2-dihydro-3-quinolinyl)-1,2,4-triazine-3-carboximidamide;

3-(3-Amino-1,2,4-triazine-5-yl)-1-5-(2R,6S)-2,6-dimethyltetrahydro-1-(2H)-pyridinyl]pentyl-2(1H)-quinolinone;

3-[1-5-[(2R,6S)-2,6-Dimethyltetrahydro-[(2-pyridinyl]pentyl-2-oxo-1,2-dihydro-3-quinolinyl)methyl]benzenecarboximidamide;

3-(3-Aminobenzyl)-1-5-[(2R,6S)-2,6-dimethyltetrahydro-1(2H)-pyridinyl]pentyl-2(1H) quinolinone;

3-[3-(Aminomethyl)benzyl]-1-5-[(2R,6S)-2,6-dimethyltetrahydro-1(2H) pyridinyl]pentyl-2(1H)-quinolinone;

3-[(1-5-[(2R,6S)-2,6-Dimethyltetrahydro-1(2H)-pyridinyl]pentyl-2-oxo-1,2-dihydro-3-quinolinyl)methyl]tetrahydro-1(2H)-pyridinecarboximidamide;

3-[(1-5-[(2R,6S)-2,6-Dimethyltetrahydro-1(2H)-pyridinyl]pentyl-2-oxo-1,2-dihydro-3-quinolinyl)methyl]-1-pyrrolidinecarboximidamide;

5-[(1-5-[(2R,6S)-2,6-Dimethyltetrahydro-1(2H)-pyridinyl]pentyl-2-oxo-1,2-dihydro-3-quinolinyl)methyl]-2-thiophenecarboximidamide;

5-[(1-5-[(2R,6S)-2,6 Dimethyltetrahydro-1(2H)-pyridinyl]pentyl-2-oxo-1,2-dihydro-3 quinolinyl)methyl)-2-furancarboximidamide;

2-[(1-5-[(2R,6S)-2,6-Dimethyltetrahydro-1(2H)-pyridinyl]pentyl-2-oxo-1,2-dihydro-3-quinolinyl)methyl]-1,3-oxazole-5-carboximidamide;

5-[(1-5-[(2R$_{16}$S)-2,6-Dimethyltetrahydro-1(2H)-pyridinyl]pentyl-2-oxo-1,2-dihydro-3-quinolinyl)methyl]-1H-imidazole-2-carboximidamide;

2-[(1-5-[(2R,6S)-2,6-Dimethyltetrahydro-1(2H)-pyridinyl]pentyl-2-oxo-1,2-dihydro-3-quinolinyl)methyl]-1H-imidazole-5-carboximidamide;

6-[(1-5-[(2R,6S)-2,6-Dimethyltetrahydro-1(2H)-pyridinyl]pentyl-2-oxo-1,2-dihydro-3-quinolinyl)methyl]-2-pyridinecarboximidamide;

3-[(6-Amino-2-pyridinyl)methyl]-1-5-[(2R,6S)-2,6-dimethyltetrahydro-1(2H)-pyridinyl]pentyl-2(1H)-quinolinone;

4-[(1-5-[(2R,6S)-2,6-Dimethyltetrahydro-1(2H)-pyridinyl]pentyl-2-oxo-1,2-dihydro-3-quinolinyl)methyl]-2-pyrimidinecarboximidamide;

3-[(2-Amino-4-pyrimidinyl)methyl]-1-5-[(2R,6S)-2,6-dimethyltetrahydro-1(2H)-pyridinyl]pentyl-2(1H)-quinolinone;

2-[(1-5-((2R,6S)-2,6-Dimethyltetrahydro-1(2H)-pyridinyl]pentyl-2-oxo-1,2-dihydro-3-quinolinone)methyl]4-pyrimidinecarboximidamide;

3-[(4-Amino-2-pyrimidinyl)methyl]-1-5-[(2R,6S)-2,6-dimethyltetrahydro-1(2H)-pyridinyl]pentyl-2(1H)-quinolinone;

6-[(1-5-[(2R,6S)-2,6-Dimethyltetrahydro-1(2H) pyridinyl]pentyl-2-oxo-1,2-dihydro-3-quinolinyl) methyl]-2-pyrazinecarboxamide;

3-[(6-Amino-2-pyrazinyl)methyl]-1-5-[(2R,6S)-2,6-dimethyltetrahydro-1-(2H)-pyridinyl]pentyl-2(1H)-quinolinone;

3-(3-Aminocyclohexyl)-1-5-[(2R,6S)-2,6-dimethyltetrahydro-1(2H)-pyridinyl]pentyl-2(1H)-quinolinone;

3-[(1-5-[(2R,6S)-2,6-Dimethyltetrahydro-[(2H)-pyridinyl]pentyl-2-oxo-1,2-dihydro-3-quinolinyl) cyclohexanecarboximidamide;

3-[(3-Aminocyclohexyl)methyl]-1-5-[(2R,6S)-2,6-dimethyltetrahydro-1(2H)-pyridinyl]pentyl-2(1H)-quinolinone;

3-[(1-5-[(2R,6S)-2,6-Dimethyltetrahydro-1(2H) pyridinyl]pentyl-2-oxo-1,2-dihydro-3-quinolinyl) methyl]cyclohexanecarboximidamide;

3-(3-Aminocyclopentyl)-1-S-(2R,6S)2,6-dimethyltetrahydro-1-(2H)-pyridinyl]pentyl-2(1H)-quinolinone;

3-(1-5-[(2R,6S)-2,6-Dimethyltetrahydro-1(2H)-pyridinyl]pentyl-2-oxo-1,2-dihydro-3-quinolinyl) cyclopentanecarboximidamide;

3-[(3-Aminocyclopentyl)methyl]-1-5-[(2R,6S)2,6-dimethyltetrahydro-1(2H)-pyridinyl]pentyl-2(1H) quinolinone;

3-[(1-5-[(2R,6S)-2,6-Dimethyltetrahydro-1(2H)-pyridinyl]pentyl-2-oxo-1,2-dihydro-3-quinolinyl) methyl)cyclopentanecarboximidamide;

3-(1-4[(2R,6S)-2,6-Dimethyltetrahydro-[(2H)-pyridinyl]butyl-2-oxo-1,2-dihydro-3-quinolinyl) benzenecarboximidamide;

3-(1-6[(2R,6S)-2,6-Dimethyltetrahydro-1(2H)-pyridinyl]hexyl-2-oxo-1,2-dihydro-3-quinolinyl) benzenecarboximidamide;

2-[3-3-[Amino(imino)methyl]phenyl-2-oxo-1(2H)-quinolinyl]-N-2-[(2R,6S)-2,6-Dimethyltetrahydro-1(2)-pyridinyl]ethylacetamide;

3-[3-3-[Amino(imino)methyl]phenyl-2-oxo-1(2H)-quinolinyl]-N-[(2R,6S)-2,6-Dimethyltetrahydro-1(2) pyridinyl]methylpropanamide;

3-1-[2-[(2R,6S)-2,6-Dimethyltetrahydro-1(2H)-pyridinyl]ethylamino)ethyl]-2-oxo-1,2-dihydro-3-quinolinyl)benzenecarboximidamide;

3-[1-[(2R,6S)-2,6-Dimethyltetrahydro-[(2H)-pyridinyl]ethoxyethyl)-2-oxo-1,2dihydro-3-quinolinyl) benzenecarboximidamide; 3-(1-4[(2R,6S)-2,6-Dimethyltetrahydro-[(2H)-pyridinyl]phenyl-2-oxo-1,2-dihydro-3-quinolinyl)benzenecarboximidamide;

3-(4-[(2R,6S)-2,6-Dimethyltetrahydro-1(2H)-pyridinyl]benzyl-2-oxo-1,2-dihydro-3-quinolinyl) benzenecarboximidamide;

3-(1-4-(2R,6S)-2,6-Dimethyltetrahydro-1(2H)-pyridinyl]methylphenyl)-2-oxo 1,2-dihydro-3-quinolinyl) benzenecarboximidamide;

3-[1-(4-[(2R,6S)-2,6-Dimethyltetrahydro-[(2H)-pyridinyl]cyclohexylmethyl)-2-oxo-1,2-dihydro-3-quinolinyl)benzenecarboximidamide;

3-[1-(4-[(2R,6S)-2,6-Dimethyltetrahydro-1(2H)-pyridinyl]cyclohexylmethyl)$_2$-oxo-1,2-dihydro-3-quinolinyl)benzenecarboximidamide;

3-[1-(4-((2R,6S)-2,6-Dimethyltetrahydro-1(2H)-pyridinyl]methylcyclopentyl)-2-oxo-1,2-dihydro-3-quinolinyl)benzenecarboximidamide;

3-(1-3-[(2R,6S)-2,6-Dimethyltetrahydro-1(2H)-pyridinyl]cyclopentyl-2-oxo-1,2-dihydro-3-quinolinyl) benzenecarboximidamide;

3-[1-(3-[(2R,6S)2,6-Dimethyltetrahydro-1(2H)-pyridinyl]cyclopentylmethyl)-2-oxo-1,2-dihydro-3-quinolinyl)benzenecarboximidamide;

3-[1-(3-[(2R,6S)2,6-]Dimethyltetrahydro-[(2H)-pyridinyl]methylcyclopentyl)-2-oxo-1,2-dihydro-3-quinolinyl)benzenecarboximidamide;

3-(1-(E5-[(2R,6S)-2,6-Dimethyltetrahydro-1(2H)-pyridinyl]-2-pentenyl-2-oxo-1,2-dihydro-3-quinolinyl) benzenecarboximidamide;

3-[2-Oxo 1-(5-piperidinopentyl)-1,2-dihydro-3-quinolinyl]benzenecarboximidamide;

3-2-oxo-1-[5-(2,2,6,6-tetramethylpiperidino)pentyl]-1,2-dihydro-3-quinolinyl)benzenecarboximidamide;

1-5-[3-3-[Amino(imino)methyl]phenyl-2-oxo-[(2H)-quinolinyl]pentyl-2-piperidinecarboxylic acid;

1-5-3-3[Amino(imino)methyl]phenyl-2-oxo-1(2H)-quinolinyl]pentyl-3-piperidinecarboxylic acid;

1-5-3-3[Amino(imino)methyl]phenyl-2-oxo-1(2H)-quinolinyl]pentyl-3-piperidinecarboxylic acid;

3-1-[5-(3,5-Dimethylpiperidino)pentyl]-2-oxo-2-dihydro-3-quinolinylbenzenecarboxamide;

3-1-[5-(4-Hydroxypiperidino)pentyl]-2-oxo-1,2-dihydro-3-quinolinylbenzenecarboxamide;

3-1-[5-(2-Iminopiperidino)pentyl]-2-oxo-1,2-dihydro-3-quinolinylbenzenecarboxamide;

3-2-Oxo-1-[5-(4-oxopiperidino)pentyl]-1,2-dihydro-3-quinolinylbenzenecarboxamide;

3-[1-(5-2-[(Dimethylamino)methyl]piperidinopentyl)-2-oxo-1,2-dihydro-3-quinolinyl]benzenecarboxamide;

3(1-5-[4-(Diethylamino)piperidino]pentyl-2-oxo-1,2-dihydro-3-quinolinyl)benzenecarboxamide;

1-5-[3-3-[Amino(imino)methyl]phenyl-2-oxo-1(2H)-quinolinyl]pentyl-4-piperidinesulfonic acid;

3-2-Oxo-1-[5-(2-phenylpiperidino)pentyl]-1,2-dihydro-3-quinolinylbenzenecarboximidamide;

3-1-[5-(2,5-Dimethyl-1-pyrrolidinyl)pentyl]-2-oxo-1,2-dihydro-3-quinolinylbenzenecarboximidamide;

3-2-Oxo-1-[5-(1-pyrrolidinyl)pentyl]-1,2-dihydro-3-quinolinylbenzenecarboximidamide;

1-5-[3-3-[Amino(imino)methyl]phenyl-2-oxo-1(2H)-quinolinyl]pentyl-2-pyrrolidinecarboxylic acid;

N-(1-5-[3-3-[Amino(imino)methyl]phenyl-2-oxo-1(2H)-quinolinyl]pentyltetrahydro-1H-pyrrol-3-yl)N-methylacetamide;

3-1-[5-(3-Amino-1-pyrrolidinyl)pentyl]-2-oxo-1,2-dihydro-3-quinolinylbenzenecarboximidamide;

3-(1-5-[2,5-bis(Methoxymethyl)-1-pyrrolidinyl]pentyl-2-oxo-1,2-dihydro-3-quinolinyl)benzenecarboximidamide;

3-(1-S-[2-(Hydroxymethyl)-1-pyrrolidinyl]pentyl-2-oxo-1,2-dihydro-3-quinolinyl)benzenecarboximidamide;

3-(1-5-[2-(Hydroxymethyl)-5-methyl-1-pyrrolidinyl]pentyl-2-oxo-1,2-dihydro-3-quinolinyl)benzenecarboximidamide;

3-1-[5-(Diisopropylamino)pentyl]-2-oxo-1,2-dihydro-3-quinolinylbenzenecarboximidamide;

3-1-[5-(Diethylamino)pentyl]-2-oxo-1,2-dihydro-3-quinolinylbenzenecarboximidamide;

3-1-[5-(Methylamino)pentyl]-2-oxo-1,2-dihydro-3-quinolinylbenzenecarboximidamide;

3-1-[5-(1-Methyl-1H-imidazol-2-yl)pentyl]-2-oxo-1,2-dihydro-3-quinolinylbenzenecarboximidamide;

3-1-[5-(2,5-Dimethyl-1H-imidazol-1-yl)pentyl]-2-oxo-1,2-dihydro-3-quinolinylbenzenecarboximidamide;

3-[1-(5-Morpholinopentyl)-2-oxo-1,2-dihydro-3-quinolinyl]benzenecarboximidamide;

3-1-[5-(3,5-Dimethylmorpholino)pentyl]-2-oxo-1,2-dihydro-3-quinolinylbenzenecarboximidamide;

3-[2-oxo-1-(5-Piperazinopentyl)-1,2-dihydro-3-quinolinylbenzenecarboximidamide;

3-1-[5-(2,6-Dimethylpiperazino)pentyl]-2-oxo-1,2-dihydro-3-quinolinylbenzenecarboximidamide;

3-2-Oxo-1-5-(1H-pyrazol-1-yl)pentyl]-1,2-dihydro-3-quinolinylbenzenecarboximidamide;

3-[2-Oxo-1-(5-tetrahydro-1H-pyrazol-1-yl)pentyl)-1,2-dihydro-3-quinolinyl]benzenecarboximidamide;

3-1-[5-(2,5-Dimethyltetrahydro-1H-pyrazol-1-yl)pentyl]-2-oxo-1,2-dihydro-3-quinolinylbenzenecarboximidamide;

3-(7-Chloro-1-5-[(2R,6S)-2,6-dimethyltetrahydro 1(2H)pyridinyl]pentyl-2-oxo-1,2-dihydro-3-quinolinyl)benzenecarboximidamide;

3-(1-5-(2R,6S)2,6-Dimethyltetrahydro-1(2H)-pyridinyl]pentyl-7-fluoro-2-oxo-1,2-dihydro-3-quinolinyl)benzenecarboximidamide;

3-(1-5-[(2R,6S)-2,6 Dimethyltetrahydro-1(2H)-pyridinyl]pentyl-2-oxo-7-sulfanyl-1,2-dihydro-3-quinolinyl)benzenecarboximidamide;

3-(1-5-[(2R,6S)-2,6-Dimethyltetrahydro-[(2H)-pyridinyl]pentyl-7-(methylsulfonyl)2-oxo-1,2-dihydro-3-quinolyl]benzenecarboximidamide;

3-[1-5-[(2R,6S)-2,6-Dimethyltetrahydro-[(2H)pyridinyl]pentyl-2-oxo-7-(trifluoromethyl)-1,2-dihydro-3-quinolinyl]benzenecarboximidamide;

3-(1-5-[(2R,6S)-2,6-Dimethyltetrahydro-1(2H)-pyridinyl]pentyl-7-methyl-2-oxo-1,2-dihydro-3-quinolinyl)benzenecarboximidamide;

3-3-[Amino(imino)methyl]phenyl-1-5-[(2R,6S)-2,6-dimethyltetrahydro-1( ) pyridinyl]pentyl-2-oxo-1,2-dihydro-7-quinolinecarboxylic acid;

Methyl 3-3-[amino(imino)methyl]phenyl-1-5-[(2R,6S)-2,6-dimethyltetrahydro-1(2H)-pyridinyl]pentyl-2-oxo-1,2-dihydro-7-quinolinecarboxylate;

3-(7-Cyano-1-5-[(2R,6S)-2,6 dimethyltetrahydro-(2H)-pyridinyl]pentyl-2-oxo-1,2-dihydro-3-quinolinyl)benzenecarboximidamide;

3-3-(Amino(imino)methyl]phenyl-1-5-[(2R,6S)-2,6-dimethyltetrahydro-1(2H)-pyridinyl]pentyl-2-oxo-1,2-dihydro-3-quinolinecarboximidamide;

3-3-[Amino(imino)methyl]phenyl-1-5-(2R,6S)-2,6-dimethyltetrahydro-1(2H)-pyridinyl]pentyl-N-hydroxy-2-oxo-1,2-dihydro-7-quinolinecarboximidamide;

3-1-5-((2R,6S)-2,6-Dimethyltetrahydro-1(2H)pyridinyl]phenyl-7-hydrazino(imino)methyl]-2-oxo-1,2-dihydro-3-quinolinylbenzenecarboxamide;

3-3-(Amino(imino)methyl]phenyl-1-5-((2R,6S)-2,6-dimethyltetrahydro-1(2H)-pyridinyl]pentyl-2-oxo-1,2-dihydro-7-quinolinecarboxamide;

3-{[1-5-[(2R,6S)-2,6-Dimethyltetrahydro-1(2H)-pyridinyl]pentyl-7-(hydroxymethyl)-2-oxo-1,2-dihydro-3-quinolinyl]benzenecarboximidamide;

3-(7-(Aminomethyl)-1-5-[(2R,6S)-2,6-dimethyltetrahydro-1(2H)-pyridinyl]pentyl-2-oxo-1,2-dihydro-3-quinolinyl)benzenecarboximidamide;

3-(1-5-[[(2R,6S)-2,6-dimethyltetrahydro-1(2H)-pyridinyl]pentyl-7-nitro-2-oxo-1,2-dihydro-3-quinolinyl)benzenecarboximidamide;

3-(1-5-[(2R,6S)-2,6-Dimethyltetrahydro-1(21)pyridinyl]pentyl-7-hydroxy-2-oxo-1,2-dihydro-3-quinolinyl)benzenecarboximidamide;

3-1,5-[(2R,6S)-2,6-Dimethyltetrahydro-1(2H)-pyridinyl]pentyl-7-methoxy-2-oxo-1,2-dihydro-3-quinolinyl)benzenecarboximidamide;

3-(7-(Benzyloxy)-1-5-[(2R,6S)-2,6-dimethyltetrahydro-1(2H)pyridinyl]pentyl-2-oxo-1,2-dihydro-3-quinolinyl)benzenecarboximidamide;

2-[(3-3-[Amino(imino)methyl]phenyl-1-5-[(2R,6S)-2,6-dimethyltetrahydro-1(2-pyridinyl]pentyl-2-oxo-1,2-dihydro-7-quinolinyl)oxy]acetic acid, 3-[(3-3-[Amino(imino)methyl]phenyl-1-5-[(2R,6S)-2,6-dimethyltetrahydro-1(S)-pyridinyl]pentyl-2-oxo-1,2-dihydro-7-quinolinyl)oxy]propanoic acid;

4-[(3-3-[Amino(imino)methyl]phenyl-1-5-[(2R,6S)2,6-dimethyltetrahydro-1(2H)-pyridinyl]pentyl-2-oxo-1,2-dihydro-7-quinolinyl)oxy]butanoic acid;

2-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)amino]acetic acid;

3-[(3-3-[Amino(imino)methyl]phenyl-1-5-[(2R,6S)2,6-dimethyltetrahydro-1(2H)-pyridinyl]pentyl-2-oxo-1,2-dihydro-7-quinolinyl)amino]propanoic acid;

4-((3-3-[Amino(imino)methyl]phenyl-1-S-((2R,6S)-2,6-dimethyltetrahydro-1(2H)-pyridinyl]pentyl-2-oxo-1,2-dihydro-7-quinolinyl)amino]butanoic acid;

3-[1-5-[(2H)-2,6-dimethyltetrahydro-1(2H)-pyridinyl]pentyl-7-(2-hydroxyethoxy)-2-oxo-1,2 dihydro-3-quinolinyl)benzenecarboximidamide;

3-[1-5-[(2R,6S)-2,6-Dimethyltetrahydro-1(21H)-pyridinyl]pentyl-2-oxo-7-(1H-1,2,3,4-tetrazol-5-ylmethoxy)-1,2-dihydro quinolinyl]benzenecarboximidamide;

3-(7-Amino-1-5-(2R,6S)-2,6-dimethyltetrahydro-[(2-pyridinyl]pentyl-2-oxo-1,2-dihydro-3-quinolinyl)benzenecarboximidamide;

3-(7-Butylamino)-1-5-[(2R,6S)-2,6-dimethyltetrahydro-1(2H)-pyridinyl]pentyl 2-oxo-1,2-dihydro-3-quinolinyl)benzenecarboximidamide;

3-(7-(imino)methyl-1-5-(2R,6S)-2,6-dimethyltetrahydro-1(21H)-pyridinyl]pentyl-2-oxo-1,2-dihydro-3-quinolinyl)benzenecarboximidamide;

3-(7-Anilino 1-5-[(2R,6S)-2,6-dimethyltetrahydro-1(2H)-pyridinyl]pentyl-2-oxo-1,2-dihydro-3-quinolinyl)benzenecarboximidamide;

3-(7-(Benzylamino)-1-S-[(2R,6S)-2,6-dimethyltetrahydro-1(2H) pyridinyl]pentyl-2-oxo-1,2-dihydro 3-quinolinyl) benzenecarboxamide;

N-(3-3-[Amino(imino)methyl]phenyl-1-5-((2R,6S)-2,6-dimethyltetrahydro-1(2H)-pyridinyl]pentyl-2-oxo-1,2-dihydro-7-quinolinyl)acetamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)cyclohexanecarboxamide;

N-(3-3-[Amino(imino)methyl]phenyl-1-5-[(2R,6S)-2,6-dimethyltetrahydro-1(2-pyridinyl]pentyl-2-oxo-1,2 dihydro-7-quinolinyl)-2-cyclohexylacetamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)benzenecarboximidamide;

N-(3-3-[Amino(imino)methyl]phenyl-1-5-((2R,6S)-2,6-dimethyltetrahydro-[(2)-pyridinyl]pentyl-2-oxo-1,2-dihydro-7-quinolinyl)-2-phenylacetamide;

3-1-5-[(2R,6S)-2,6-Dimethyltetrahydro-1(2H)-pyridinyl]pentyl-7-[(methylsulfonyl)amino]-2-oxo-1,2-dihydro-3-quinolinylbenzenecarboximidamide;

3-(7-[(Cyclohexylsulfonyl)amino]-1-5-((2R,6S)-2,6-dimethyltetrahydro-1(2H)-pyridinyl)phenyl-2-oxo-1,2-dihydro-3-quinolinyl)benzenecarboximidamide;

3-(7-((Cyclohexylmethyl)sulfonyl]amino-1-5-[(2R,6S)-2,6-dimethyltetrahydro-1(2H)pyridinyl]pentyl-2-oxo-1,2-dihydro-3-quinolinyl)benzenecarboximidamide;

3-1-5-[(2R,6S)-2,6-Dimethyltetrahydro-1(2H)pyridinyl]pentyl-2-oxo-7-[(phenylsulfonyl)amino]-1,2 dihydro-3-quinolinylbenzenecarboximidamide;

3-(7-[(Benzylsulfonyl)amino]-1-5-C(2R,6S)-2,6-dimethyltetrahydro-[(2H)-pyridinyl]pentyl-2-oxo-1,2-dihydro-3-quinolinyl)benzenecarboximidamide;

3-(1-5-[(2R,6S)2,6-Dimethyltetrahydro-1(28)-pyridinyl]pentyl-2-oxo-1,2,3,4-tetrahydro-3-quinolinyl)benzenecarboximidamide;

1-5-[(2R,6S)-2,6-Dimethyltetrahydro-1(2H)-pyridinyl]pentyl-3-(3-hydroxyphenyl)3,4-dihydro-2(1H)-quinolinone;

3-(1-5-[(2R,6S)-2,6-Dimethyltetrahydro-1(2H)-pyridinyl]pentyl-2-oxo-1,2,3,4-tetrahydro-3-quinolinyl)N-hydroxybenzenecarboximidamide;

3-(1-5-[(2R,6S)-2,6-Dimethyltetrahydro-1(2-pyridinyl]pentyl-2-oxo-1,2,3,4-tetrahydro-3-quinolinyl)benzenecarboximidohydrazide;

3-[3-(Aminomethyl)phenyl]-1-5-[(2R,6S)-2,6-dimethyltetrahydro-1(2H)-pyridinyl pentyl-3,4-dihydro-2(1H)-quinolinone;

3-(3-Aminophenyl)-1-5-[(2R,6S)-2,6-dimethyltetrahydro-1(2H)-pyridinyl]pentyl-3,4-dihydro-2(1H)-quinolinone;

1-5-[(2R,6S)-2,6-Dimethyltetrahydro-1(2H)-pyridinyl]pentyl-3-[3-(methylamino)phenyl]-3,4-dihydro-2(1H)-quinolinone;

3-[3-(Dimethylamino)phenyl]-1-5-[(2R,6S)-2,6-Dimethyltetrahydro-1(2H)-pyridinyl]pentyl-3,4-dihydro-2(1H)quinolinone;

3-(1-5-[(2R,6S)-2,6-Dimethyltetrahydro-[(2)-pyridinyl]pentyl-2-oxo-1,2,3,4-tetrahydro-3-quinolinyl)-N-hydroxybenzenecarboximidamide;

3-(1-5-[(2R,6S)-2,6-Dimethyltetrahydro-1(2H)-pyridinyl]pentyl-2-oxo-1,2,3,4-tetrahydro-3-quinolinyl)tetrahydro-1(2-pyrrolidinecarboximidamide;

3-(1-5-[(2R,6S)-2,6-Dimethyltetrahydro-[(2H)-pyridinyl]pentyl-2-oxo-1,2,3,4-tetrahydro-3-quinolinyl)-1-pyrrolidinecarboximidamide;

1-5-[(2R,6S)-2,6-Dimethyltetrahydro-1(2H)-pyridinyl]pentyl-2-oxo-1,2,3,4-tetrahydro-3-quinolinyl)-2-thiophenecarboximidamide;

5-(1-5-[(2R,6S)-2,6-Dimethyltetrahydro-1(2H)-pyridinyl]pentyl-2-oxo-1,2,3,4-tetrahydro-3-quinolinyl)-2-furancarboximidamide;

2-(1-5-[(2R,6S)-2,6-Dimethyltetrahydro-[(2H)-pyridinyl]pentyl-2-oxo-1,2,3,4-tetrahydro-3-quinolinyl) 1,3-oxazole-carboximidamide;

5-(1-5-[(2R,6S)-2,6-Dimethyltetrahydro-1(2H)-pyridinyl]pentyl-2-oxo-1,2,3,4-tetrahydro-3-quinolinyl)-1,3-oxazole-2-carboximidamide;

1-5-[(2R,6S)-2,6-Dimethyltetrahydro-1(2H)-pyridinyl]pentyl-3-(1H-pyrazol-3-yl)-3,4-dihydro-2(1H)quinolinone;

1-5-[(2R,6S)-2,6-Dimethyltetrahydro-1(2H)pyridinyl]pentyl-3-tetrahydro-1H-pyrazol-3-yl-3,4-dihydro-2(1H)-quinolinone;

3-(1-5-((2R,6S)-2,6-Dimethyltetrahydro 1 (2H)-pyridinyl]pentyl-2-oxo-1,2,3,4-tetrahydro-3-quinolinyl)-1-pyrazolidinecarboximidamide;

5-(1-5-[(2R,6S)-2,6-Dimethyltetrahydro-1(2H)-pyridinyl]pentyl-2-oxo-1,2,3,4-tetrahydro-3-quinolinyl) 1H-imidazole-2-carboximidamide;

3-(2-Amino-1H-imidazol-5-yl)-1-5-[(2R,6S)-2,6-Dimethyltetrahydro-1(2H)-pyridinyl]pentyl-3,4-dihydro-2(1H)quinolinone;

2-(15-[(2R,6S)-2,6-Dimethyltetrahydro-1(2H)-pyridinyl]pentyl-2-oxo 1,2,3,4-tetrahydro-3-quinolinyl)1H-imidazole-5-carboximidamide;

3-(5-Amino-1H-imidazol-2-yl)-1-5-[(2R,6S)-2,6 Dimethyltetrahydro-1(2H)-pyridinyl]pentyl-3,4-dihydro-2(1H)-quinolinone;

1-5-[(2R,6S)-2,6-Dimethyltetrahydro-1(2H)pyridinyl]pentyl-3-(3-pyridinyl)-3,4-dihydro-2(1H)-quinolinone;

3-(6-Amino-3-pyridinyl)-1-5-[(2R,6S)-2,6-Dimethyltetrahydro-[(2H)-pyridinyl]pentyl-3,4-dihydro-2(1H)quinolinone;

3-(6-(Dimethylamino)-3-pyridinyl]-1-5-[(2R,6S)-2,6-dimethyltetrahydro- 1(2-pyridinyl]pentyl-3,4-dihydro-2(1H)quinolinone;

3-(6-Amino-2-pyridinyl)-1-5-[2R,6S)-2, 6Dimethyltetrahydro-1(2H)-pyridinyl]pentyl-3,4-dihydro-2(1}1)quinolinone;

6-(1-5-[(2R,6S)-2,6-Dimethyltetrahydro-1(2)-pyridinyl]pentyl-2-oxo-1,2,3,4-tetrahydro-3-quinolinyl)-2-pyridinecarboximidamide;

3-(2-Amino-4-pyridinyl)-1-S-(2R,6S)-2,6-dimethyltetrahydro-[(M-pyridinyl]pentyl-3,4-dihydro-2(1H)quinolinone;

4-(1-5-[(2R,6S)-2,6-Dimethyltetrahydro-1(2)-pyridinyl]pentyl-2-oxo-1,2,3,4-tetrahydro-3-quinolinyl)-2-pyridinecarboximidamide; (1-5-[(2R,6S)-2,6-Dimethyltetrahydro-1(2H)-pyridinyl]pentyl-2-oxo-1,2,3,4-tetrahydro-3-quinolinyl)$_2$-pyrimidinecarboximidamide;

3-Amino-4-pyrimidinyl)-1-5-[(2R,6S)-2,6-Dimethyltetrahydro-1(2H)-pyridinyl]pentyl-3,4-dihydro-2(1H)-quinolinone;

2-(1-5-[(2R,6S)-2,6-Dimethyltetrahydro-1(2H)-pyridinyl]pentyl-2-oxo-1,2,3,4-tetrahydro-3-quinolinyl)-4-pyrimidinecarboximidamide;

3-(4-Amino-2-pyrimidinyl)-1-S-[(2R,6S)-2,6-Dimethyltetrahydro-1(2H)-pyridinyl]pentyl-3,4-dihydro-2(1H)-quinolinone;

6-(1-5-[(2R,6S)-2,6-Dimethyltetrahydro-1(2H$_1$)-pyridinyl]pentyl-2-oxo-1,2,3,4-tetrahydro-3-quinolinyl)-2-pyrazinecarboximidamide;

3-(6-Amino-2-pyrazinyl)-1-5-[(2R,6S)-2,6-dimethyltetrahydro-1(2H)-pyridinyl-pentyl-3,4-dihydro-(2H)-quinolinone;

4-(1-5-[(2R,6S)-2,6-Dimethyltetrahydro-1(2H)pyridinyl]pentyl-2-oxo-1,2,3,4-tetrahydro-3-quinolinyl)-1,3,5-triazine-2-carboximidamide;

3-(4-Amino-1,3,5-triazin-2-yl)-1-5-[(2R,6S)-2,6-dimethyltetrahydro-1(2H)-pyridinyl]pentyl-3,4-dihydro-2(1)quinolinone;

6-(1-5-(1-5-((2R,6S)-2,6-Dimethyltetrahydro-[(2>pyridinyl]pentyl-2-oxo-1,2,3,4-tetrahydro-3-quinolinyl)-1,2,4-triazine-3-carboximidamide;

3-(3-Amino-1,2,4-triazin-5-yl)-1-5-[(2R,6S)-2, &dimethyltetrahydro 1 (2H)-pyridinyl)pentyl-3,4-dihydro-2(1H)quinolinone;

3-[(1-5-[(2R,6S)-2,6-Dimethyltetrahydro-(2H)-pyridinyl]pentyl-2-oxo 1,2,3,4-tetrahydro-3-quinolinyl)methyl]benzenecarboximidamide;

3-(3-Aminobenzyl)-1-5-((2R,6S)-2,6-dimethyltetrahydro-[(2H)-pyridinyl]pentyl-3,4-dihydro-2(1H)-quinolinone;

3-[3-(Aminomethyl)benzyl]-1-5-[(2R,6S)-2,6-dimethyltetrahydro-1(2H)-pyridinyl]pentyl-3,4-dihydro-2(1H)-quinolinone;

3-[(1-5-[(2R,6S)-2,6-dimethyltetrahydro-1(2H)-pyridinyl]pentyl-2-oxo-1,2,3,4-tetrahydro-3-quinolinyl)methyl]tetrahydro (2H)-pyridinecarboximidamide;

3-[(1-5-[(2R,6S)-2,6-dimethyltetrahydro(2H)-pyridinyl]pentyl-2-oxo-1,2,3,4-tetrahydro-3-quinolinyl)methyl]-1-pyrrolidinecarboximidamide;

5-[(1-5-[(2R,6S)-2,6-dimethyltetrahydro-[(2H)pyridinyl]pentyl-2-oxo-1,2,3,4-tetrahydro-3-quinolinyl)methyl]-2-thiophenecarboximidamide;

5-[(1-S-[(2R,6S)-2,6-Dimethyltetrahydro-1(2H)-pyridinyl]pentyl-2-oxo-1,2,3,4-tetrahydro-3-quinolinyl)methyl]-2-furancarboximidamide;

2-[(1-5-[(2R,6S)-2,6-dimethyltetrahydro-1(2H)-pyridinyl]pentyl-2-oxo-1,2,3,4-tetrahydro-3-quinolinyl)methyl]-1,3-oxazole-5-carboximidamide;

5-[(1-5-[(2R,6S)-2,6-dimethyltetrahydro-1(2H)-pyridinyl]pentyl-2-oxo-1,2,3,4-tetrahydro-3-quinolinyl)methyl]-1H-imidazole-2-carboximidamide;

2-[(1-5-[(2R,6S)-2,6-dimethyltetrahydro-1(2H)-pyridinyl]pentyl-2-oxo-1,2,3,4-tetrahydro-3-quinolinyl)methyl]-1H-imidazole-5-carboximidamide;

6-[(1-5-[(2R,6S)-2,6-dimethyltetrahydro-1H-pyridinyl]pentyl-2-oxo-1,2,3,4-tetrahydro-3-quinolinyl)methyl]-2-pyrazinecarboximidamide;

3-[(6-Amino-2-pyridinyl)methyl]-1-5-[(2R,6S)-2,6-dimethyltetrahydro-1(2H)-pyridinyl]pentyl-3,4-dihydro-2(1 quinolinone;

4-[(1-5-[(2R,6S)-2,6-dimethyltetrahydro-1(2H)-pyridinyl]pentyl-2-oxo-1,2,3,4-tetrahydro-3-quinolinyl)methyl]-2-pyrazinecarboximidamide;

3-[(2-Amino-4-pyrimidinyl)methyl-1-5-[(2R,6S)-2,6-dimethyltetrahydro-1(2H)-pyridinyl]pentyl-3,4-dihydro-2(1H)quinolinone;

2-[(1-5-[(2R,6S)-2,6-Dimethyltetrahydro-1(2H)-pyridinyl]pentyl-2-oxo-1,2,3,4-tetrahydro-3-quinolinyl)methyl]4-pyrazinecarboximidamide;

3-[(4-Amino-2-pyridinyl)methyl]-1-5-[(2R,6S)-2,6-dimethyltetrahydro-1(2H)-pyridinyl]pentyl-3,4-dihydro-2(1H)-quinolinone;

6-[(1-5-[(2R,6S)-2,6-dimethyltetrahydro-1(2H)-pyridinyl]pentyl-2-oxo-1,2,3,4-tetrahydro-3 quinolinyl)methyl]-2-pyrazinecarboximidamide;

3-[(6-Amino-2-pyrazinyl)methyl]-1-5-[(2R,6S)-2.6 dimethyltetrahydro-1(2H)-pyridinyl]pentyl-3,4-dihydro-2(1H)-quinolinone;

3-(3-Aminocyclohexyl)-1-5-[(2R,6S)-2,6-dimethyltetrahydro-[(2H)-pyridinyl]pentyl-2-yl-3,4-dihydro-2(1H)-quinolinone;

3-(1-S—C(2R,6S)-2,6-dimethyltetrahydro-1(2H)-pyridinyl]pentyl-2-oxo-1,2,3,4-tetrahydro-3-quinolinyl)cyclohexanecarboximidamide;

3-[(3-Aminocyclohexyl)methyl]-1-5-[(2R,6S)2,6-dimethyltetrahydro-1(2H)-pyridinyl)pentyl-3,4-dihydro-2(1H)-quinolinone;

3-[(1-5-[(2R,6S)-2,6-Dimethyltetrahydro-1(2H)-pyridinyl]pentyl-2-oxo-1,2,3,4-tetrahydro-3-quinolinyl)methyl]cyclohexanecarboximidamide;

3-(3-Aminocyclopentyl)-1-S-[(2R,6S)-2,6-dimethyltetrahydro-1(2H)-pyridinyl]pentyl-3,4-dihydro-2(1H)-quinolinone;

3-(1-5-[(2R,6S)-2,6-Dimethyltetrahydro-[(2H)-pyridinyl]pentyl-2-oxo-1,2,3,4-tetrahydro-3-quinolinyl]cyclohexanecarboximidamide;

3-[(3-Aminocyclopentyl)methyl]-1-5-[(2R,6S)-2,6-dimethyltetrahydro-1(2H)-pyridinyl]pentyl-3,4-dihydro-2(1H)-quinolinone;

3-[(1-5-[(2R,6S)-2,6-Dimethyltetrahydro-1(2H)-pyridinyl]pentyl 2-oxo-1,2,3,4-tetrahydro-3-quinolinyl)methyl]cyclopentanecarboximidamide;

3-(1-4[(2R,6S)-2,6-Dimethyltetrahydro-1(2H)pyridinyl] butyl-2-oxo-1,2,3,4 tetrahydro-3-quinolinyl) benzenecarboximidamide;

3-(1-6-[(2R,6S)-2,6-Dimethyltetrahydro-1(2H)-pyridinyl]hexyl-2-oxo-1,2,3,4-tetrahydro-3-quinolinyl)benzenecarboximidamide;

2-[3-3-[Amino(imino)methyl]phenyl-2-oxo-1(2H)-quinolinyl]-N-2-[(2R,6S)-2,6-dimethyltetrahydro-1(2H)-pyridinyl]ethylacetamide;

3-[3-3-(Amino(imino)methyl]phenyl-2-oxo-1(2H)quinolinyl]-N-[(2R,6S)-2,6-dimethyltetrahydro-1(2H)-pyridinyl]methylpropanamide;

3-1-[2-(2-[(2R,6S)-2,6-Dimethyltetrahydro-1(2H)-pyridinyl]ethylamino)ethyl]2-oxo-1,2,3,4-tetrahydro-3-quinolinyl]benzenecarboximidamide;

3-[1-2-2-[(2R,6S)-2,6-Dimethyltetrahydro-1(2H)-pyridinyl]ethoxyethyl)-2-oxo-1,2,3,4-tetrahydro-3-quinolinyl]benzenecarboximidamide;

3-(1-4-[(2R,6S)-2,6-Dimethyltetrahydro-1(2H)-pyridinyl]phenyl-2-oxo-1,2,3,4-tetrahydro-3-quinolinyl]benzenecarboximidamide;

3-(1-4-[(2R,6S)-2,6-Dimethyltetrahydro-1(2H)-pyridinyl]benzyl-2-oxo-1,2,3,4-tetrahydro-3-quinolinyl]benzenecarboximidamide;

3-[14-[(2R,6S)-2,6-Dimethyltetrahydro-1(2H)-pyridinyl]methylphenyl)-2-oxo-1,2,3,4-tetrahydro-3-quinolinyl]benzenecarboximidamide;

3-(1-4-[(2R,6S)2,6-Dimethyltetrahydro-1(2H)-pyridinyl]cyclohexyl-2-oxo-1,2,3,4-tetrahydro-3-quinolinyl]benzenecarboximidamide;

3-(1-4(2R,6S)-2,6-Dimethyltetrahydro-1(2H)-pyridinyl]cyclohexylmethyl)$_2$-oxo-1,2,3,4-tetrahydro-3-quinolinyl]benzenecarboximidamide;

3-[1-(4-[(2R,6S)-2,6-Dimethyltetrahydro-[(2H)-pyridinyl]methylcyclohexyl)-2-oxo-1,2,3,4-tetrahydro-3-quinolinyl]]benzenecarboximidamide;

3-(1-3(2R,6S)-2,6-Dimethyltetrahydro-1(pyridinyl]cyclopentyl-2-oxo-1,2,3,4-tetrahydro-3-quinolinyl]benzenecarboximidamide;

3-[1-(3-[(2R,6S)-2,6-Dimethyltetrahydro-1(2H) pyridinyl]cyclopentylmethyl)-2-oxo-1,2,3,4-tetrahydro-3-quinolyl]benzenecarboximidamide;

3-[1-(3-[(2R,6S)-2,6-Dimethyltetrahydro-1(2H)-pyridinyl]methylcyclopentyl)-2-oxo-1,2,3,4-tetrahydro-3-quinolinyl]benzenecarboximidamide;

3-[1-(E)-5-[(2R,6S)-2,6-Dimethyltetrahydro-1(2H)-pyridinyl]-2-pentenyl-2-oxo-1,2,3,4-tetrahydro-3-quinolinyl]benzenecarboximidamide;

3-[2-Oxo-1-(5-piperidinopentyl)-1,2,3,4-tetrahydro-3-quinolinyl]benzenecarboximidamide;

3-2-Oxo-1-1-[5-(2,2,6,6-tetramethylpiperidino)pentyl]-1,2,3,4-tetrahydro-3-quinolinylbenzenecarboximidamide;

1-5-[3-3-[Amino(imino)methyl]phenyl-2-oxo-[(2H)-quinolinyl]pentyl-2-piperidinecarboxylic acid;

1-5-[3-3-[Amino(imino)methyl]phenyl-2-oxo-[(2H)-quinolinyl]pentyl-3-piperidinecarboxylic acid;

1-5-3-3[Amino(imino)methyl]phenyl-2-oxo-[(2H)-quinolinyl]pentyl-4-piperidinecarboxylic acid;

3-1-[5-(3,5-Dimethylpiperidino)pentyl]-2-oxo-1,2,3,4-tetrahydro-3-quinolinylbenzenecarboximidamide;

3-1-[5-(4-Hydroxypiperidino)pentyl]-2-oxo-1,2,3,4-tetrahydro-3-quinolinylbenzenecarboximidamide;

3-1-[5-(2-Iminopiperidino)pentyl]-2-oxo-1,2,3,4-tetrahydro-3-quinolinylbenzenecarboximidamide;

3-2-Oxo-1-[5-(4-oxopiperidino)pentyl]-1,2,3,4-tetrahydro-3-quinolinylbenzenecarboximidamide;

3-1-(5-2-[(Dimethylamino)methyl]piperidinopentyl)-2-oxo-1,2,3,4-tetrahydro-3-quinolinyl]benzenecarboximidamide;

3-1-[5-[4-(Dimethylamino)piperidino]pentyl-2-oxo-1,2,3,4-tetrahydro-3-quinolinyl)benzenecarboximidamide;

1-5-[3-3-[amino(imino)methyl]phenyl-2-oxo 1(2H)-quinolinyl]pentyl-4-piperidinesulfonic acid;

3-2-Oxo-1-[5-(2-phenylpiperidino)pentyl]-1,2,3,4-tetrahydro-3-quinolinylbenzenecarboximidamide;

3-1-[5-(2,5-Dimethyl-1-pyrolidinyl)pentyl-2-oxo-1,2,3,4-tetrahydro-3-quinolinylbenzenecarboximidamide;

3-2-oxo-1-[5-(1-pyrrolidinyl)pentyl]-1,2,3,4-tetrahydro-3-quinolinylbenzenecarboximidamide;

1-5-[3-3-[no(imino)methyl]phenyl-2-oxo-1(2H)-quinolinyl]pentyl-2-pyrrolidinecarboxylic acid;

N-(-5-[3-3-[Amino(imino)methyl]phenyl-2-oxo-1(2H)-quinolinyl]pentyl-tetrahydro-1H-pyrrol-3-yl)-N-methylacetamide;

3-1 [5-(3-Amino-1-pyrrolidinyl)pentyl]-2-oxo-1,2,3,4-tetrahydro-3-quinolinylbenzenecarboximidamide;

3-(1-S-[2,5-bis(Methoxymethyl)-1-pyrrolidinyl]pentyl-2-oxo-1,2,3,4-tetrahydro-3-quinolinyl) benzenecarboximidamide;

3-(1-5-[2-(Hydroxymethyl)-1-pyrrolidinyl]pentyl-2-oxo 1,2,3,4-tetrahydro 3-quinolinyl) benzenecarboximidamide;

3-(1-5-[2-(Hydroxymethyl)-5-methyl-1-pyrrolidinyl]pentyl-2-oxo-1,2,3,4-tetrahydro-3-quinolinyl) benzenecarboximidamide;

3-1-[5-(Diisopropylamino)pentyl]-2-oxo-1,2,3,4-tetrahydro-3-quinolinylbenzenecarboximidamide;

3-1-[S-(Diethylamino)pentyl]-2-oxo-1,2,3,4-tetrahydro-3-quinolinylbenzenecarboximidamide;

3-1-[5-(Methylamino)pentyl]-2-oxo-1,2,3,4-tetrahydro-3-quinolinylbenzenecarboximidamide;

3-1-[5-(1-Methyl-1H-imidazol-2-yl)pentyl]-2-oxo-1,2,3,4-tetrahydro-3-quinolinylbenzenecarboximidamide;

3-1-[5-(2,5-Dimethyl-1H-imidazol-1-yl)pentyl)-2-oxo-1,2,3,4-tetrahydro-3-quinolinylbenzenecarboximidamide;

3-[1-(5-Morpholinopentyl)-2-oxo-1,2,3,4-tetrahydro-3-quinolinyl]benzenecarboximidamide;

3-1-[5-(3,5-Dimethylmorpholino)pentyl]-2-oxo-1,2,3,4-tetrahydro-3-quinolinylbenzenecarboximidamide;

3-[2-oxo-1 1-5-piperazino)pentyl]-1,2,3,4-tetrahydro-3-quinolinylbenzenecarboximidamide;

3-1-[5-(2,6-Dimethylpiperazino)pentyl]-2-oxo-1,2,3,4-tetrahydro-3-quinolinylbenzenecarboximidamide;

3-2-oxo-1-[5-(1H-pyrazol-1-yl)pentyl]-1,2,3,4-tetrahydro-3-quinolinylbenzenecarboximidamide;

3-[2-Oxo-1-(5-tetrahydro-H-pyrazol-1-yl)pentyl]-1,2,3,4-tetrahydro-3-quinolinyl]benzenecarboximidamide;

3-1-(5-(2,5-dimethyltetrahydro-1H-pyrazol-1-yl)pentyl]-2-oxo-1,2,3,4-tetrahydro-3-quinolinylbenzenecarboximidamide;

3-(7-Chloro-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-(1-5-[(2R,6S)-2,6-dimethyltetrahydro-1(2H)-pyridinyl]pentyl-7-fluoro-2-oxo 1,2,3,4-tetrahydro-3-quinolinyl)benzenecarboximidamide;

3-(1-5-[(2R,6S)-2,6-Dimethyltetrahydro-1(2H)-pyridinyl]pentyl-2-oxo-7-sulfanyl-1,2,3,4-tetrahydro-3-quinolinyl)benzenecarboximidamide;

3-[1-5-[(2R,6S)-2,6-Dimethyltetrahydro-[(2H)-pyridinyl]pentyl-7-(methylsulfanyl)-2-oxo-1,2,3,4-tetrahydro-3-quinolinyl]benzenecarboximidamide;

3-[1-5-[(2R,6S)-2,6-Dimethyltetrahydro-1(2H)-pyridinyl]pentyl-2-oxo-7-(trifluoromethyl)-1,2,3,4-tetra-3-quinolinyl)benzenecarboximidamide;

3-(1-5-[(2R,6S)-2,6-dimethyltetrahydro-1(2H)-pyridinyl]pentyl-7-methyl-2-oxo-1,2,3,4-tetrahydro-3-quinolinyl)benzenecarboximidamide;

3-3-[Amino(imino)methyl]phenyl-1-5-[(2R,6S)-2,6-dimethyltetrahydro-1(2H)-pyridinyl]pentyl-2-oxo-1,2,3,4-tetrahydro-7-quinolinecarboxylic acid;

methyl 3-3-(Amino(imino)methyl]phenyl-1-S-[(2R,6S)-2,6-dimethyltetrahydro 1(2H)-pyridinyl]pentyl-2-oxo-1,2,3,4-tetrahydro-7-quinolinecarboxylate;

3-(7-Cyano-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-3-[Amino(imino)methyl-3-phenyl-1-5-[(2R,6S)-2,6-dimethyltetrahydro-1(2H)-pyridinyl]pentyl-2-oxo-1,2,3,4-tetrahydro-7-quinolinecarboximidamide;

3-3-[Amino(imino)methyl]phenyl-1-5-[(2R,6S)-2,6-dimethyltetrahydro-[(21)-pyridinyl]pentyl-N-hydroxy-2-oxo 1,2,3,4-tetrahydro-7-quinolinecarboximidamide;

3-1-5-[(2R,6S)-2,6-Dimethyltetrahydro-1(2H)pyridinyl]pentyl-7-[hydrazino(imino)methyl]-2-oxo-1,2,3,4-tetrahydro-3-quinolinylbenzenecarboximidamide;

3-3-[Amino(imino)methyl]phenyl-1-5-[(2R,6S)-2,6-dimethyltetrahydro-1(2H)-pyridinyl]pentyl-2-oxo-1,2,3,4-tetrahydro-7-quinolinecarboxamide;

3-[1-5-[(2R,6S)-2,6-Dimethyltetrahydro-1(pyridinyl]pentyl-7-(hydroxymethyl)-2-oxo-1,2,3,4-tetrahydro-3-quinolyl]benzenecarboximidamide;

3-(7-(Aminomethyl)-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-(1-5-[(2R,6S)-2,6-Dimethyltetrahydro-1(2H)-pyridinyl]pentyl-7-nitro-2-oxo-1,2,3,4-tetrahydro-3-quinolinyl)benzenecarboximidamide;

3-(1-[(2R, 6S)-2,6-Dimethyltetrahydro-1(2-pyridinyl]pentyl-7-hydroxy-2-oxo-1,2,3,4-tetrahydro-3-quinolinyl)benzenecarboximidamide;

3-(1-5-((2R,6S)-2,6-Dimethyltetrahydro-1(2H)-pyridinyl]pyridinyl-7-methoxy-2-oxo-1,2,3-tetrahydro-3-quinolinyl)benzenecarboximidamide;

3-(7-(Benzyloxy)-1-5-[(2R,6S)-2,6-dimethyltetrahydro-1(2H)-pyridinyl]pentyl-2-oxo-1,2,3,4-tetrahydro-3-quinolinyl)benzenecarboximidamide;

2-[(3-3-[Amino(imino)methyl]phenyl-1-5-[(2R,6S)-2,6-dimethyltetrahydro-1(2H)-pyridinyl]pentyl-2-oxo-1,2-dihydro-quinolinyl)oxy]acetic acid;

3-[(3-3-[Amino(imino)methyl]phenyl--5-[(2R,6S)-2,6-dimethyltetrahydro-1(2H)-pyridinyl]pentyl-2-oxo-1,2-dihydro-7-quinolinyl)oxy]propanoic acid;

4-[(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)oxy]butanoic acid;

2-[(3-3-(Amino(imino)methyl]phenyl-1-5-[(2R,6S)-2,6-dimethyltetrahydro-1(2H)-pyridinyl]pentyl-2-oxo-1,2-dihydro-7-quinolinyl)amino]acetic acid;

3-[(3-3-[Amino(imino)methyl]phenyl-1-5-[(2R,6S)-2,6-dimethyltetrahydro-1(pyridinyl-pentyl-2-oxo-1,2-dihydro-7-quinolinyl)amino]propanoic acid;

4-(3-3-[Amino(imino)methyl]phenyl-1-5-[(2R,6S)-2-dimethyltetrahydro-1(2H)pyridinyl]pentyl-2-oxo-1,2-dihydro-7-quinolinyl)amino]butanoic acid;

3-[1-5-[(2R,6S)-2,6-Dimethyltetrahydro-1(pyridinyl]pentyl-7-(2-hydroxyethoxy)-2-oxo-1,2,3,4-tetrahydro-3-quinolinyl]benzenecarboximidamide;

3-[1-5-[(2R,6S)-2,6-Dimethyltetrahydro-1(2-pyridinyl]pentyl-2-oxo-7-(1H-1,2,3,4-tetrahydro-1-5-ylmethoxy)-1,2,3,4-tetrahydro-3-quinolinyl]benzenecarboximidamide;

3-(7-Amino-1-5-[(2R,6S)-2,6-dimethyltetrahydro(2H)-pyridinyl]pentyl-2-oxo-1,2,3,4-tetrahydro-3-quinolinyl)benzenecarboximidamide;

3-(7-(Butylamino)-1-5-(2R,6S)-2,6-dimethyltetrahydro-1(2H)-pyridinyl]pentyl-2-oxo-1,2,3,4-tetrahydro-3-quinolinyl)benzenecarboximidamide;

3-(7-(Dimethylamino)-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-(7-Anilino-1-5-t(2R,6S)-2,6-dimethyltetrahydro-1(2H)-pyridinyl]pentyl-2-oxo-1,2,3,4-tetrahydro-3-quinolinyl)benzenecarboximidamide;

3-(7(Benzylamino)-1-5-[(2R,6S)-2,6 dimethyltetrahydro-1(2H)-pyridinyl]pentyl-2-oxo 1,2,3,4-tetrahydro-3-quinolinyl)benzenecarboximidamide;

N3-3-[Amino(no)methyl]phenyl-1-5-[(2R,6S)-2,6,4-dimethyltetrahydro-1(2H)-pyridinyl]pentyl-2-oxo 1,2-dihydro-7-quinolinyl)acetamide;

N-(3-3-[Amino(imino)methyl]phenyl-1-5-[(2R,6S)-2,6-dimethyltetrahydro-1(2H)pyridinyl]pentyl-2-oxo-1,2-dihydro-7-quinolinyl)cyclohexanecarboxamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolinyl)-2-cyclohexylacetamide;

N-(3-3-[Amino(imino)methyl]phenyl-1-5-[(2R,6S)-2,6-dimethyltetrahydro 1(2H)-pyridinyl]pentyl-2-oxo-1,2-dihydro-quinolinyl)benzenecarboxamide;

N-(3-3-[Amino(imino)methyl]phenyl-1-5-[(2R,6S)-2,6-dimethyltetrahydro-1(2H)-pyridinyl]pentyl-2-oxo-1,2-dihydro-7-quinolyl)-2-phenylacetamide;

3-1-5-[(2R,6S)-2,6-Dimethyltetrahydro-1(2H)-pyridinyl]pentyl-7-[(methylsulfonyl)amino]-2-oxo-1,2,3,4-tetrahydro-3-quinolinylbenzenecarboximidamide;

3-(7-[(Cyclohexylsulfonyl)amino]-1-5-[(2R,6S)-2,6-dimethyltetrahydro-1(2H)-pyridinyl]pentyl-2-oxo-1,2,3,4-tetrahydro-3-quinolinyl)benzenecarboximidamide;

3-(7-[(Cyclohexylmethyl)sulfonyl]amino-1-5-[(2R,6S)-2,6-dimethyltetrahydro-1(2H)-pyridinyl]pentyl-2-oxo-1,2,3,4-tetrahydro-3-quinolinyl)benzenecarboximidamide;

1-[5-(2,6-Dimethyl-piperidin-1-yl)-pentyl]-3-(4-methoxy-phenyl)-3,4-dihydro-1H-quinolin-2-one;

3-1-5-[(2R,6S)-2,6-Dimethyltetrahydro-1(2H)-pyridinyl]
pentyl-2-oxo-7-[(phenylsulfonyl)amino]-1,2,3,4-
tetrahydro-3-quinolinylbenzenecarboximidamide; or 3-(7-[(Benzylsulfonyl)amino]-1-5-[(2R,6S)-2,6-
dimethyltetrahydro-1(2H)-pyridinyl]pentyl-2-oxo-1,2,
3,4-tetrahydro-3-quinolinyl)benzenecarboximidamide.

12. A compound which is:

3-(1-5-[(2R,6S)-2,6-dimethyltetrahydro-1(2H)-pyridinyl]
pentyl-2-oxo-1,2-dihydro-3-quinolinyl)
benzenecarboximidamide;

3-(1-5-[(2R,6S)-2,6-Dimethyltetrahydro-1(2H)-
pyridinyl]pentyl-2-oxo-1,2-dihydro-3-quinolinyl)-N-
hydroxybenzenecarboximidamide;

3-[3-(Aminomethyl)phenyl]3-1-5-[(2R,6S)-2,6-
dimethyltetrahydro-1(2H)-pyridinyl]pentyl-2(1H)-
quinolinone; or 3-(1-5-[(2R,6S)-2,6-Dimethyltetrahydro-1(2H)-
pyridinyl]pentyl-2-oxo-1,2-dihydro-3-quinolinyl)-4-
hydroxybenzenecarboximidamide.

13. A compound which is:

3-(1-5-[(2R,6S)-2,6-Dimethyltetrahydro-1(2H)-
pyridinyl]pentyl-2-oxo-1,2,3,4-tetrahydro-3-
quinolinyl)-4-hydroxybenzene carboximid amide; or 3-(1-5-[(2R,6S)-2,6-Dimethyltetrahydro-1(2H)-
pyridinyl]pentyl-2-oxo-1,2-dihydro-3-quinolinyl)-4-
hydroxybenzenecarboximidamide.

14. A method for the treatment of thrombotic disorders in a mammal comprising administering to said mammal an effective amount of a compound according to claim 1.

15. A method according to claim 14, wherein said disorder is venous thrombosis.

16. A method according to claim 14, wherein said disorder is arterial thrombosis.

17. A method according to claim 14, wherein said disorder is pulmonary embolism.

18. A method according to claim 14, wherein said disorder is myocardial infarction.

19. A method according to claim 14, wherein said disorder is cerebral infarction.

20. A method according to claim 14, wherein said disorder is restenosis.

21. A method according to claim 14, wherein said disorder is cancer.

22. A method according to claim 14, wherein said disorder is angina.

23. A method according to claim 14, wherein said disorder is diabetes.

24. A method according to claim 14, wherein said disorder is heart failure.

25. A method according to claim 14, wherein said disorder is arterial fibrillation.

26. A pharmaceutical formulation comprising a compound of claim 1 admixed with a carrier, diluent, or excipient.

27. A pharmaceutical formulation comprising a compound of claim 2 together with a carrier, diluent, or excipient.

28. A pharmaceutical formulation comprising a compound of claim 11 together with a carrier, diluent, or excipient.

29. A method for inhibiting serine proteases comprising administering to a mammal an effective amount of serine protease inhibitor of claim 1.

30. A method according to claim 29, wherein said serine protease is factor Xa.

* * * * *